United States Patent
Bafundo et al.

(10) Patent No.: US 10,413,581 B2
(45) Date of Patent: Sep. 17, 2019

(54) COMBINATION, COMPOSITION, AND METHOD OF ADMINISTERING THE COMBINATION OR COMPOSITION TO ANIMALS

(71) Applicants: Phibro Animal Health Corporation, Teaneck, NJ (US); Desert King International LLC, San Diego, CA (US)

(72) Inventors: Kenneth W. Bafundo, Teaneck, NJ (US); A. Bruce Johnson, Teaneck, NJ (US); David Calabotta, Teaneck, NJ (US); Wendell Knehans, Teaneck, NJ (US)

(73) Assignees: Phibro Animal Health Corporation, Teaneck, NJ (US); Desert King International LLC, San Diego, CA (US)

( * ) Notice: Subject to any disclaimer, the term of this patent is extended or adjusted under 35 U.S.C. 154(b) by 102 days.

(21) Appl. No.: 15/359,342

(22) Filed: Nov. 22, 2016

(65) Prior Publication Data
US 2017/0072002 A1 Mar. 16, 2017

Related U.S. Application Data

(63) Continuation-in-part of application No. PCT/US2015/032301, filed on May 22, 2015.

(60) Provisional application No. 62/002,527, filed on May 23, 2014.

(51) Int. Cl.
| | |
|---|---|
| A61K 38/05 | (2006.01) |
| A61K 38/15 | (2006.01) |
| A23K 50/00 | (2016.01) |
| A23K 50/70 | (2016.01) |
| A23K 50/75 | (2016.01) |
| A61K 39/012 | (2006.01) |
| A61K 36/88 | (2006.01) |
| A61K 36/896 | (2006.01) |
| A61K 36/73 | (2006.01) |
| A23K 20/10 | (2016.01) |
| A61K 31/35 | (2006.01) |
| A61K 36/185 | (2006.01) |
| A61K 39/00 | (2006.01) |

(52) U.S. Cl.
CPC ............ *A61K 36/88* (2013.01); *A23K 20/10* (2016.05); *A23K 50/00* (2016.05); *A23K 50/70* (2016.05); *A23K 50/75* (2016.05); *A61K 31/35* (2013.01); *A61K 36/185* (2013.01); *A61K 36/73* (2013.01); *A61K 36/896* (2013.01); *A61K 38/05* (2013.01); *A61K 38/15* (2013.01); *A61K 39/012* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 6,569,843 B1 | 5/2003 | Walker | |
| 2006/0051365 A1 | 3/2006 | Gorenflot et al. | |
| 2008/0274211 A1 | 11/2008 | McNeff et al. | |
| 2014/0037698 A1 | 2/2014 | Perez | |

FOREIGN PATENT DOCUMENTS

| | | |
|---|---|---|
| CN | 1678349 A | 10/2005 |
| CN | 101563090 A | 10/2009 |
| CN | 102333877 A | 1/2012 |
| EP | 0 791 298 A1 | 8/1997 |
| JP | 7-107923 | 4/1995 |
| JP | 8-131089 | 5/1996 |
| JP | H09-224585 | 9/1997 |
| JP | 2004-525617 | 8/2004 |
| WO | WO 02/052949 | 7/2002 |
| WO | WO 02/067963 | 9/2002 |

OTHER PUBLICATIONS

Cheeke 2009 (Applications of saponins as feed additives in poultry production—Engormix, published Dec. 3, 2009) (Year: 2009).*
Alfaro et al 2007 ,J. Appl. Poult. Res. 16:248-254. (Year: 2007).*
Shojadoost 2013 , The Journal of Applied Poultry Research, vol. 22, Issue 2, pp. 160-167. (Year: 2013).*
Abbas et al., "Botanicals: an alternative approach for the control of avian coccidiosis," *World Poultry Science Journal*, 68(2): 203-215, Jun. 1, 2012.
Al-Bar et al., "Effect of dietary Yucca shidegria extract (Deodorase) on environmental ammonia and growth performance of chickens and rabbits," *Journal of Animal Science*, 71(1): p. 114, Jan. 1, 1993.
Cheeke, "Actual and potential applications of *Yucca schidigera* and *Quillaja saponaria* saponins in human and animal nutrition," *Proceedings of the American Society of Animal Science*, pp. 1-10, 1999.
Cheeke, "Actual and potential applications of *Yucca schidigera* and *Quillaja saponaria* saponins in human and animal nutrition," *Recent Advances in Animal Nutrition in Australia*, vol. 13, pp. 115-126, 2001.

(Continued)

*Primary Examiner* — Padmavathi Baskar
(74) *Attorney, Agent, or Firm* — Klarquist Sparkman, LLP

(57) ABSTRACT

Disclosed herein are embodiments of a combination and/or composition for administration to animals. In some embodiments, the combination and/or composition can be administered to treat and/or prevent a disease in animals. In some embodiments, the combination and/or composition can be administered to promote animal health. In some embodiments, the combination comprises a composition comprising *Yucca schidigera*, *Quillaja saponaria*, and combinations thereof and a composition comprising an antimicrobial, an antibiotic, an anticoccidial, a vaccine, or combinations thereof. The combinations or compositions disclosed herein can also improve feed conversion rates in animals.

24 Claims, 45 Drawing Sheets
(23 of 45 Drawing Sheet(s) Filed in Color)

(56) References Cited

OTHER PUBLICATIONS

Cheeke et al., "Yucca, quillaja may have role in animal nutrition," *Feedstuffs*, 77(3): 8 pages, Jan. 17, 2005.
Choi et al., "Enhancement of aerobic biodegradation in an oxygen-limiting environment using a saponin-based microbubble suspension," *Environmental Pollution*, vol. 157, 2197-2202, 2009.
Garcia et al., "Effect of *Quillaja saponaria* Extract on Passive Immunization in Pig Model," *Journal of Animal and Veterinary Advances*, 3(8): 535-541, 2004.
Hassan et al., "Hemolytic and Antimicrobial Activities Differ Among Saponin-rich Extracts from Guar, Quillaja, Yucca, and Soybean," *Applied Biochemistry and Biotechnology*, 162(4): 1008-1017, Nov. 15, 2009.
Hauptli et al. "Feeding sows in gestation and lactation with diets containing saponins," Ciênc. Rural, Santa Maria, v.36, n.2, p. 610-616, Mar./Apr. 2006.
Ilsley et al., "Effect of dietary supplementation of sows with quillaja saponins during gestation on colostrum composition and performance of piglets suckled," *Animal Science*, 80: 179-184, 2005.
International Search Report and Written Opinion issued for International Application No. PCT/US2015/032301, dated Jul. 17, 2015 (11 pages).
Johnston et al., "Evaluation of DSS4-0 Yucca saponin on broiler performance," *Poultry Science*, 59(7): 1625, Jan. 1, 1980.
Nazeer et al., "Effect of Yucca Saponin on Urease Activity and Development of Ascites in Broiler Chickens," *International Journal of Poultry Science*, 1(6): 174-178, Jun. 2002.
Turner et al., "Effects of a *Quillaja saponaria* extract on growth performance and immune function of weanling pigs challenged with *Salmonella typhimurium*," *Journal of Animal Science*, 80: 1939-1946, 2002.
Vaclavkova et al., "Effect of Herbal Extract on Growth Parameters of Weaned Piglets," *Research in Pig Breeding*, 2(2): 36-38, 2008.
Veit et al., "Effects of phytogenic feed additives containing *Quillja saponaria* on ammonia in fattening pigs," Proceedings of the XVth International Congress of the International Society for Animal Hygiene, Vienna, Austria, Jul. 3-7, 2011, vol. 3 2011 pp. 1255-1257.
Zhao, "Mechanisms of quorum sensing and strategies for quorum sensing disruption in aquaculture pathogens," *Journal of Fish Diseases*, 38(9): 771-786, Sep. 15, 2014.
Yeo et al., "Effect of Feeding Diets Containing an Antibiotic, a Probiotic, or Yucca Extract on Growth and Intestinal Urease Activity in Broiler Chicks," *Poultry Science*, 76(2): 381-385, Mar. 1997.
Naknukool et al., "Stimulating Macrophage Activity in Mice and Humans by Oral Administration of Quillaja Saponin," *Biosci. Biotechnol. Biochem.*, 75(10): 18891893, Oct. 7, 2011.
Alfaro et al., "Use of Yucca schidigera extract in broiler diets and its effect on performance results obtained with different coccidiosis control methods," *Journal of Applied Poultry Research*, 16(2): 248-254, Jul. 1, 2007.
Cheeke et al., "Applications of saponins as feed additives in poultry production," 20th Annual Australian Poultry Science Symposium, pp. 50-55, Feb. 9-11, 2009.
Office Action issued for Russian Application No. 2016149801, dated Nov. 14, 2018.
Office Action issued for Israeli Application No. 249061, dated Dec. 20, 2018.
Grabensteiner et al., "Differences in the in vitro susceptibility of mono-eukaryotic cultures of *Histomonas meleagridis, Tetratrichomonas gallinarum* and *Blastocystis* sp. to natural organic compounds," *Parasitol Res.*, vol. 101, pp. 193-199, Feb. 7, 2007.
McAllister et al., "Studies on the use of *Yucca schidigera* to control giardiasis," *Veterinary Parasitology*, vol. 97, pp. 85-99, May 11, 2001.
Patra et al., "Effects of quillaja and yucca saponins on communities and select populations of rumen bacteria and archaea, and fermentation in vitro," *Journal of Applied Microbiology*, vol. 112, pp. 1329-1340, Sep. 13, 2012.
Rambozzi et al., "In vivo Anticoccidial Activity of *Yucca schidigera* Saponins in Naturally Infected Calves," *Journal of Animal and Veterinary Advances*, 10(3): 391-394, 2011.
Casillas-Hernández et al., "Evaluación de NUTRIFITO™ como promotor natural en el alimento, para la producción comercial del camarón blanco del Pacifico *Litopenaeus vannamei*," Revista Latinoamericano de Recursos Naturales 5(2):174-179, 2009 with English language abstract.
Francis et al., "*Quillaja* saponins—a natural growth promoter for fish," *Animal Feed Science and Technology* 121:147-157, 2005.
Hernández-Acosta et al., "The effects of *Yucca schidigera* and *Quillaja saponaria* on growth performance and enzymes activities of juvenile shrimp *Litopenaeus vannamei* cultured in low-salinity water," *Latin American Journal of Aquatic Research* 44(1):121-128, Mar. 1, 2016.
Office Action issued by Japan Patent Office for Japanese Application No. 2017-514395 dated May 28, 2019.
Office Action issued by Russian Patent Office for Russian Application No. 2016149801 dated May 17, 2019.
Santacruz-Reyes et al., "Efficacy of *Yucca schidigera* extract from ammonia reduction in fresh water: Effectiveness analysis and empirical modeling approach," *Aquaculture* 287:106-111, 2009.
Bafundo et al., "Anticoccidial Effects of Magni-Phi™, a Triterpenoid Saponin, When Combined with Salinomycin or Used to Support the Effectiveness of a Coccidiosis Vaccine," *Abstract and slide presentation from the American Association of Avian Pathologists Meeting*, Jul. 2015.
Bafundo et al., "Performance and Anticoccidial Effects of Magni-Phi in Coccidia-Vaccinated Broilers," *International Poultry Scientific Forum*, p. 10, Jan. 2016.
Bafundo et al., "The effects of Nutrafito Plus and virginiamycin on the performance and anticoccidial responses of broilers vaccinated for coccidiosis," *Poultry Sci.* 93: (E-Suppl. 1) p. 41. Jul. 2014.
Espejo Marquinez "Evaluación experimental de las saponinas del quillay (Quillaja saponaria) como inhibidora del desarrollo de coccidias intestinales en pollos de engorda," Thesis, Universidad de Chile, availability date of Jul. 2, 2015.
Hassan, S.M. Antimicrobial activities of saponin-rich guar meal extract. Ph.D. Thesis, Texas A&M University, May 2008.
Johnson et al., "Anticoccidial Drugs: Lesion Scoring Techniques in Battery and Floor-Pen Experiments with Chickens," *Experimental Parasitology*, 28(1): 30-36, Aug. 1970.
Scheurer, et al., "Effect of 3 dietary phytogenic products on production performance and coccidiosis in challenged broiler chickens," J. Appl. Poult. Res. 22:591-599, Oct. 1, 2013.
Sen, S., H.P.S. Makkar, S. Muetzel, and K. Becker. Effect of *Quillaja saponaria* saponins and *Yucca schidigera* plant extracts on growth of *Escherichia coli*. Lett. Appl. Microbiol. 27:35-38. Jul. 1998.
Sparg et al., "Biological activities and distribution of plant saponins," *Journal of Ethnopharmacology*, 94(2-3): 219-243, Oct. 2004.
Johnston et al., "Broiler Performance with Dss40 Yucca Saponin in Combination with Monensin," *Poultry Science*, 61(6): 1052-1054, Jun. 1982.
Yuan et al., "World Medicinal Botanicals," p. 312, Jan. 31, 2012.
Wang, "Cosmetic Plant Materials," p. 353, Jun. 30, 2012.
Office Action and Search Report issued by the Chinese National Intellectual Property Administration for Chinese Application No. 201580035572.6 dated Jan. 18, 2019.

* cited by examiner

COMBINATION, COMPOSITION, AND METHOD OF ADMINISTERING THE COMBINATION OR COMPOSITION TO ANIMALS

CROSS REFERENCE TO RELATED APPLICATION

This application is a continuation-in-part of International Application No. PCT/US2015/032301, filed on May 22, 2015, which in turn claims the benefit of the earlier filing date of U.S. Provisional Application No. 62/002,527, filed May 23, 2014. These prior applications are incorporated herein by reference in their entirety.

FIELD

This disclosure concerns embodiments of a combination and/or composition for administration to animals, as well as methods of making the combination and/or composition and administering the same to animals.

BACKGROUND

Feed conversion rates or ratios (FCR) provide animal producers a method for monitoring the efficiency of raising animals. Estimating the amount of feed required per unit of body gain for animals provides the animal producers the ability to effectively budget costs associated with raising the animals. Feed conversion rates also can be used to reduce risks associated with raising animals, such as feed shortfalls or waste, and can facilitate determining profit margins.

Coccidiosis is a parasitic disease of the intestinal tract of animals caused by coccidian protozoa of the genus *Eimeria*. The disease can spread amongst animals by contact with infected feces by means of an infective form called the oocyst. Coccidiosis is a significant disease of certain animals, such as domestic fowl and livestock, as it can affect animals at a very young age. It can be fatal or compromise animal health, thereby impairing the feed conversion rate of the animals. Thus, production, reproductive efficiency and animal health are adversely affected by coccidiosis. Diseases, such as coccidiosis, cause significant economic losses in certain animal industries. Such diseases also can negatively affect the health of domesticated animals.

SUMMARY

Disclosed herein are embodiments of a combination comprising a first combination comprising *Yucca*, *Quillaja*, or both; and a second composition comprising an antibiotic, an antimicrobial, an anticoccidial agent, or a combination thereof. In some embodiments, the combination comprises 200 ppm to 5,000 ppm of a first composition comprising *Quillaja saponaria*, *Yucca schidigera*, or a combination thereof, and a second composition comprising an antimicrobial, an antibiotic, an anticoccidial agent, or combinations thereof. The second composition may comprise 10 ppm to 30 ppm Virginiamycin and/or 50 ppm to 70 ppm Salinomycin. In some embodiments, the first composition can comprise a mixture of *Quillaja saponaria* and *Yucca schidigera* in a ratio ranging from 70:30 *Quillaja saponaria:Yucca schidigera* to 90:10 *Quillaja saponaria:Yucca schidigera*.

Embodiments of the combinations may also include a third composition comprising a vaccine, and in some embodiments, the vaccine is a composition comprising oocysts derived from *Eimeria acervulina*, *Eimeria mivati*, *Eimeria maxima*, *Eimeria tenella*, *Eimeria mitis*, *Eimeria necatrix*, *Eimeria praecox*, *Eimeria brunetti*, *Eimeria hagani*, or combinations thereof.

In some embodiments, the first and second compositions, and optionally the third composition, are admixed to form an admixed composition. The compositions may be mixed simultaneously or sequentially. The admixed composition may be further admixed with a feedstuff to form a feedstuff admixture.

The combination may be formulated for administration to an avian. In some embodiments, the combination is formulated for administration to chickens and turkey. In some other embodiments the combination is formulated for administration to animals other than chicken or turkeys.

The components of the admixed composition, the feedstuff admixture, or both, may be sized, concentrated, or diluted to facilitate admixing, facilitate administration to an animal, or combinations thereof. The combination may further comprise a vitamin, a trace mineral, a bulking agent, a carrier, a colorant, a taste enhancer, or any combination thereof, and in some embodiments the combination further comprises corn, soybean meal, wheat, barley, rye, canola, corn oil, limestone, salt, distillers dried grains with solubles (DDGS), dicalcium phosphate, sodium sesquicarbonate, methionine source, lysine source, L-threonine, choline, or any combination thereof.

Also disclosed herein is a method, comprising administering the composition and/or combinations described herein. In some embodiments, the method further comprises administering a third composition comprising a coccidiosis vaccine comprising oocysts derived from *Eimeria acervulina*, *Eimeria mivati*, *Eimeria maxima*, *Eimeria tenella*, *Eimeria mitis*, *Eimeria necatrix*, *Eimeria praecox*, *Eimeria brunetti*, *Eimeria hagani*, or combinations thereof. The first and second compositions, and the third composition and/or feedstuff if present, may be administered substantially simultaneously, or they may be administered sequentially, in any order.

Additionally disclosed is a method for making a combination, comprising providing a first composition comprising *Quillaja saponaria*, *Yucca schidigera*, or both; providing a second composition comprising an antimicrobial agent, an antibiotic, an anticoccidial agent, or a combination thereof; and mixing the first composition and the second composition. The method may further comprise admixing the combination with a feedstuff to form an admixed feedstuff. In some embodiments, the method further comprises formulating the first and/or second compositions for mixture with the feedstuff to provide a substantially homogeneous admixed feedstuff.

In certain embodiments, the method further comprises combining the first composition, the second composition, or both with a third composition comprising a vaccine.

The foregoing and other objects, features, and advantages of the present disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
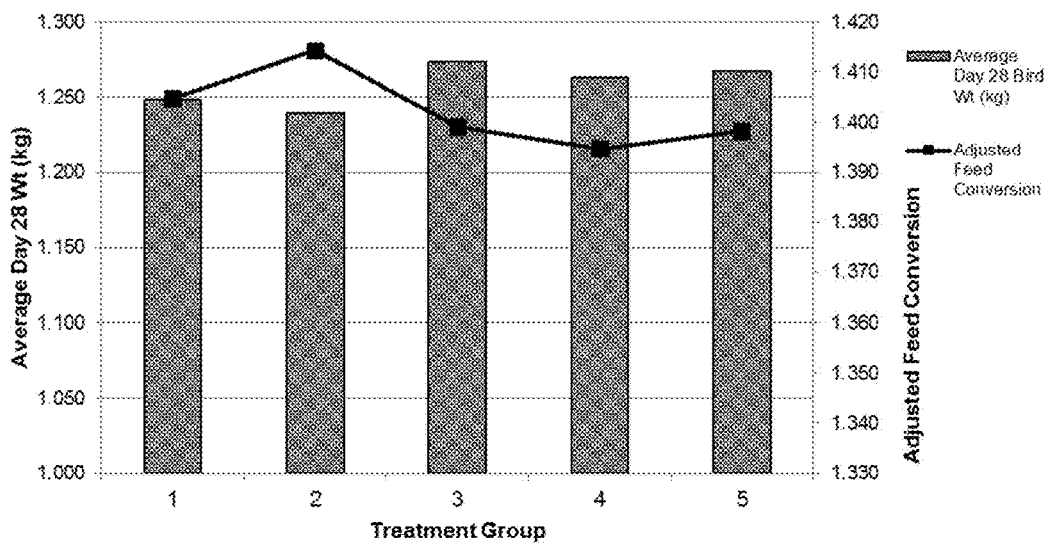
FIG. 1 is a graph of average weight (kg) and adjusted feed conversion of birds fed for 28 days with bird feed (Treatment Group 1), and bird feed comprising 125 ppm of an embodiment of a composition according to the present disclosure (composition embodiment (Treatment Group 2), 250 ppm of the same composition embodiment (Treatment Group 3), 500 ppm of the same composition embodiment (Treatment Group 4), and 2,500 ppm of the same composition embodiment (Treatment Group 5).

This disclosure concerns embodiments of a combination comprising *Quillaja* (e.g., *Quillaja saponaria*), *Yucca* (e.g., *Yucca schidigera*), an antimicrobial, an antibiotic, an anticoccidial agent, and/or a vaccine, such as a coccidiosis vaccine. Methods of administering the combination and/or composition embodiments disclosed herein are described, as are methods for treating and/or preventing certain diseases, such as coccidiosis, in animals using embodiments of the disclosed combination and/or composition embodiments.

I. Terms and Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Administering: Providing a combination, composition, or component disclosed herein by any suitable route to an animal. In some embodiments disclosed herein, administration can refer to oral administration.

Animal: This term includes, but is not limited to, humans, mammals, aquaculture species, and avian species. In some embodiments, this term can refer to mammals, aquaculture species, and avian species that are raised for human consumption or that are domesticated animals. Exemplary such animal species are provided herein.

Aquaculture Species: An animal that lives in salt or fresh water. Exemplary aquaculture species are disclosed herein.

Binding agent or binder: A material or substance that is used to hold or draw together other materials to form a cohesive unit. Examples include, but are not limited to, acacia, alginic acid, carboxymethylcellulose, sodium compressible sugar, ethylcellulose gelatin, liquid glucose, methylcellulose, povidone or pregelatinized starch.

Co-administration: Administering two or more combinations, compositions, or components simultaneously or sequentially in any order to a subject to provide overlapping periods of time in which the subject is experiencing effects, beneficial and/or deleterious, from each component. One or more of the components may be a therapeutic agent. Components may be combined into a single composition or dosage form, or they may be administered as separate components either simultaneously or sequentially in any order. When administered sequentially, the two or more components are administered within an effective period of time to provide overlapping periods of time in which the subject experiences effects from each component.

Combination: A combination comprises two or more compositions or components that are administered such that the effective time period of the first composition or component overlaps with the effective time period of the second and subsequent compositions or components. A combination may be a composition comprising the components, or it may be two or more individual components administered substantially simultaneously or sequentially in any order.

Excipient or carrier: A physiologically inert substance that is used as an additive in (or with) a combination, composition, or component as disclosed herein. As used herein, an excipient or carrier may be incorporated within particles of a combination, composition, or component, or it may be physically mixed with particles of a combination, composition, or component. An excipient or carrier can be used, for example, to dilute an active agent and/or to modify properties of a combination or composition. Examples of excipients and carriers include but are not limited to calcium carbonate, polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Feed conversion rate: A measure of the efficiency of an animal to convert feed mass into increased body mass; also known in the art as feed conversion ratio (which is expressed herein as a dimensionless number).

Feedstuff: Anything that may be consumed by an animal. The term "feedstuff" includes, but is not limited to, solid and liquid animal feeds (e.g., a feed ration), supplements (e.g., a mineral supplement), water, and feed additive carriers (e.g., molasses).

Saponin: A class of chemical compounds, one of many secondary metabolites found in natural sources, with saponins found in particular abundance in various plant species. More specifically, they are amphipathic glycosides grouped, in terms of structure, by their composition. In certain embodiments, saponin comprises one or more hydrophilic glycoside moieties combined with a lipophilic triterpene derivative.

Therapeutically Effective Amount or Effective Amount: A quantity or concentration of a specified compound or composition sufficient to achieve a desired effect in an animal being treated for a disorder. The therapeutically effective amount may depend at least in part on the species of animal being treated, the size of the animal, and/or the severity of the disorder.

II. Compositions and Combinations

Disclosed herein are embodiments of a combination of *Yucca* or *Quillaja*, more typically both, with an antimicrobial, an antibiotic, an anticoccidial agent, and/or a vaccine, such as a coccidiosis vaccine. In some embodiments, the disclosed combination embodiments may be administered prophylactically or therapeutically, to an animal to reduce the risk of the animal from developing particular diseases, such as coccidiosis, and/or to treat an animal suffering from a disease, such as coccidiosis. In some embodiments, the disclosed combinations also can improve the feed conversion rate of certain animals that are raised for human consumption, such as domestic fowl and livestock. In yet additional embodiments, the combinations and compositions can be used to improve animal health generally.

In some embodiments, the compositions and combinations disclosed herein can be used to significantly reduce the costs associated with animal production. In particular embodiments, the compositions and combinations can significantly reduce the costs associated with avian (e.g., domestic fowl) production as the compositions and combinations provide improvements in animal health and growth. Solely by way of example, a reduction of just one point in feed conversion ratio for 1 million chickens per week can translate into a cost/feed savings of nearly $750,000 per year. Some embodiments of the combinations disclosed herein can provide reductions of 5 or more points in feed conversion, thus illustrating their utility and superior activity.

Examples of *Yucca* that can be used in the disclosed combination include, but are not limited to, *Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca elata, Yucca endlichiana, Yucca faxoniana, Yucca filamentosa, Yucca filifera, Yucca flaccida, Yucca gigantean, Yucca glauca, Yucca gloriosa, Yucca grandiflora, Yucca harrimaniae, Yucca intermedia, Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis,* or *Yucca valida*. In certain disclosed embodiments the *Yucca* component is *Yucca schidigera*.

Examples of *Quillaja* that can be used in the disclosed combination include, but are not limited to, *Quillaja brasiliensis, Quillaja lanceolata, Quillaja lancifolia, Quillaja molinae, Quillaja petiolaris, Quillaja poeppigii, Quillaja saponaria, Quillaja sellowiana,* or *Quillaja smegmadermos*. In particular disclosed embodiments the *Quillaja* is *Quillaja saponaria*.

A person of ordinary skill in the art will appreciate that, as used herein, a plant name may refer to the plant as a whole, or to any part of the plant, such as the roots, stem or trunk, bark, leaves, flower, flower stems, or seeds or a combination thereof. These plant parts may be used fresh, or dried, and may be whole, pulverized, mashed, comminuted, or ground. The name may also refer to extracts from any part or parts of the plant, such as chemical extracts, or extracts obtained by pressing, or any other methods of concentrating or extracting oils or other extracts known to those in the art or that are hereafter discovered. Plant extracts may include compounds that are saponins, triterpenoids, polyphenols, antioxidants, resveratrol, or combinations thereof. A composition comprising *Yucca* and/or *Quillaja* can be used to make embodiments of the disclosed combination. Such compositions can also include carriers and binding agents suitable to formulate the *Yucca* and/or *Quillaja* for administration to animals. In some embodiments, the compositions are formulated for administration to mammals, avian, or aquaculture species. In certain independent embodiments, the composition can be a commercially available product, such as a composition comprising *Yucca schidigera* and *Quillaja saponaria*, which is sold under the trade name NUTRAFITO PLUS by Desert King International and/or MAGNI-PHI by Phibro Animal Health Corporation. Such composition embodiments can comprise 85% *Quillaja saponaria* and 15% *Yucca schidigera* or 90% *Quillaja saponaria* and 10% *Yucca schidigera*.

In some embodiments, the combination also comprises an antimicrobial, an antibiotic, an anticoccidial agent, a vaccine, and/or combinations of such components. The combination components can be administered in any order. In some embodiments, an antimicrobial, an antibiotic, an anticoccidial agent, and a vaccine can be administered to the animal prior to administration of *Yucca, Quillaja,* or a composition thereof. Alternatively, a vaccine can be administered to an animal, followed by administration of *Yucca, Quillaja,* or a composition thereof. In such embodiments, an antimicrobial, an antibiotic and/or an anticoccidial agent may be administered simultaneously with the *Yucca, Quillaja,* or composition thereof; or an antimicrobial, an antibiotic, and/or an anticoccidial agent may be administered before or after each of the *Yucca* and/or *Quillaja*. In an independent embodiment, an antimicrobial, an antibiotic and/or an anticoccidial agent need not be administered. In yet other independent embodiment, a vaccine need not be administered.

Suitable antimicrobials and/or antibiotics include, but are not limited to, Virginiamycin, Bacitracin MD, Zinc Bacitracin, Tylosin, Lincomycin, Flavomycin, Terramycin, Neo-Terramycin, or combinations thereof. In yet additional embodiments, the antimicrobial or antibiotic can be selected from penicillin, tetracycline, ceftiofur, florfenicol, tilmicosin, enrofloxacin, and tulathromycin, procaine penicillin, benzathine penicillin, ampicillin, amoxicillin, spectinomycin, dihydrostreptomycin, chlortetracycline, gentamicin, sulphadimidine, trimethoprim, oxytetracycline, erythromycin, norfloxacin and combinations thereof.

Suitable anticoccidial agents include, but are not limited to, ionophores and chemical anticoccidial products. Ionophores can include, but are not limited to, Monensin, Salinomycin, Lasalocid, Narasin, Maduramicin, Semduramicin, Laidlomycin, or combinations thereof.

Chemical anticoccidial products can include, but are not limited to, Nicarbazin, Maxiban, Diclazuril, Toltrazuril, Robenidine, Stenorol, Clopidol, Decoquinate, DOT (zoalene), Amprolium, or combinations thereof.

Suitable vaccines can be selected from live coccidiosis vaccines, such as COCCIVAC (e.g., a composition comprising live oocysts of *Eimeria acervulina, Eimeria mivati, Eimeria maxima, Eimeria mitis, Eimeria tenella, Eimeria necatrix, Eimeria praecox, Eimeria brunetti, Eimeria hagani*, or combinations thereof), LivaCox (a composition comprising 300-500 live sporulated oocysts of each attenuated line of *Eimeria acervulina, E. maxima* and *E. tenella* in a 1% w/v aqueous solution of Chloramine B), ParaCox (a composition comprising live sporulated oocysts derived from *E. acervulina* HP, *E. brunetti* HP, *E. maxima* CP, *E. maxima* MFP, *E mitis HP, E. necatrix* HP, *E. praecox* HP, *E. tenella* HP, and combinations thereof), Hatch Pack Cocci III (a composition comprising oocysts derived from *Eimeria acervulina, Eimeria maxima, Eimeria tenella*, or combinations thereof), INOVOCOX (a composition comprising oocysts derived from *Eimeria acervulina, Eimeria maxima, Eimeria tenella*, and a sodium chloride solution), IMMU-COX (a composition comprising live oocysts derived from *Eimeria acervulina, Eimeria maxima, Eimeria necatrix, Eimeria tenella*, and combinations thereof), Advent, or combinations thereof.

In yet additional embodiments, other vaccines can be utilized. For example, any vaccine suitable for use in any of the animals described herein can be used in the disclosed combinations and methods. In some embodiments, the vaccine can be selected based on the particular animal to receive the combination. In some embodiments, the vaccine can be selected based on the particular diseases to which a particular animal is susceptible. Solely by way of example, a vaccine administered to a ruminant can be selected from any vaccine suitable for preventing or treating sudden death (e.g., clostridial diseases, anthrax, and the like), respiratory diseases (e.g., infectious bovine rhinotracheitis, parainfluenza-3, bovine virus diarrhea, bovine respiratory syncytial virus, *Pasteurella, Haemophilus sommus*, and the like), reproductive diseases (IBR, BVD, brucellosis, vibriosis, lepto, trichomoniasis, and the like), scours (rota and corona virus, *E. coli*, and the like), pinkeye, hepatitis E virus, porcine endogenous retrovirus, swine influenza virus, porcine parvovirus, and the like. In some embodiments, vaccines can be selected from B ALPHA, BAR-GUARD-99, BAR-VAC, BIOMYCIN 200, BO-BAC-2X, BOVIKALC, CALIBER, CITADEL, CYDECTIN INJECTABLE, CYDECTIN POUR-ON, C & D ANTITOXIN, DIAQUE, DRY-CLOX, ENTERVENE-D, EXPRESS, EXPRESS FP, HETACIN-K, LYSIGIN, OCU-GUARD MB-1, POLYFLEX, PRESPONSE, PRISM 5, PYRAMID, PYRAMID, PRESPONSE SQ, QUATRACON-2X, SYNANTHIC, TODAY, TOMORROW, TRIANGLE, TRIVIB 5L, TRICH-GUARD, and the like. In yet additional embodiments, the vaccine can be selected from CIRCUMVENT PCV G2, CIRCUMVENT PCV-M G2, MAGESTIC 7, MAXIVAC, EXCELL 5.0, PROSYSTEM RCE, PROSYSTEM ROTA, TGE/ROTA, PROSYSTEM TREC, and the like.

The amount of antimicrobial or antibiotic used is within the amounts stated below but may depend on the particular antimicrobial or antibiotic used as will be understood by a person of ordinary skill in the art. In an independent embodiment, the amount of the antibiotic or antimicrobial that is used can be a therapeutically effective amount that is at an approved or authorized dosage level for a particular antibiotic. In some embodiments, the amount of antibiotic or antimicrobial used can range from greater than 0 ppm to 100,000 ppm, such as 0.25 ppm to 5,000 ppm, or 0.5 ppm to 2,500 ppm, or 0.75 ppm to 2,000 ppm, or 1 ppm to 1,500 ppm, or 5 ppm to 1,000 ppm, or 10 ppm to 500 ppm, or 25 ppm to 300 ppm. In yet additional embodiments, the amount of antibiotic or antimicrobial used can range from greater than 0 mg/kg of body weight to 100,000 mg/kg of body weight, such as 0.5 mg/kg to 2,500 mg/kg, or 1 mg/kg to 1,500 mg/kg, or 5 mg/kg to 1,000 mg/kg, or 10 mg/kg to 500 mg/kg m, or 25 mg/kg to 300 mg/kg, or 10-20 mg/kg.

In some embodiments, the amount of the antimicrobial or antibiotic that is included in the composition can range from at least 1 g/ton of feed to 230 g/ton of feed (or at least 1.1 ppm to 256 ppm), such as at least 1 g/ton of feed to 220 g/ton of feed (or at least 1.1 ppm to 243 ppm), at least 1 g/ton of feed to 100 g/ton of feed (or at least 1.1 ppm to 110 ppm), at least 1 g/ton of feed to 50 g/ton of feed (or at least 1.1 ppm to 55 ppm), or at least 1 g/ton of feed to 10 g/ton of feed (or at least 1.1 ppm to 11 ppm). Particular antimicrobials or antibiotics that can be used, and dosage amounts of such antimicrobials and antibiotics include, but are not limited to, the following: Virginiamycin in an amount ranging from 5 g/ton of feed to 25 g/ton of feed (or 5 ppm to 27 ppm, such as 22 ppm); Bacitracin MD in an amount ranging from 40 g/ton of feed to 220 g/ton of feed (or 44 ppm to 242 ppm, or 50 ppm to 250 ppm in some other embodiments); Zinc Bacitracin in an amount ranging from 40 g/ton of feed to 220 g/ton of feed (or 44 ppm to 242 ppm); Tylosin in an amount ranging from 1 g/ton of feed to 1000 g/ton of feed (or 1 ppm to 1100 ppm); Lincomycin in an amount ranging from 1 g/ton of feed to 5 g/ton of feed (or 1 ppm to 6 ppm); Flavomycin in an amount ranging from 1 g/ton of feed to 5 g/ton of feed (or 1 ppm to 6 ppm); or combinations thereof.

The amount of anticoccidial agent, as will be understood by a person of ordinary skill in the art (e.g., a veterinarian), can be selected depending on the particular anticoccidial agent used. In some embodiments, the amount of anticoccidial agent used can be a therapeutically effective amount for a particular animal species. In some embodiments, the amount of anticoccidial agent used can range from greater than 0 ppm to 100,000 ppm, such as 0.25 ppm to 5,000 ppm, or 0.5 ppm to 2,500 ppm, or 0.75 ppm to 2,000 ppm, or 1 ppm to 1,500 ppm, or 5 ppm to 1,000 ppm, or 10 ppm to 500 ppm, or 25 ppm to 300 ppm. In yet additional embodiments, the amount of antibiotic or antimicrobial used can range from greater than 0 mg/kg of body weight to 100,000 mg/kg of body weight, such as 0.5 mg/kg to 2,500 mg/kg, or 1 mg/kg to 1,500 mg/kg, or 5 mg/kg to 1,000 mg/kg, or 10 mg/kg to 500 mg/kg m, or 25 mg/kg to 300 mg/kg, or 10-20 mg/kg.

In some embodiments, the amount of the anticoccidial agent that is included in the composition can range from at least 1 g/ton of feed to 250 g/ton of feed (or at least 1 ppm to 275 ppm), such as at least 1 g/ton of feed to 200 g/ton of feed (or at least 1 ppm to 242 ppm), or at least 1 g/ton of feed to 150 g/ton of feed (or at least 1 ppm to 165 ppm), at least 1 g/ton of feed to 100 g/ton of feed (or at least 1 ppm to 110 ppm), or at least 1 g/ton of feed to 50 g/ton of feed (or at least 1 ppm to 55 ppm). Particular anticoccidial agents that can be used, and dosage amounts of such anticoccidial agents include, but are not limited to, the following: Monensin in an amount ranging from 35 g/ton of feed to 110 g/ton of feed (or 38 ppm to 121 ppm); Salinomycin in an amount ranging from 25 g/ton of feed to 90 g/ton of feed (or 27 ppm to 99 ppm); Lasalocid in an amount ranging from 35 g/ton of feed to 113 g/ton of feed (or 38 ppm to 125 ppm); Narasin in an amount ranging from 35 g/ton of feed to 72 g/ton of feed (or 38 ppm to 79 ppm); Maduramicin in amount ranging from 2 g/ton of feed to 7 g/ton of feed (or 2 ppm to 8 ppm); Semduramicin in an amount ranging from 12 g/ton of feed to 23 g/ton of feed (or 13 ppm to 25 ppm); Nicarbazin in an amount ranging from 60 g/ton of feed to 113 g/ton of feed (or 66 ppm to 125 ppm); Maxiban in an amount ranging from 40 g/ton of feed to 90 g/ton of feed (or 44 ppm to 99 ppm); Diclazuril in an amount ranging from 0.5 g/ton of feed to 10 g/ton of feed (or 0.6 ppm to 11 ppm); Toltrazuril in an amount ranging from 1 g/ton of feed to 10 g/ton of feed (or 1 ppm to 11 ppm); Robenidine in an amount ranging from 20 g/ton of feed to 60 g/ton of feed (or 22 ppm to 66 ppm); Stenorol in an amount ranging from 1.5 g/ton of feed to 15 g/ton of feed (or 1.5 ppm to 17 ppm); Clopidol in an amount ranging from 90 g/ton of feed to 227 g/ton of feed (or 99 ppm to 250 ppm); Decoquinate in an amount ranging from 18 g/ton of feed to 27 g/ton of feed (or 19 ppm to 29 ppm); Zoalene in an amount ranging from 25 g/ton of feed to 113 g/ton of feed (or 28 ppm to 125 ppm); Amprolium in an amount ranging from 20 g/ton of feed to 227 g/ton of feed (or 22 ppm to 250 ppm).

The amount of vaccine administered to the animal in combination with any of the components described herein can depend on the type of animal to which the vaccine is administered. In some embodiments, the amount of vaccine used is a therapeutically effective amount ranging from greater than 0 mL/animal to 1,000 mL/animal, or 0.25 mL/animal to 500 mL/animal, or 0.5 mL/animal to 150 mL/animal, or 1 mL/animal to 100 mL/animal, or 2 mL/animal to 50 mL/animal, or 3 mL/animal to 25 mL/animal, or 5 mL/animal to 15 mL/animal.

In some embodiments the composition and/or combination further comprises a vitamin, a trace mineral, a bulking agent, a carrier, a colorant, a taste enhancer, or any combination thereof. In other embodiments the combination further comprises corn, soybean meal, wheat, barley, rye, canola, corn oil, limestone, salt, distillers dried grains with solubles (DDGS), dicalcium phosphate, sodium sesquicarbonate, methionine source, lysine source, L-threonine, choline, or any combination thereof.

In some embodiments, the combination can be admixed with a feedstuff. The combination can be formulated to form a homogeneous mixture with the feedstuff, such as by crushing, crumbling, grinding or otherwise sizing the combination. Alternatively, the combination may be formulated as a solution, suspension, or slurry with the feedstuff, or separately and then added to the feedstuff. In embodiments where the combination comprises two or more compositions, the compositions may be formulated separately or substantially together. Any of the compositions disclosed herein also can be admixed with the feedstuff. In some embodiments, a composition and the feedstuff may be admixed sequentially, in any order, or substantially simultaneously.

In some embodiments the amount of *Yucca* administered to an animal can range from 0 to greater than 10 ounces per ton of feedstuff, typically greater than 0 ounces up to at least 10 ounces per ton of feedstuff, such as from 1 ounce to 9 ounces, or 1 ounce to 8 ounces, or 1 ounce to 7 ounces. The amount of *Quillaja* administered to an animal can range from 0 to greater than 10 ounces per ton of feedstuff, typically greater than 0 ounces up to at least 10 ounces per ton of feedstuff, such as from 1 ounce to 9 ounces, or 1 ounce to 8 ounces, or 1 ounce to 7 ounces. In certain embodiments, both *Yucca* and *Quillaja* are administered, and the combined amount administered is from greater than 0 ounces to greater than 10 ounces per ton of feedstuff, such as from 1 ounce to 9 ounces, or 1 ounce to 8 ounces, or 2 ounces to 7 ounces. In an independent embodiment, *Yucca schidigera* and *Quillaja saponaria* can be administered together in an amount ranging from 2 ounces to 8 ounces per ton of feedstuff.

In some embodiments, the amount of compositions comprising *Yucca, Quillaja*, or a combination thereof that are administered to animals can be an amount sufficient to promote animal health, reduce susceptibility to disease, and/or improve feed conversion performance in animals. The amount of the composition comprising *Yucca, Quillaja*, or a combination thereof that can be administered to animals can be measured based on the concentration of the composition per unit of feed, such as in ppm of feed. In such embodiments, the amount of the composition comprising *Yucca, Quillaja*, or a combination thereof can range from greater than 0 ppm to 100,000 ppm, such as greater than 0 ppm to 5,000 ppm, such as 50 ppm to 3,000, or 100 ppm to 2,500 ppm, or 200 ppm to 2,500 ppm, or 250 ppm to 600 ppm, or 150 ppm to 600 ppm, or 200 ppm to 400 ppm, or 250 ppm to 300 ppm.

In some embodiments, the amount of the composition comprising *Yucca, Quillaja*, or a combination thereof that can be administered to animals can be measured based on the amount of the composition per unit body weight of an animal, such as mg/kg BW/day and/or g/kg BW/day, wherein "BW" refers to body weight. In some embodiments, the amount of the composition comprising *Yucca, Quillaja*, or a combination thereof that is administered can range from greater than 0 mg/kg BW/day to 1000 mg/kg BW/day, such as 10 mg/kg BW/day to 500 mg/kg BW/day, or 20 mg/kg BW/day to 250 mg/kg BW/day, or 30 mg/kg BW/day to 200 mg/kg BW/day, or 40 mg/kg BW/day to 100 mg/kg BW/day. In yet additional embodiments, the amount of the composition comprising *Yucca, Quillaja*, or a combination thereof that can be administered to an animal can be measured based on the amount of the composition per animal per day, such as mg/head/day and/or g/head/day. In some embodiments, the amount of the composition comprising *Yucca, Quillaja*, or a combination thereof that is administered can range from greater than 0 mg/head/day to 100 g/head/day, such as 0.25 mg/head/day to 100 g/head/day, or 1 mg/head/day to 75 g/head/day, or 10 mg/head/day to 50 g/head/day, or 50 mg/head/day to 25 g/head/day.

In an independent embodiment, a composition comprising *Yucca schidigera* and *Quillaja saponaria* can be administered using at least 200 ppm to 5,000 ppm, such as 200 ppm to 2,500 ppm, 200 ppm to 500 ppm, 200 ppm to 300 ppm, 225 ppm to 275 ppm, or 230 ppm to 260 ppm. An exemplary embodiment of the disclosed combination comprises 200 ppm, 250 ppm, or 300 ppm of a composition comprising *Yucca schidigera* and *Quillaja saponaria*.

In some embodiments, the ratio of *Quillaja saponaria* and *Yucca schidigera* can range from 70:30 (*Quillaja saponaria:Yucca schidigera*) to 90:10 (*Quillaja saponaria:Yucca schidigera*). In an independent embodiment, the ratio of *Quillaja saponaria* and *Yucca schidigera* can be 85:15.

III. Methods of Use

Disclosed herein are embodiments of a method of using the compositions and combinations disclosed herein. Certain method embodiments can concern administering the disclosed compositions and/or combinations to an animal to treat and/or prevent certain diseases, such as coccidiosis. In some disclosed embodiments, administering the composition and/or combination result in reducing negative effects associated with diseases, such as coccidiosis, in animals, such as, but not limited to, poor body weights, feed conversion rates, oocyst production, and/or lesion scores. In some embodiments, the animal can be an animal raised for human consumption or a domesticated animal. Examples of animals that can be administered the compositions and combinations disclosed herein include, but are not limited to, mammals, such as livestock (e.g., feed or dairy cattle) or pigs; avian, such as domestic fowl (e.g., laying hens, chicken, turkey, goose, duck, cornish game hen, quail, partridge, pheasant, guinea-fowl, ostrich, emu, swan, or pigeon); aquaculture species, such as fish (e.g., salmon, trout, cod, halibut, snapper, herring, catfish, and the like), crustaceans (e.g., lobster, shrimp, prawns, crabs, krill, crayfish, barnacles, copepods, and the like), or molluscs (e.g., abalone, conchs, rock snails, whelk, clams, oysters, mussels, cockles, and the like). In other embodiments, the animal can be a domestic animal, such as a dog, cat, fish, or rabbit. In some other embodiments, the animal can be a ruminant species, such as a sheep, goat, cow, deer, bison, buffalo, or llama. In yet other embodiments, the animal can be an ungulate, such as a horse, donkey, or pig.

In some embodiments, the method comprises administering a combination comprising a first composition and a second composition. The first composition can comprise Yucca, Quillaja, or a combination thereof. In some embodiments, the first composition comprises Yucca schidigera, Quillaja saponaria, or a combination thereof. In some embodiments, the method can comprise administering an amount of a composition comprising Yucca, Quillaja, or a combination thereof to an animal in amounts ranging from greater than 0 ppm to 100,000 ppm, such as 0 ppm to 5,000 ppm, or 10 ppm to 3,000 ppm, or 25 ppm to 4,000 ppm, or 50 ppm to 3,000, or 100 ppm to 2,500 ppm, or 200 ppm to 2,500 ppm, or 250 ppm to 600 ppm, or 250 ppm to 300 ppm.

In some embodiments, the method can comprise administering an amount of a composition comprising Yucca, Quillaja, or a combination thereof ranging from greater than 0 mg/head/day to 100 g/head/day, such as 0.25 mg/head/day to 100 g/head/day, or 1 mg/head/day to 75 g/head/day, or 10 mg/head/day to 50 g/head/day, or 50 mg/head/day to 25 g/head/day.

In some exemplary embodiments of the disclosed methods, the first composition comprises Yucca schidigera, Quillaja saponaria and the composition is administered to avian. In such embodiments, the amount of the first composition can range from greater than 150 ppm to 5,000 ppm, such as at least 200 ppm to 5,000 ppm, such as at least 200 ppm to 500 ppm, or 250 ppm to 300 ppm of a composition comprising Yucca schidigera, Quillaja saponaria, or a combination thereof.

In some embodiments, the methods can comprise administering the compositions disclosed herein to animals other than chickens and turkeys. In some embodiments concerning administering a first composition comprising Yucca schidigera and Quillaja saponaria to animals other than chickens or turkeys, the amount of the first composition that is administered can range from greater than 0 ppm to 100,000 ppm, such as greater than 0 ppm to 5,000 ppm, or 50 ppm to 3,000, or 100 ppm to 2,500 ppm, or 200 ppm to 2,500 ppm, or 250 ppm to 600 ppm, or 250 ppm to 300 ppm.

In some embodiments, the method can comprise administering the compositions or combinations to ruminants or ungulates. Such embodiments can comprise administering a disclosed composition or combination embodiment to a livestock animal in an amount suitable to improve animal health or increase milk production. In some embodiments, a composition comprising Yucca, Quillaja, or a combination thereof can be administered to a ruminant or ungulate in an amount ranging from greater than 0 ppm to 100,000 ppm, such as greater than 0 ppm to 5,000 ppm, such as 50 ppm to 3,000, or 100 ppm to 2,500 ppm, or 200 ppm to 2,500 ppm, or 250 ppm to 600 ppm, or 150 ppm to 600 ppm, or 200 ppm to 400 ppm, or 250 ppm to 300 ppm. In exemplary embodiments, the amount of the composition comprising Yucca, Quillaja, or a combination thereof that is administered to certain ruminants, such as swine, ranges from 50 ppm to 600 ppm. In yet additional embodiments, a composition comprising Yucca, Quillaja, or a combination thereof can be administered to a ruminant or ungulate in an amount ranging from greater than 0 mg/head/day to 100 g/head/day, such as 0.25 mg/head/day to 100 g/head/day, or 1 mg/head/day to 75 g/head/day, or 10 mg/head/day to 50 g/head/day, or 50 mg/head/day to 25 g/head/day.

In yet additional embodiments, the composition comprising Yucca, Quillaja, or a combination thereof can be administered to aquaculture species. In such embodiments, the methods can comprise providing the aquaculture species an amount of the composition that ranges from greater than 0 ppm to 100,000 ppm, such as 100 ppm to 50,000 ppm, or 200 ppm to 25,000 ppm, or 300 ppm to 15,000 ppm, or 400 ppm to 5,000 ppm, or 500 ppm to 1,000 ppm. In some exemplary embodiments, the amount ranges from 300 ppm to 2,000 ppm, such as 300 ppm to 500 ppm.

In an independent embodiment, the method can comprise administering a composition comprising Yucca, Quillaja, or a combination thereof wherein the amount of the composition that is administered ranges from at least 200 ppm to 5,000 ppm, such as 200 ppm to 2,500 ppm, 200 ppm to 500 ppm, 200 ppm to 300 ppm, 225 ppm to 275 ppm, or 230 ppm to 260 ppm. An exemplary embodiment of the disclosed combination comprises 200 ppm or 250 ppm of a composition comprising Yucca schidigera and Quillaja saponaria.

In some embodiments, administration of a composition comprising Yucca and Quillaja, such as Yucca schidigera and Quillaja saponaria, provides a health benefit to an animal compared to an animal that is not administered the composition. The composition may be administered alone, or in combination with an antimicrobial, an antibiotic, an anticoccidial agent, a vaccine, or a combination thereof, as disclosed herein. In some embodiments, the composition is administered in the amounts disclosed herein. The health benefit may include, but is not limited to, an anticoccidial effect, as determined by a reduction in the number of coccidian oocysts detected in fecal samples; a reduction in the number of Necrotic Enteritis lesions caused by Clostridium perfringens; a reduction in the impact of field infections and trophozoite burden caused by Cochlosoma anatis infections; and/or a beneficial effect on the microbiome of the animal. The beneficial effect on the microbiome of the animal, such as the gut bacterial community, may include, but is not limited to, a decrease in Clostridium species, such as Clostridiaceae; a decrease in cyanobacterial sequences; a decrease in Enterococcus species, including Enterococcus cecorum; a decrease in E. coli; a decrease in Corynebacterium species; a decrease in Staphylococcus species; a decrease in Streptococcus species; an increase in Lactobacillus species, such as, Lactobacillus reuteri; an increase in segmented filamentous bacteria (Candidatus Arthromitus); an increase in Peptostreptococcaceae, including butyrate producing bacteria that have been shown to be positively correlated with improved gut health; or any combination thereof. The health benefit may occur at any time during the time period during which the composition is administered. In some embodiments, the composition is administered from the day of age, and the health benefit may occur at any time from the day of age, such as from the day of age to day of harvest.

In certain method embodiments, the second composition can comprise an antimicrobial, an antibiotic, an anticoccidial agent, a vaccine, or a combination thereof. In some embodiments, the second composition comprises Virginiamycin, Salinomycin, or a combination thereof. The amount of the antibiotic, antimicrobial, anticoccidial agent, or vaccine in the second composition can range from any of the amounts disclosed for such components provided herein. In some embodiments, the amount of the antibiotic, antimicrobial, anticoccidial agent, or vaccine can range from greater than 0 ppm to 500 ppm, such as 10 ppm to 100 ppm, or 10 ppm to 70 ppm. In some embodiments, the amount ranges from at least 10 ppm to 30 ppm Virginiamycin and/or at least 25 ppm to 90 ppm Salinomycin, such as 20 ppm to 80 ppm, 20 ppm to 70 ppm, 20 ppm to 60 ppm, or 20 ppm to 50 ppm. Exemplary amounts in certain working embodiments include, but are not limited to, 22 ppm Virginiamycin and/or 50 ppm to 70 ppm, such as 66 ppm Salinomycin.

Method embodiments disclosed herein also can comprise administering the combination comprising the first composition and the second composition in combination with a feedstuff. For example, the combination of the first composition and the second composition can be administered in combination with an amount of feedstuff suitable for obtaining an animal having a weight suitable for that particular species. Solely by way of example, some embodiments can comprise administering the first composition and the second composition in combination with 7 lbs to 10 lbs of a feedstuff to a chicken. Any suitable dosage of the combination comprising the first composition, second composition, and the feedstuff may be used. In some embodiments, the amount of the feedstuff that is provided to the animal can be varied according to their food intake needs as growth occurs.

In some embodiments, the combination can comprise a first composition comprising *Yucca schidigera* and *Quillaja saponaria*, a second composition comprising an antimicrobial agent and/or an antibiotic, and a third composition comprising a vaccine. A feedstuff also may be administered in such embodiments. The combination of the first, second, and/or third compositions that is administered can be admixed with a feedstuff prior to administration to the animal, or the feedstuff may be administered before or after the combination of the first, second, and/or third compositions. These embodiments are not intended to limit the order of administration, as any suitable order of administration can be selected.

The combination and/or composition embodiments disclosed herein can be administered using any suitable technique. In some embodiments, the combination and/or the composition is orally administered by actively introducing the combination into the animal's mouth, or orally administered by allowing the bird to ingest the combination and/or composition on its own. The combination and/or composition may be administered to the animal during any stage of its lifecycle in which they consume food. In some embodiments, the animal is an avian, such as a domestic fowl and the combination or composition disclosed herein is administered after hatching (or "day of age"), or at any stage thereafter, such as day of age to 42 days after birth, or 18 days after birth to 35 days after birth. In some embodiments, the combination or composition can be fed to 18 day-old broiler chickens, and thereafter until harvest, typically at 8 weeks. In some embodiments, the combination or composition can be fed to an animal that is raised for human consumption from day of age to day of death, or from day of age to a time period prior to death.

Method embodiments disclosed herein improve an animal's feed conversion rate, such as by reducing the animal's feed conversion rate value, relative to animals that are fed a standard diet (e.g., a feedstuff). In an independent embodiment, the method described herein can be used to improve an animal's feed conversion rate relative to animals that are solely fed a feedstuff in combination with amounts of a composition comprising *Yucca schidigera* and *Quillaja saponaria* ranging from 100 ppm to 150 ppm. In some embodiments, the animal is an animal raised for human consumption, such as a domestic fowl and/or livestock. A feed conversion rate (feed conversion ratio) is a measure of an animal's efficiency in converting feed mass into increased body mass. In embodiments wherein the combination or composition is administered to an avian, such as a domestic fowl, an avian (e.g., domestic fowl) exhibiting a low feed conversion rate (e.g., at least one to less than 2, such as greater than 1 to 1.8, 1.7, 1.6, 1.5, 1.4, or lower) is considered efficient, as it requires less feed to reach a desired weight. In some embodiments, a low feed conversion rate for pigs can be 1 to 3, such as 1 to 3, or 2 to 3. In some embodiments, a low feed conversion rate for cattle can be 5 to 8, such as 6 to 8, or 7 to 8. In some embodiments the feed conversion rate of an avian, such as a domestic fowl, can be enhanced by 0.5% to greater than 20%, such as 2% to 10%, and in certain independent embodiments, by 3% to 5%. Exemplary embodiments disclosed herein provide a feed conversion rate enhancement of broiler meat-type chickens of 4-5%.

Some method embodiments disclosed herein also comprise reducing the concentration of oocysts in feces of animals, thereby reducing the incidence of coccidiosis in such animals, by administering an embodiment of the combination and/or composition. In some embodiments, the method can comprise administering a combination or composition disclosed herein to an animal and then evaluating the number of oocysts produced by the animal in comparison to an animal that has not been administered the combination and/or composition. In some embodiments, the number of oocysts can be reduced by a factor of 2, 3, 4, 5, or 6, or by about 20% to 80%, such as 20% to 70%, 20% to 60%, or 20% to 50%. In certain vaccinated animals, such as domestic fowl, the number of oocysts can range from 10,000 to 20,000 oocysts per gram of feces, which can be reduced by a factor of four or 25%.

IV. Working Examples

The subject matter disclosed herein is further understood by reference to the following examples, which are intended to be purely exemplary of certain working embodiments of the present disclosure. The present disclosure is not limited in scope by the exemplified embodiments, which are intended as illustrations of single aspects of the claimed invention only. Any methods that are functionally equivalent are within the scope of the claimed invention. Various modifications of the presently disclosed subject matter, in addition to those described herein, will become apparent to those of ordinary skill in the art from the foregoing description and accompanying figures. Such modifications fall within the scope of the appended claims.

Example 1

In this example, the disclosed combination was administered to broiler chickens to determine doses in which the disclosed combination can be administered without negatively affecting feed intake and at what level of administration toxicity occurs.

Approximately 50 broiler chickens were kept in pens (8 pens in total, with 50 birds per pen) and fed a composition comprising *Yucca schidigera* and *Quillaja saponaria* (referred to in Examples 1-5 herein as "the composition" or the "*Yucca schidigera* and *Quillaja saponaria* composition") at different doses. The doses used in this particular example included feed with 0 ppm of the composition, 125 ppm of the composition, 250 ppm of the composition, 500 ppm of the composition, and 2,500 ppm of the composition. No disease challenge was administered to the pen. Performance measurements were conducted, food intake was assessed, and death incidence measured. The results obtained from this particular embodiment are illustrated graphically in FIGS. 1-3.

Figure 2:
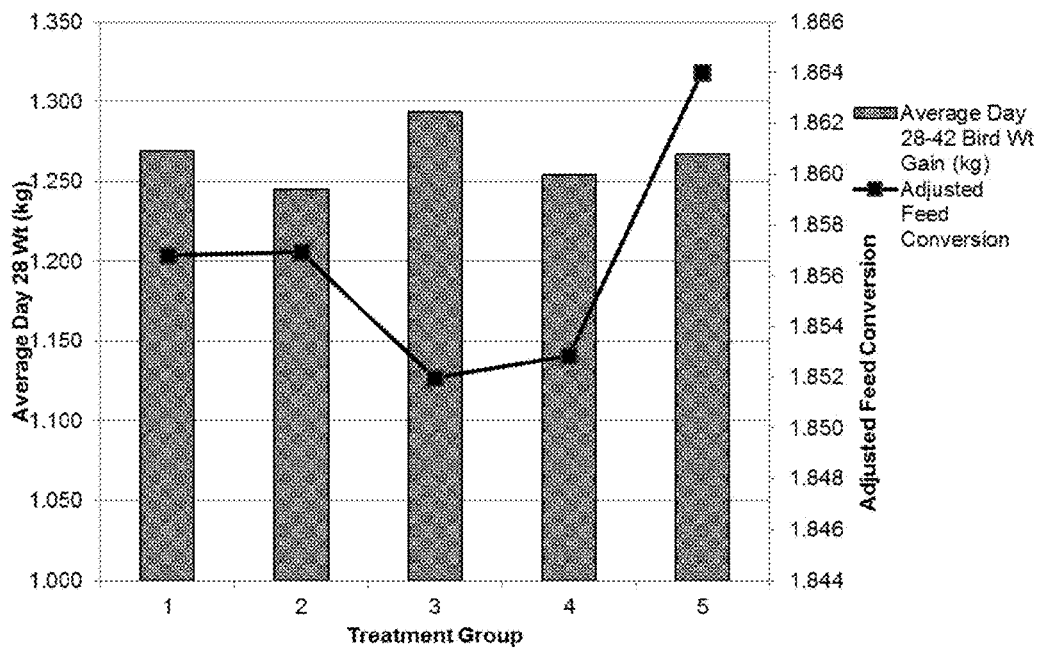
FIG. 2 is a graph of average weight (kg) and adjusted feed conversion obtained from birds fed for 28-42 days with bird feed (Treatment Group 1), and bird feed comprising 125 ppm of a composition embodiment (Treatment Group 2), 250 ppm of a composition embodiment (Treatment Group 3), 500 ppm of a composition embodiment (Treatment Group 4), and 2,500 ppm of a composition embodiment (Treatment Group 5).
Figure 3:
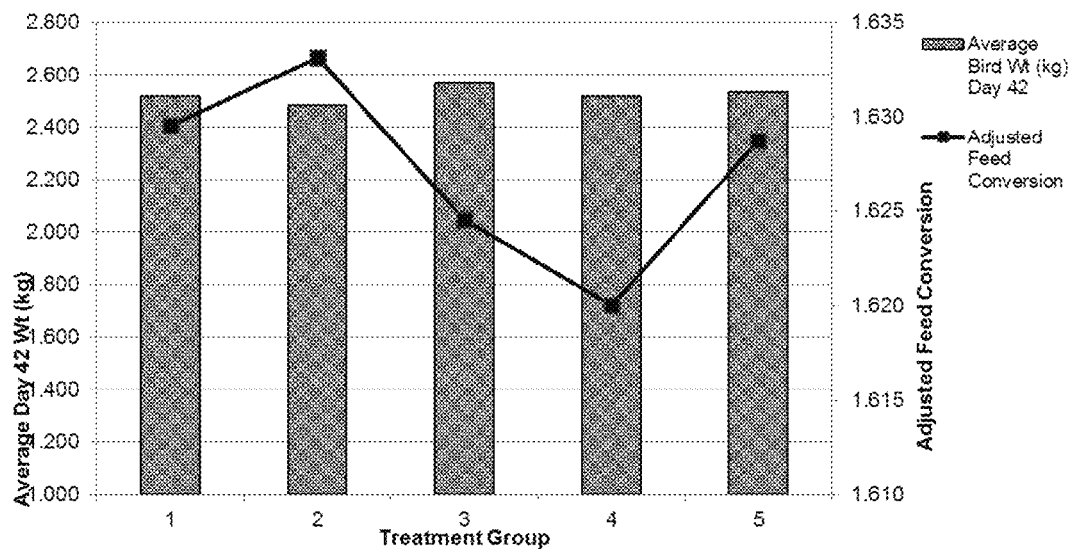
FIG. 3 is a graph of average weight (kg) and adjusted feed conversion obtained from birds fed for 42 days with bird feed (Treatment Group 1), and bird feed comprising 125 ppm of a composition embodiment (Treatment Group 2), 250 ppm of a composition embodiment (Treatment Group 3), 500 ppm of a composition embodiment (Treatment Group 4), and 2,500 ppm of a composition embodiment (Treatment Group 5).
Figure 4:
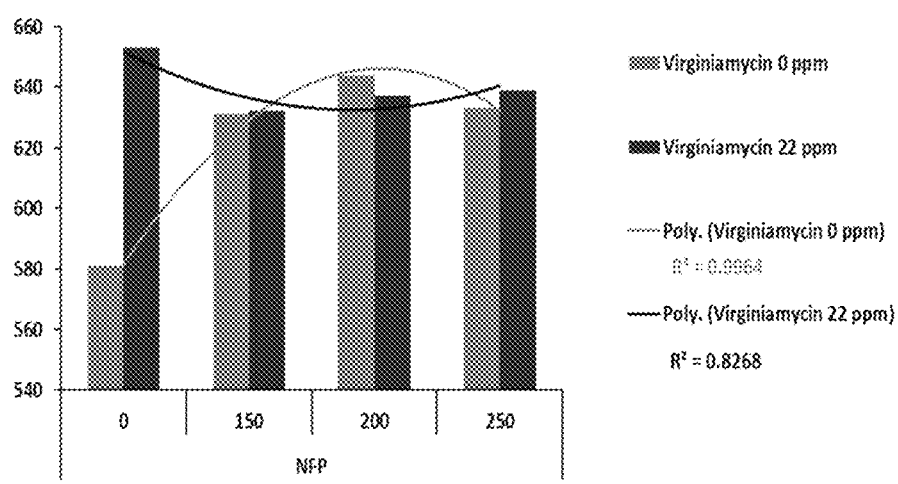
FIG. 4 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 18 days of feeding.
Figure 5:
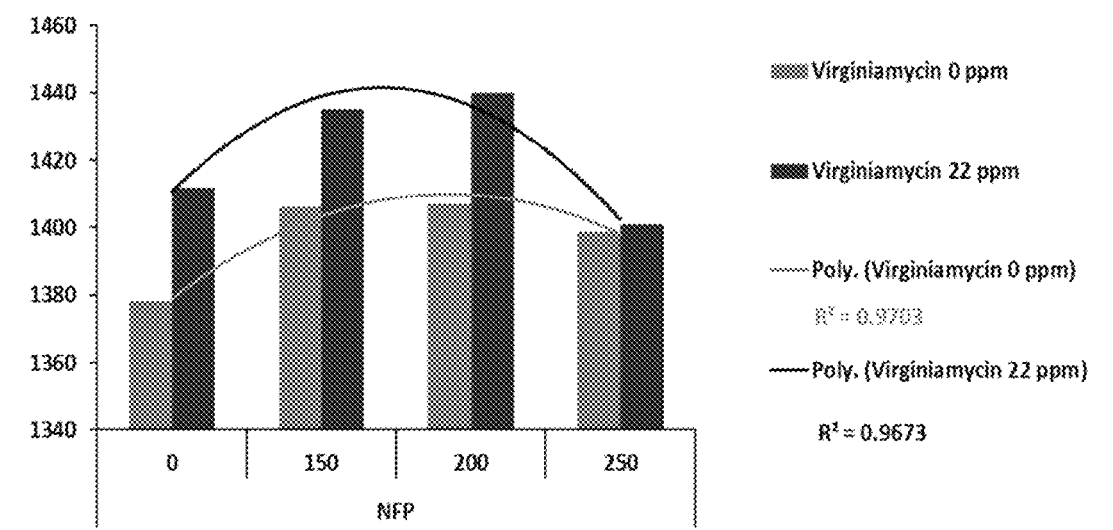
FIG. 5 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 18-32 days of feeding.
Figure 6:
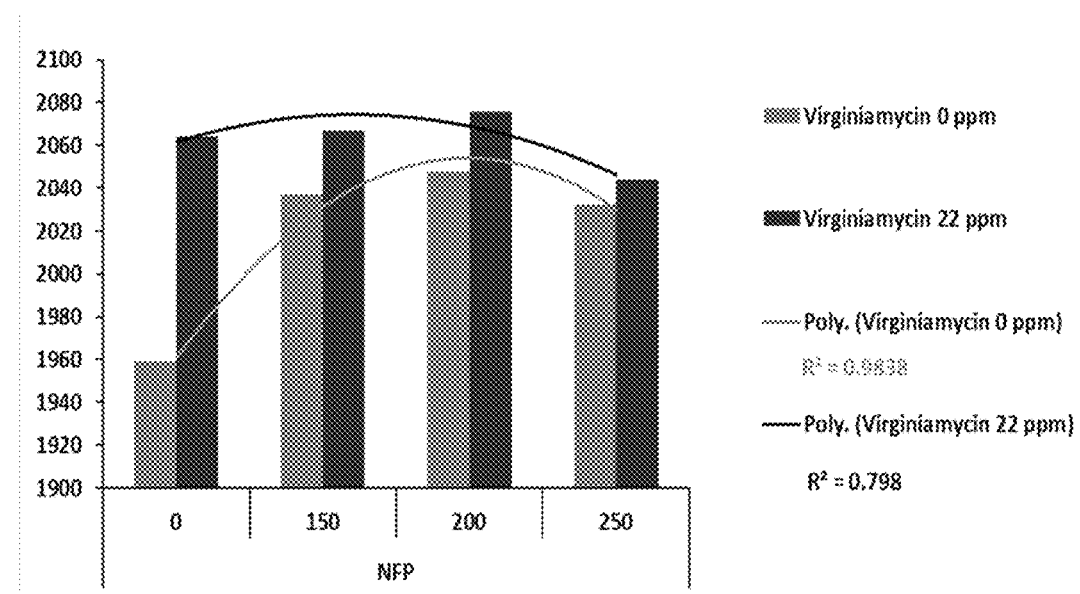
FIG. 6 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 0-32 days of feeding.
Figure 7:
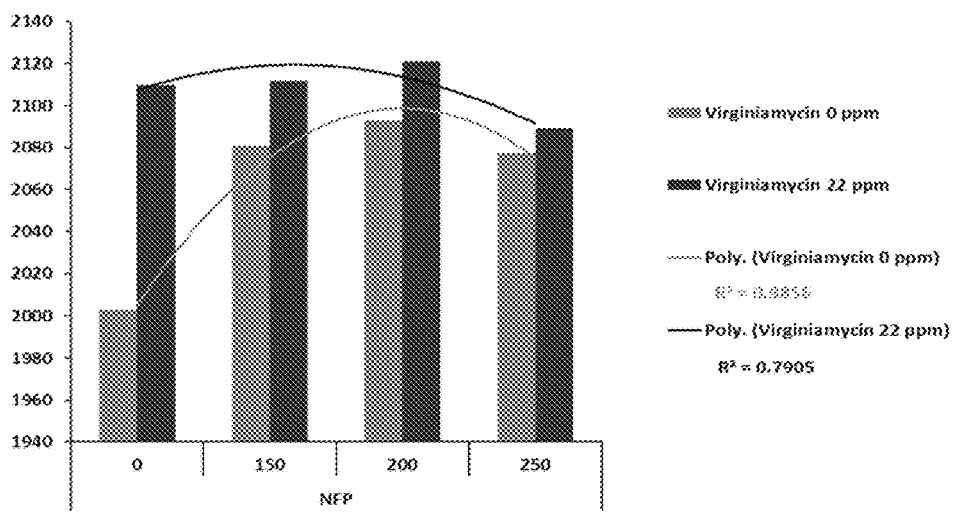
FIG. 7 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 32 days of feeding.
Figure 8:
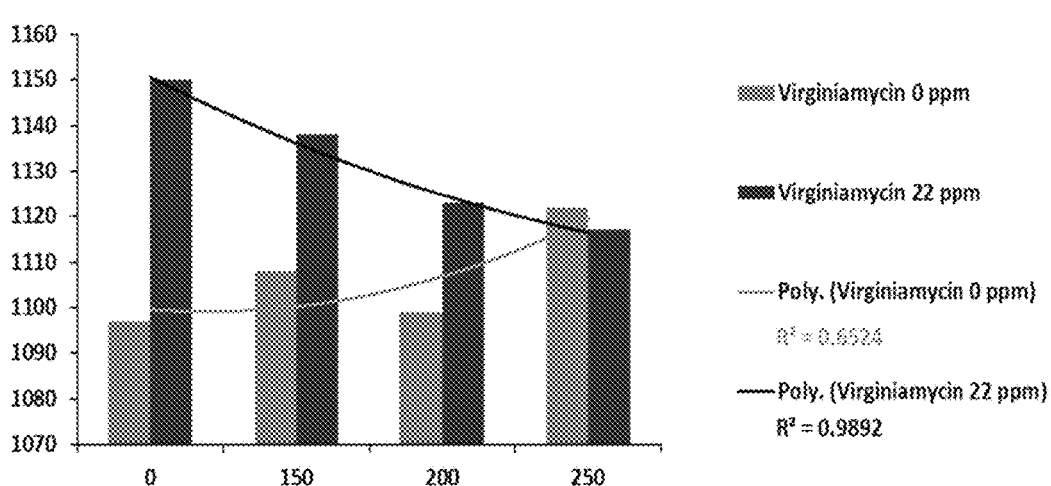
FIG. 8 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 32-42 days of feeding.

As illustrated in FIG. 1, performance (in the form of average weight and adjusted feed conversion) was first measured after 28 days, with doses of 250 ppm and 500 ppm providing better feed conversion than 0 ppm and/or 125 ppm doses. FIG. 2 illustrates results obtained from days 28-42 of the study, such results again indicating lower feed conversion numbers for doses of 250 ppm and 500 ppm than that achieved from feeding the birds feed only and/or feed including 125 ppm of the composition. FIG. 3 illustrates results obtained on the final day of the study (day 42); similar results were obtained. Accordingly, this particular embodiment establishes that there are no adverse effects in feed intake, feed conversion or body weights in birds that ingested up to 2500 ppm. The results also indicate that higher doses of the composition (e.g., about 200 ppm to about 500 ppm) than that typically suggested amount in the art (i.e., 125 or 150 ppm) can be administered to the animal without adverse effects.

Example 2

In this example, the live performance of male broiler chickens during a standard diet program with and without an embodiment of the disclosed combination was determined. In this embodiment, the combination comprised Virginiamycin and different levels of the composition, particularly 0 ppm, 150 ppm, 200 ppm, and 250 ppm, and further comprising Avatec 90. A disease challenge was presented in each pen by adding coccidial contaminated litter to the pen.

Figure 9:
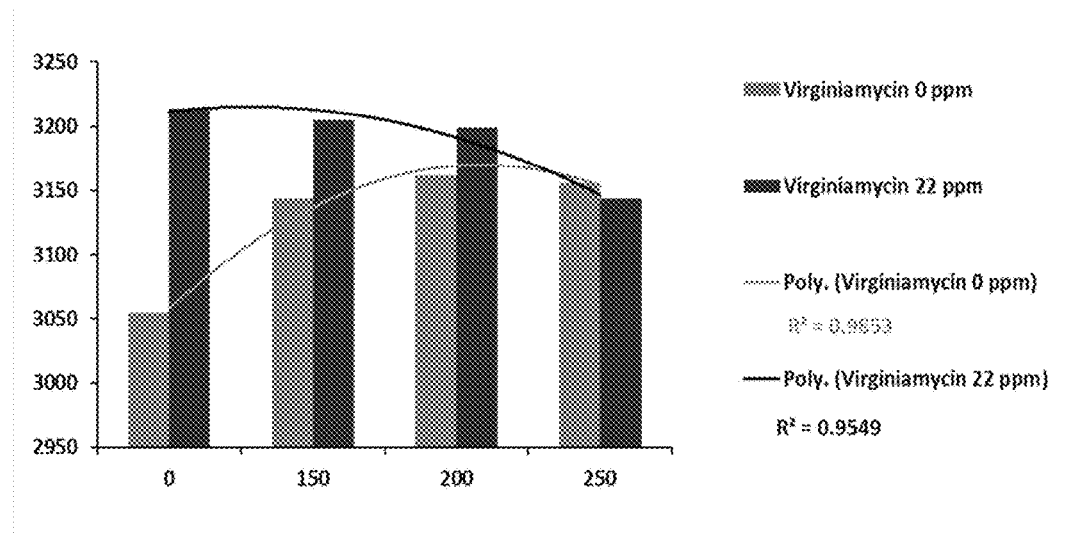
FIG. 9 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 0-42 days of feeding.
Figure 10:
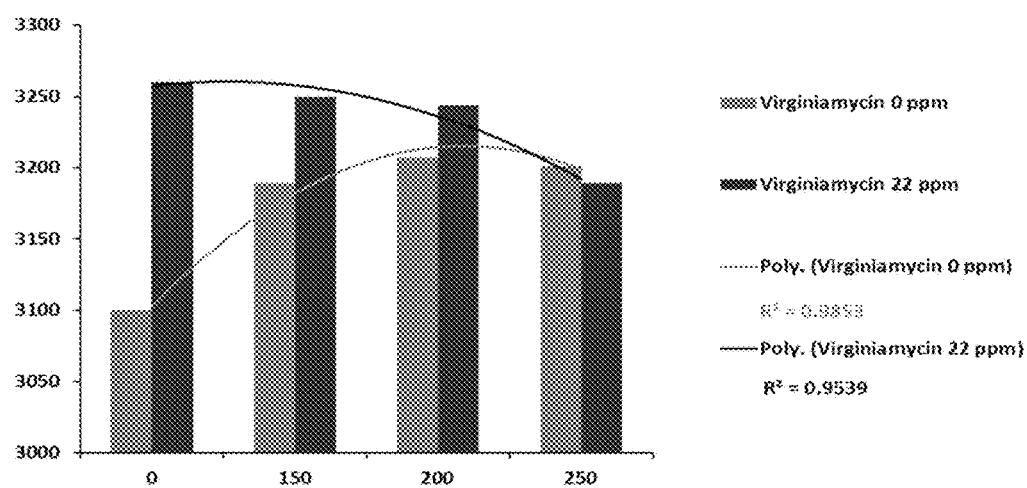
FIG. 10 is a graph of bird weight gain (kg) illustrating results obtained from feeding birds various different treatments of a composition embodiment (0 ppm, 150 ppm, 200 ppm, and 250 ppm) and Virginiamycin (0 ppm and 22 ppm), with the graph providing results obtained after 42 days of feeding.

Results from this embodiment are provided in FIGS. 4-10. Body weight gain was measured on day 18 (FIG. 4), days 18-32 (FIG. 5), day 32 (FIG. 6), days 32-42 (FIG. 7), and on day 42 (FIG. 8) of feeding. FIGS. 9 and 10 illustrate results from days 0-32 and days 0-42, respectively. Virginiamycin was administered at two different dosage levels, 0 ppm and 22 ppm. As indicated in FIGS. 4-10, Virginiamycin improved feed conversion rates throughout the test. In embodiments where only the composition was administered, there was not a significant improvement in the adjusted feed/gain, but it did significantly affect bird weight gain throughout the tests. The results also establish that Virginiamycin and the composition provide an additive effect when used in combination. As illustrated in FIG. 9, the composition improved bird weight gain when administered at 150 ppm and 200 ppm and the overall bird weight gain response (illustrated in FIG. 10) corroborated that good responses were obtained using these two amounts of the composition. Table 1, below, provides the body weight gain (in grams) representing the growth response by dose (using only the composition and no Virginiamycin) and feeding phase for each dose over the control embodiment for each embodiment.

TABLE 1

| *Yucca schidigera* and *Quillaja saponaria* Composition (ppm) | Starter 0-18 d | Grower 18-32 d | Withdrawal 32-42 d | Total |
| --- | --- | --- | --- | --- |
| 150 | 50 | 28 | 11 | 89 |
| 200 | 63 | 29 | 2 | 94 |
| 250 | 52 | 21 | 25 | 98 |

Example 3

In this embodiment, the effects of an embodiment of the disclosed combination in broilers vaccinated for coccidiosis was determined. In this example, the combination comprised the *Yucca schidigera* and *Quillaja saponaria* composition, an antibiotic composition, and/or a vaccine composition. Also, the ability of the *Yucca schidigera* and *Quillaja saponaria* composition to enhance the activity of the antibiotic (in this example, Virginiamycin) composition and/or the vaccine composition in coccidiosis-vaccinated birds was determined. In this embodiment, all birds were vaccinated for coccidiosis with CocciVac. The *Yucca schidigera* and *Quillaja saponaria* composition was administered in doses of 0 ppm, 200 ppm, and 250 ppm. Virginiamycin also was administered to the broilers in doses of 0 ppm and 22 ppm. Feed conversion performance, the number of oocysts per gram of feces, and lesions following coccidial challenge were measured.

Figure 11:
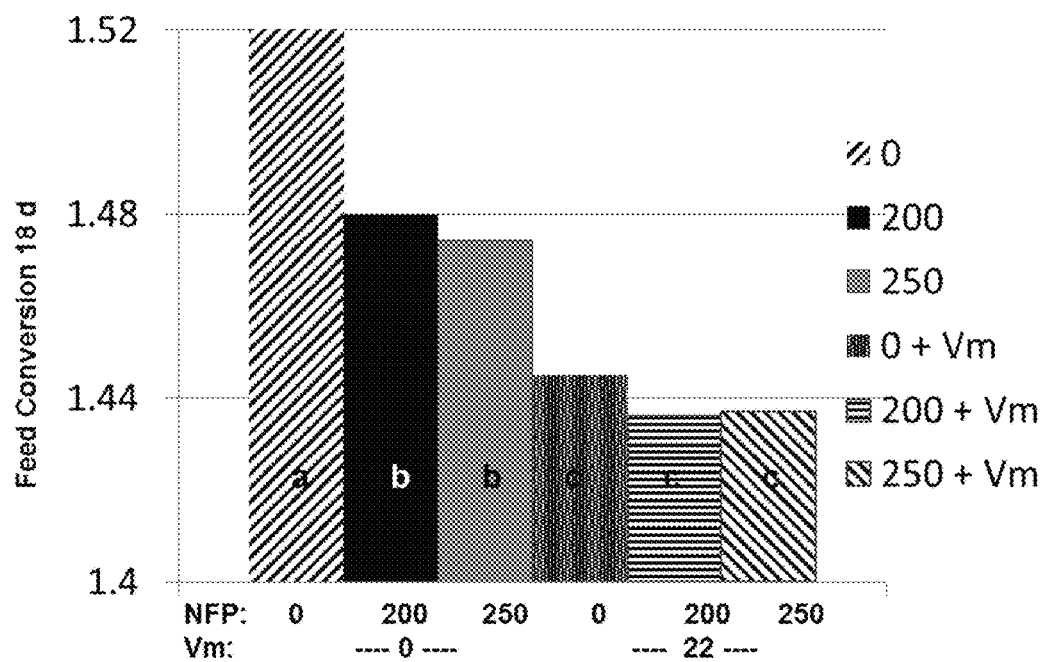
FIG. 11 is a graph of feed conversion rates illustrating results obtained 18 days after feeding vaccinated birds with different feed combinations comprising 0 ppm, 200 ppm, or 250 ppm of a composition embodiment, and/or 0 ppm or 22 ppm Virginiamycin.
Figure 12:
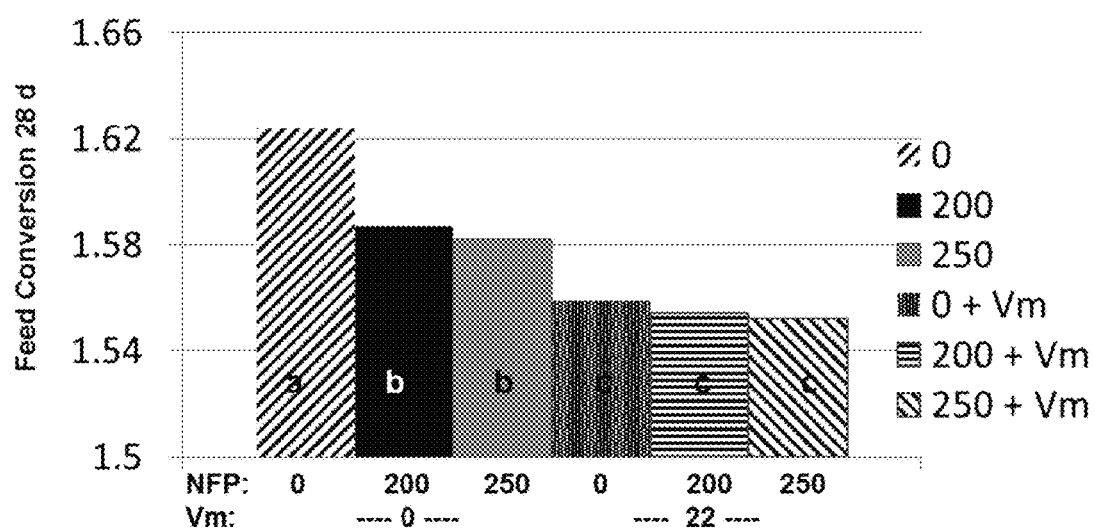
FIG. 12 is a graph of feed conversion rates illustrating results obtained 28 days after feeding vaccinated birds with different feed combinations comprising 0 ppm, 200 ppm, or 250 ppm of a composition embodiment, and/or 0 ppm or 22 ppm Virginiamycin.
Figure 13:
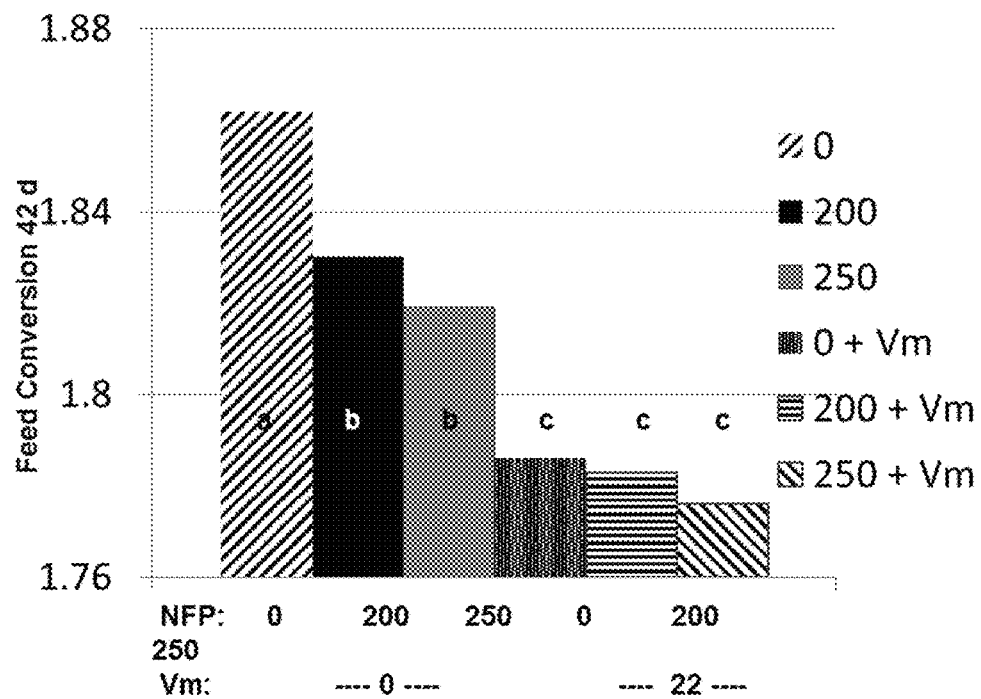
FIG. 13 is a graph of feed conversion rates illustrating results obtained 42 days after feeding vaccinated birds with different feed combinations comprising 0 ppm, 200 ppm, or 250 ppm of a composition embodiment, and/or 0 ppm or 22 ppm Virginiamycin.

Results from this embodiment are illustrated in FIGS. 11-19. As illustrated in FIGS. 11-13, broilers that were administered the vaccine alone did not show the low feed conversion rates that broilers administered with the *Yucca schidigera* and *Quillaja saponaria* composition and/or Virginiamycin. FIGS. 11-13 also illustrate that broilers administered with a combination of the vaccine, the *Yucca schidigera* and *Quillaja saponaria* composition, and Virginiamycin exhibited the lowest feed conversion rates. Without being limited to a particular theory of operation, it is currently believed that higher levels of the *Yucca schidigera* and *Quillaja saponaria* composition (e.g., at least 200 ppm to 500 ppm) promotes the effect of the vaccine while Virginiamycin controls bacterial growth, thereby providing an additive effect which results in an overall improvement in feed conversion efficiency.

Figure 14:
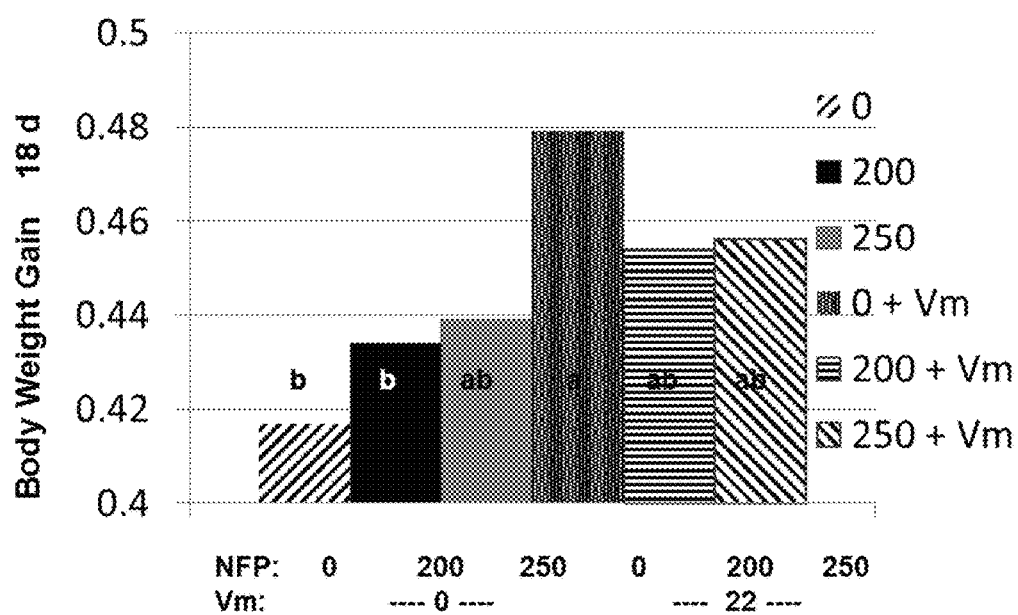
FIG. 14 is a graph of body weight gain illustrating results obtained 18 days after feeding vaccinated birds with different feed combinations comprising 0 ppm, 200 ppm, or 250 ppm of a composition embodiment, and/or 0 ppm or 22 ppm Virginiamycin.
Figure 15:
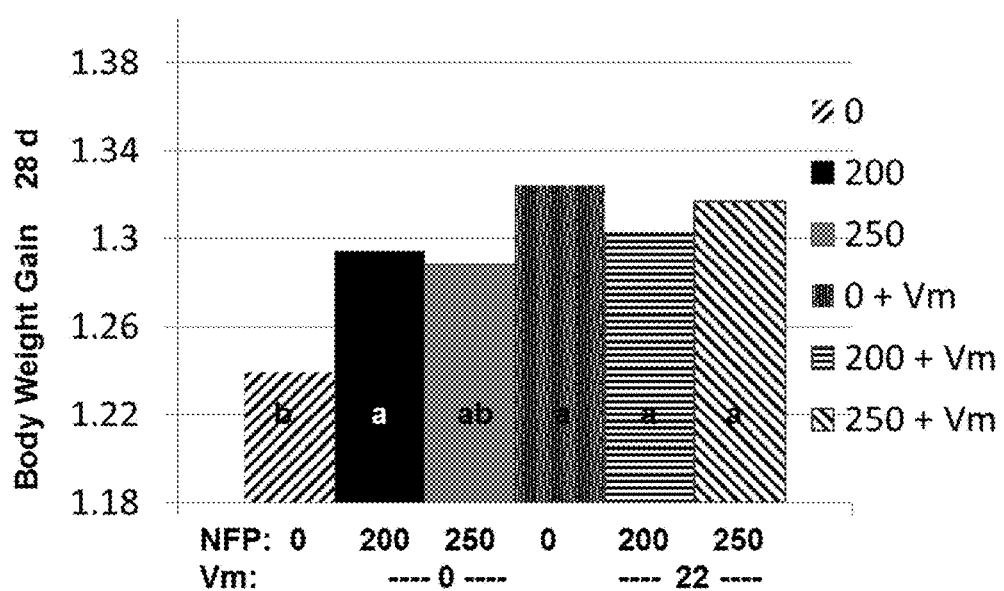
FIG. 15 is a graph of body weight gain illustrating results obtained 28 days after feeding vaccinated birds with different feed combinations comprising 0 ppm, 200 ppm, or 250 ppm of a composition embodiment, and/or 0 ppm or 22 ppm Virginiamycin.
Figure 16:
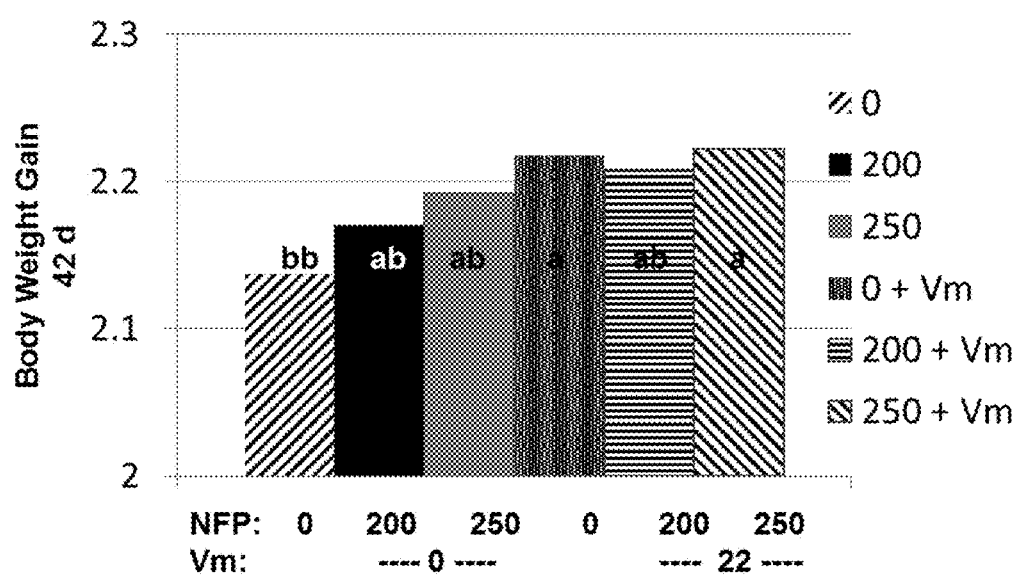
FIG. 16 is a graph of body weight gain illustrating results obtained 42 days after feeding vaccinated birds with different feed combinations comprising 0 ppm, 200 ppm, or 250 ppm of a composition embodiment, and/or 0 ppm or 22 ppm Virginiamycin.
Figure 17:
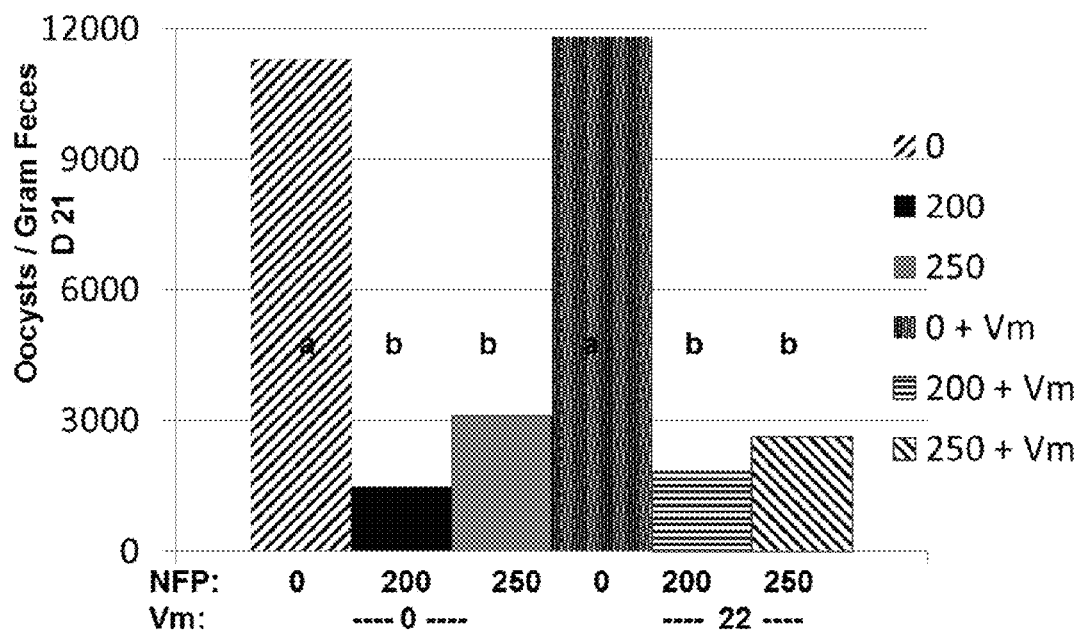
FIG. 17 is a graph of oocysts per gram of feces illustrating results obtained 21 days after feeding vaccinated birds with different feed combinations comprising 0 ppm, 200 ppm, or 250 ppm of a composition embodiment, and/or 0 ppm or 22 ppm Virginiamycin.

The effect of a combination of the vaccine, the *Yucca schidigera* and *Quillaja saponaria* composition, and Virginiamycin on weight gain also was determined. FIGS. 14-16 illustrate these results. Additionally, the ability of coccidial organisms to reproduce in broilers administered a combination of vaccine, the *Yucca schidigera* and *Quillaja saponaria* composition, and Virginiamycin also was tested. As indicated in FIG. 17, the number of oocysts (which results from reproduction of the coccidial organisms) was substantially reduced in broilers that had received the vaccine, the *Yucca schidigera* and *Quillaja saponaria* composition, and Virginiamycin. FIG. 17 also illustrates that combinations of the vaccine and the *Yucca schidigera* and *Quillaja saponaria* composition resulted in decreased oocysts as well.

Figure 18:
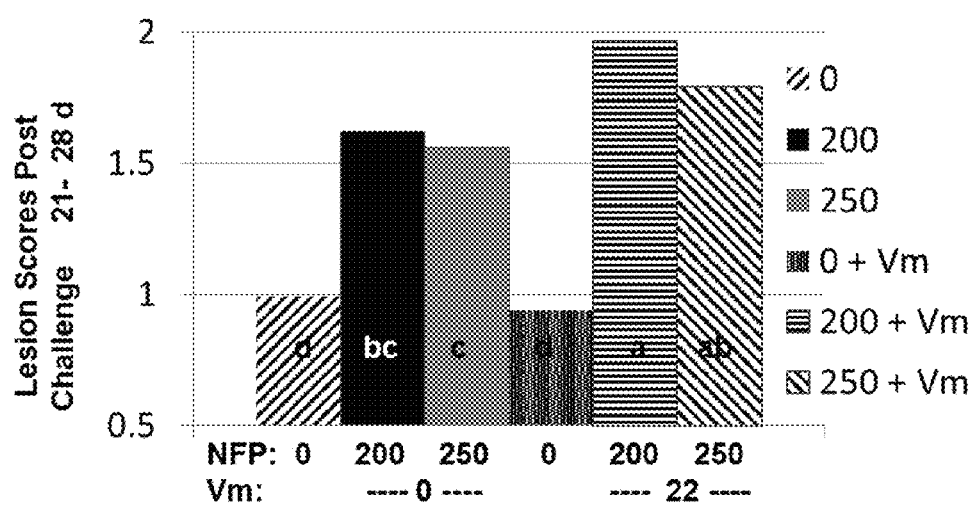
FIG. 18 is a graph of lesion scores post challenge illustrating results obtained 21-28 days after feeding vaccinated birds with different feed combinations comprising 0 ppm, 200 ppm, or 250 ppm of a composition embodiment, and/or 0 ppm or 22 ppm Virginiamycin.
Figure 19:
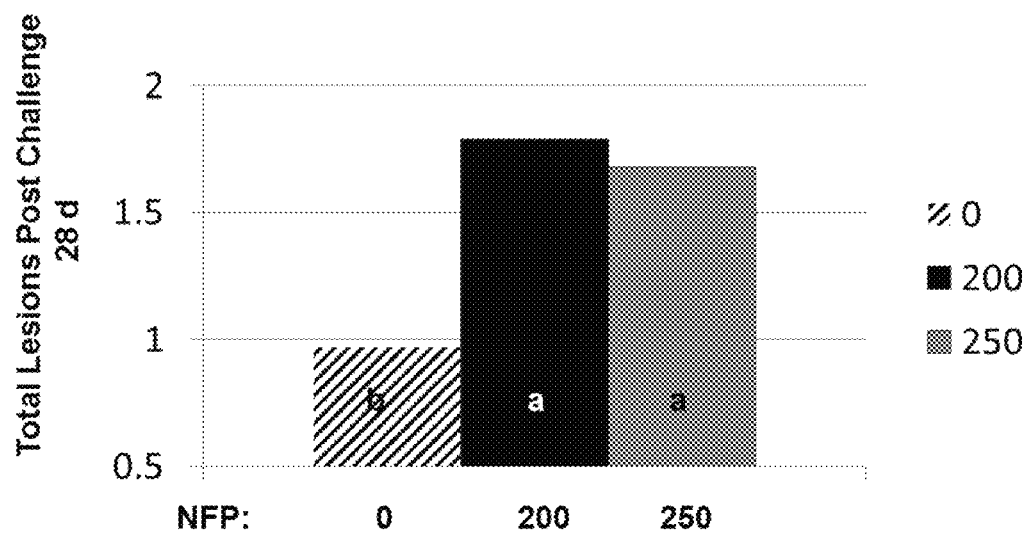
FIG. 19 is a graph of lesion scores post challenge illustrating results obtained 28 days after feeding vaccinated birds with different feed combinations comprising 0 ppm, 200 ppm, or 250 ppm of a composition embodiment, and/or 0 ppm or 22 ppm Virginiamycin, wherein the results were pooled across Virginiamycin levels.
Figure 20:
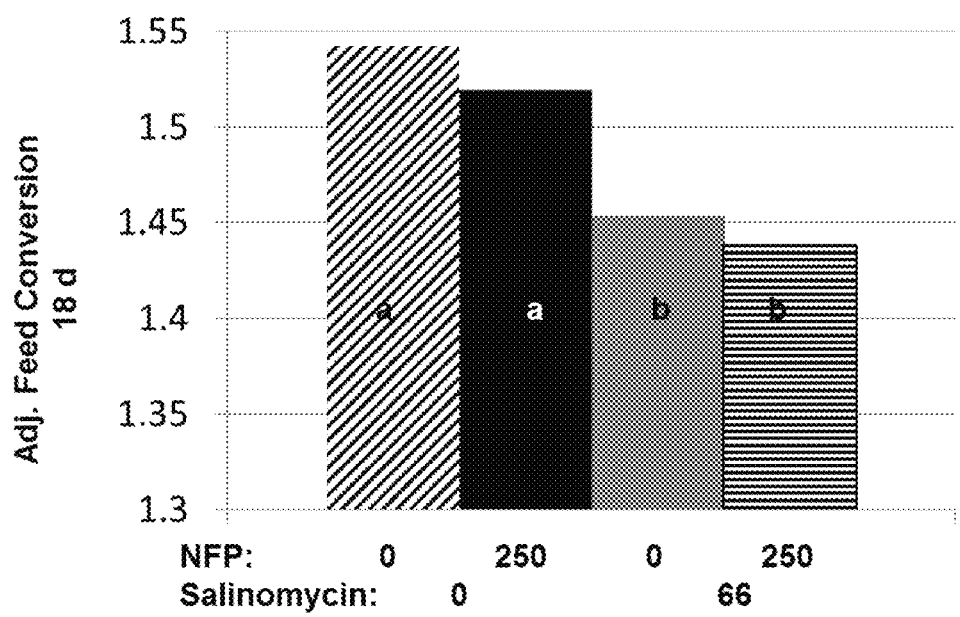
FIG. 20 is a graph of adjusted feed conversion illustrating results obtained 18 days after feeding birds with different combinations comprising a composition embodiment (0 ppm and 250 ppm) and/or Salinomycin (0 ppm and 66 ppm).
Figure 21:
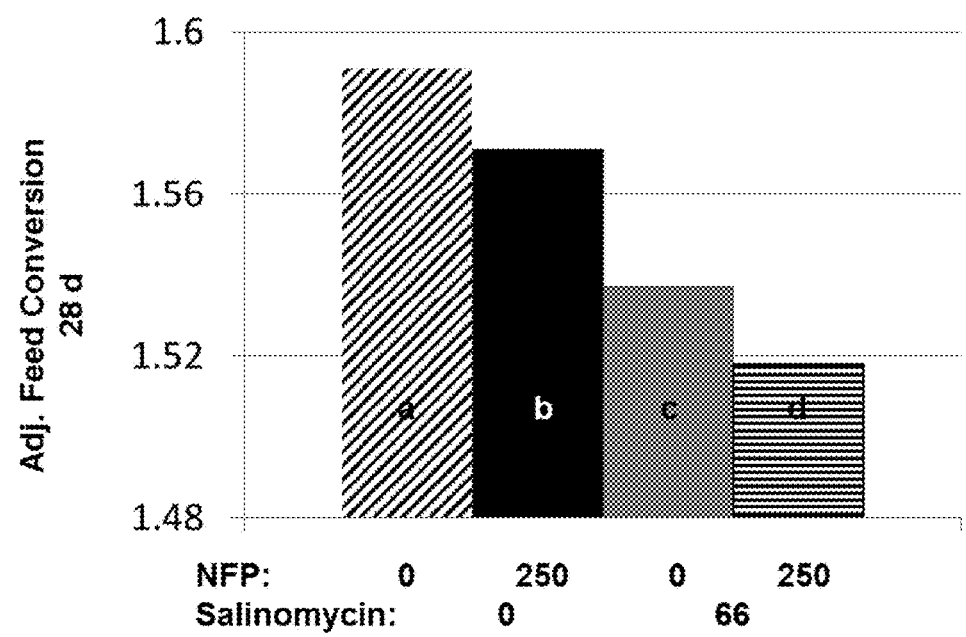
FIG. 21 is a graph of adjusted feed conversion illustrating results obtained 28 days after feeding birds with different combinations comprising a composition embodiment (0 ppm and 250 ppm) and/or Salinomycin (0 ppm and 66 ppm).
Figure 22:
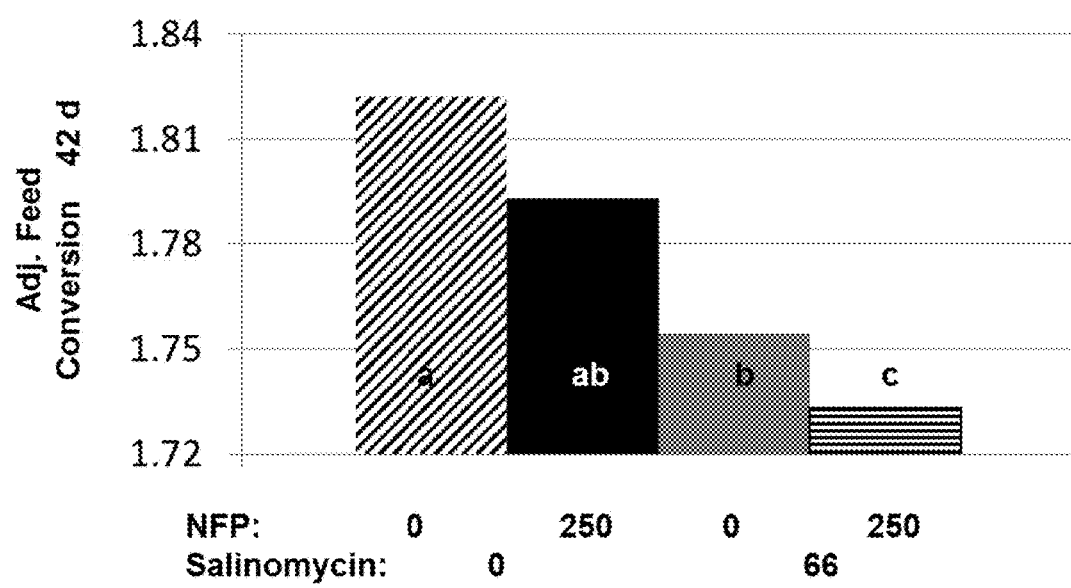
FIG. 22 is a graph of adjusted feed conversion illustrating results obtained 42 days after feeding birds with different combinations comprising a composition embodiment (0 ppm and 250 ppm) and/or Salinomycin (0 ppm and 66 ppm).
Figure 23:
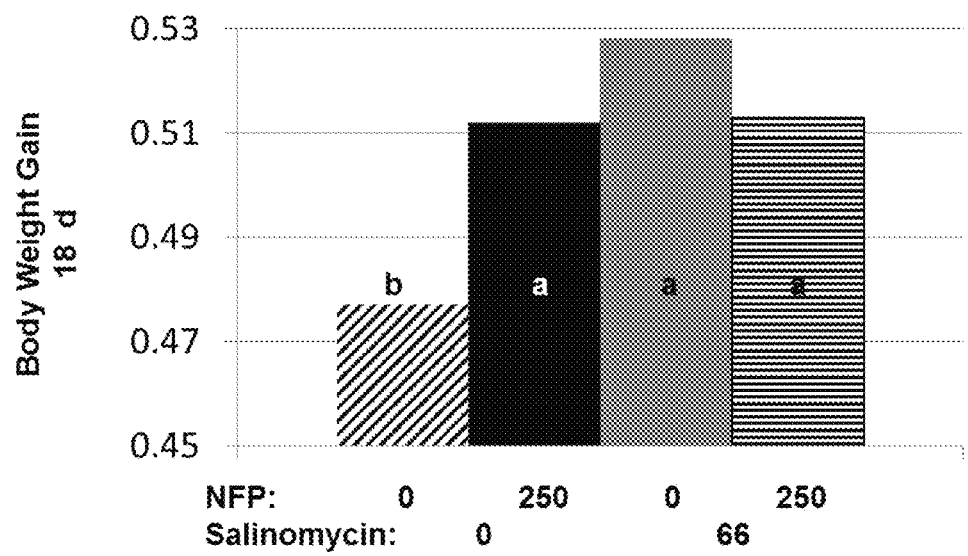
FIG. 23 is a graph of body weight gain illustrating results obtained 18 days after feeding birds with different combinations comprising a composition embodiment (0 ppm and 250 ppm) and/or Salinomycin (0 ppm and 66 ppm).
Figure 24:
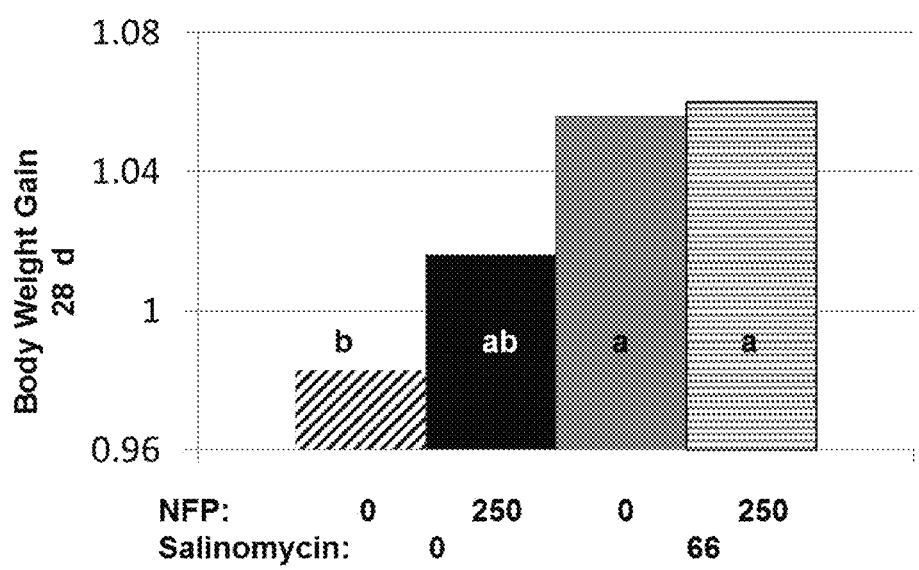
FIG. 24 is a graph of body weight gain illustrating results obtained 28 days after feeding birds with different combinations comprising a composition embodiment (0 ppm and 250 ppm) and/or Salinomycin (0 ppm and 66 ppm).
Figure 25:
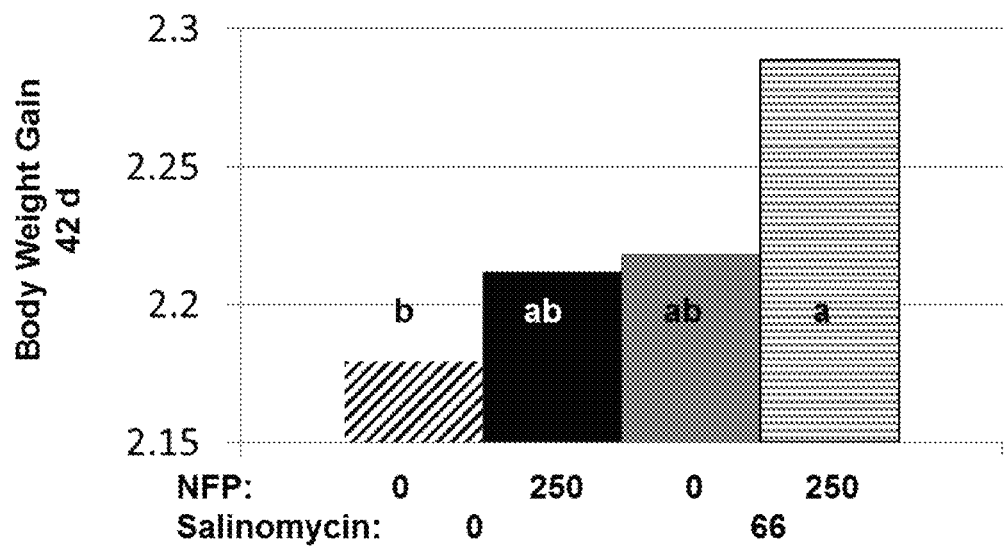
FIG. 25 is a graph of body weight gain illustrating results obtained 42 days after feeding birds with different combinations comprising a composition embodiment (0 ppm and 250 ppm) and/or Salinomycin (0 ppm and 66 ppm).
Figure 26:
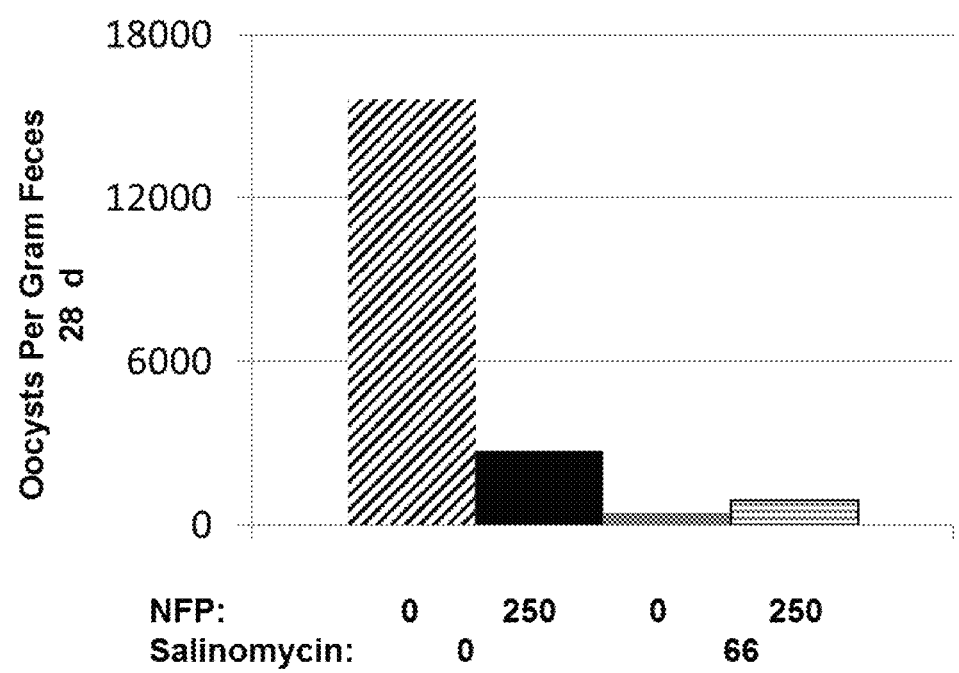
FIG. 26 is a graph of oocysts per gram of feces illustrating results obtained 28 days after feeding vaccinated birds with different feed combinations comprising a composition embodiment (0 ppm and 250 ppm) and/or Salinomycin (0 ppm and 66 ppm).

In this embodiment, a challenge study was also conducted to determine immune potentiation. On day 21 of this embodiment, five birds from each pen were removed and challenged with a 3-species coccidial challenge. The birds were then placed in battery cages for seven days. At day 28, the birds were killed and lesion scored. It was hypothesized that if immune potentiation occurred, then lesions scores following the challenge study would be lower in birds that were administered the *Yucca schidigera* and *Quillaja saponaria* composition than birds that were not administered the *Yucca schidigera* and *Quillaja saponaria* composition and/or Virginiamycin. Surprisingly, however, lower lesions scores than those obtained with control birds (e.g., vaccine only) were not observed in birds that were administered the *Yucca schidigera* and *Quillaja saponaria* composition in amounts ranging from about 200 ppm to 500 ppm, alone or in combination, as illustrated in FIGS. 18 and 19. Without being limited to a particular theory of operation, it is currently believed that the higher lesion scores were obtained in birds that had been administered the *Yucca schidigera* and *Quillaja saponaria* composition and/or Virginiamycin than control birds because the birds that were administered the *Yucca schidigera* and *Quillaja saponaria* composition and/or Virginiamycin experienced lower levels of coccidia exposure prior to extraction from the pens. That is, birds administered the *Yucca schidigera* and *Quillaja saponaria* composition at amounts of about 200 ppm to about 500 ppm and/or Virginiamycin exhibited better anticoccidial capabilities than birds that were not administered the *Yucca schidigera* and *Quillaja saponaria* composition and/or Virginiamycin. The non-control birds therefore did not develop as much immunity to coccidia while in the pen as the control birds who were not administered the combination and therefore were more susceptible to coccidia and better able to develop more immunity while in the pen. The control birds therefore exhibited lower lesions scores once extracted from the pens as they had already developed immunity to the coccidial challenge. The anticoccidial effects of the *Yucca schidigera* and *Quillaja saponaria* composition in amounts ranging from about 200 ppm to about 500 ppm, alone or in combination with Virginiamycin, are therefore corroborated with the data illustrated in FIGS. 18 and 19, as higher lesion scores are indicative of better coccidiosis control (i.e., less immunity). Results from these lesion scoring examples are provided in FIGS. 18 and 19.

Based on this example, it was determined that the *Yucca schidigera* and *Quillaja saponaria* composition, particularly at amounts of about 200 ppm to about 500 ppm, exerts clear anticoccidial effects in vaccinated broilers. There was an approximate 4- to 5-fold reduction in fecal oocyst count during the first 28 days in birds administered a combination of a vaccine and the *Yucca schidigera* and *Quillaja saponaria* composition. Also, the anticoccidial effects of the *Yucca schidigera* and *Quillaja saponaria* composition was supported by the challenge study disclosed above, which clearly showed higher susceptibility to coccidial challenge in birds that were not administered the *Yucca schidigera* and *Quillaja saponaria* composition.

Example 4

In this particular embodiment, the compatibility of the *Yucca schidigera* and *Quillaja saponaria* composition with Salinomycin was evaluated. The treatments included embodiments where no feed additive was provided (e.g., none of the composition added), where 250 ppm of the composition was provided, where 66 ppm of Salinomycin was provided, and embodiments where 250 ppm of the composition and 66 ppm of Salinomycin were provided in combination. The anticoccidial effects and immune potentiation of each test embodiment were evaluated and the results are provided graphically in FIGS. 20-26.

As illustrated in FIGS. 20-23, the adjusted feed conversions of the birds were determined after 18 days, 28 days, and 42 days, respectively. The results show an improvement in feed conversion rate in birds administered the *Yucca schidigera* and *Quillaja saponaria* composition and Salinomycin in combination. A significant point difference in feed conversion rate was seen after each time period, as illustrated in FIGS. 20-23. Without being limited to a single theory of operation, it is currently believed that administering the composition in combination with Salinomycin increases the effectiveness of the Salinomycin in reducing the negative effects of coccidiosis (e.g., poorer feed conversion rates). The results also illustrated an additive effect between the composition and the Salinomycin. Body weight gain also increased in birds that were administered a combination of the composition and Salinomycin as compared to birds that did not receive the combination (e.g., birds administered feed only, birds administered the composition only, and birds administered Salinomycin only). These results are clearly illustrated in FIGS. 24-26.

Figure 27:
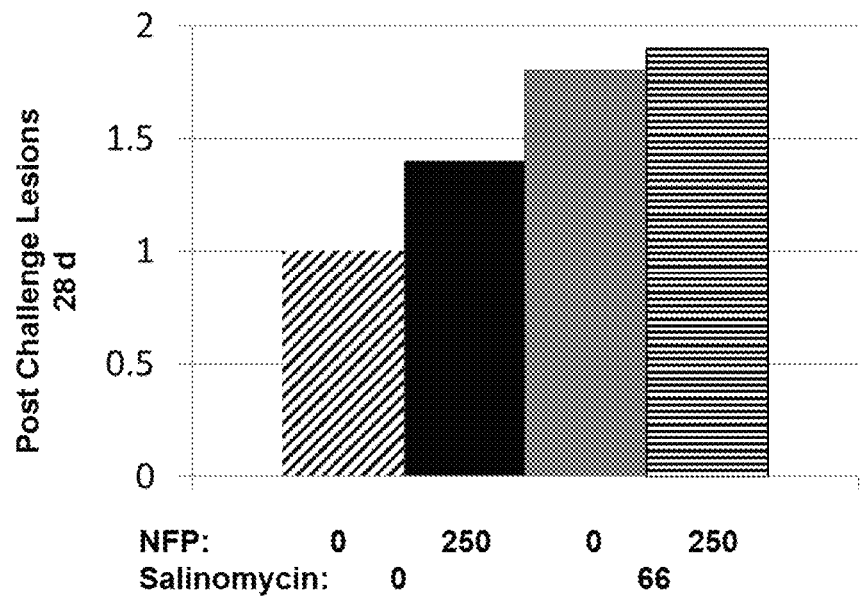
FIG. 27 is a graph of lesion scores post challenge illustrating results obtained 28 days after feeding vaccinated birds with different feed combinations comprising 0 ppm, 200 ppm, or 250 ppm of a composition embodiment and/or 0 ppm or 22 ppm Virginiamycin.

The combination of the composition and Salinomycin also reduced the number of oocysts per gram of feces in broilers, as indicated in FIG. 27. A challenge study was also conducted to evaluate the potential for immune potentiation. Similar to the challenge study described in Example 3, 5 birds were removed from each pen after 21 days. These birds were challenged with a three-species coccidial challenge and then placed in batter cages for seven days. On day 28, the birds were killed and lesion scored. This challenge study indicated independent anticoccidial effects of the composition and Salinomycin as both increased the susceptibility of broilers to coccidial challenge between days 21 and 28.

Example 5

In this particular embodiment, the effects of the composition and Salinomycin, independently, were evaluated. Lower amounts of the composition were tested, including the amount that is typically used by those in the art (i.e., 125 ppm). Salinomycin treatments used 44 ppm or 66 ppm Salinomycin. Non-infected birds that received no medication were used as a control (entry 1 of Table 2, below). Also, some birds were administered 66 ppm of Salinomycin, but where not infected (entry 7 of Table 2, below). The remaining birds were infected with 200,000 oocysts of field isolate of *E. acervulina*, which is a species of *Eimeria* that causes coccidiosis in poultry, particularly old poultry, and subjected to the treatments described below in entries 2-6 of Table 2. As indicated by the data provided in Table 2, no significant differences in body weights and/or adjusted feed conversion were observed at the lower levels of the *Yucca schidigera* and *Quillaja saponaria* composition (abbreviated as "YQ composition" in Table 2) used in these tested embodiments.

TABLE 2

| E. acervulina Treatment | Feed Consum. | Adj. Fd. Conv. | Avg. Wt. Gain | Lesion Score | OPG** |
|---|---|---|---|---|---|
| NM*, Noninfect | 2.796 a | 1.791 b | 0.260 a | 0.0 d | 0 |
| NM, Infect | 2.531 bc | 2.125 a | 0.203 c | 2.1 a | 26780 |
| YQ composition 100 ppm | 2.441 c | 2.125 a | 0.194 c | 1.7 bc | 24645 |
| YQ composition 125 ppm | 2.436 c | 2.136 a | 0.191 c | 2.0 ab | 22411 |

TABLE 2-continued

| E. acervulina Treatment | Feed Consum. | Adj. Fd. Conv. | Avg. Wt. Gain | Lesion Score | OPG** |
|---|---|---|---|---|---|
| YQ composition 150 ppm | 2.490 c | 2.186 a | 0.192 c | 2.3 a | 36301 |
| Sal 44 ppm | 2.804 a | 1.946 b | 0.241 ab | 1.3 c | 2734 |
| Sal 66 ppm | 2.692 ab | 1.948 b | 0.231 b | 1.4 c | 217 |

*NM = non-medicated treatments
**OPG = oocysts per gram of fecal material

Similar protocols were used to determine the effects of lower amounts of NFP (e.g., 100 ppm, 125 ppm, and 150 ppm) on birds infected with *E. maxima*, a common form of *Eimeria* found in commercial broilers. Infected birds were infected with 37,500 oocysts of field isolate of *E. maxima*. The infected birds were subjected to the treatments described below in entries 2-6 of Table 3. As indicated by the data provided in Table 3, no significant differences in body weights and/or adjusted feed conversion were observed at the lower levels of the *Yucca schidigera* and *Quillaja saponaria* composition (abbreviated as "YQ composition" in Table 3) used in these tested embodiments.

TABLE 3

| E. maxima Treatment | Feed Consum. | Adj. Fd. Conv. | Avg. Wt. Gain | Lesion Score | OPG |
|---|---|---|---|---|---|
| NM, Noninfect | 2.796 a | 1.791 c | 0.260 a | 0.0 e | 0 |
| NM, Infect | 2.674 ab | 2.225 a | 0.201 c | 1.9 ab | 1884 |
| YQ composition 100 ppm | 2.638 bc | 2.191 a | 0.202 c | 1.8 ab | 11072 |
| YQ composition 125 ppm | 2.534 c | 2.216 a | 0.191 c | 1.6 bc | 335 |
| YQ composition 150 ppm | 2.611 bc | 2.258 a | 0.194 c | 2.0 a | 1100 |
| Sal 44 ppm | 2.718 ab | 2.021 b | 0.225 b | 1.3 cd | 4435 |
| Sal 66 ppm | 2.647 bc | 1.960 b | 0.230 b | 1.2 d | 167 |

*NM = non-medicated treatments
**OPG = oocysts per gram of fecal material

In another test embodiment, the effects of lower amounts of NFP (e.g., 100 ppm, 125 ppm, and 150 ppm) on birds infected with *E. tenella*, a species of *Eimeria* that causes hemorrhagic cecal coccidiosis in poultry, particularly young poultry. Infected birds were infected with 100,000 oocysts of field isolate of *E. tenella*. The infected birds were subjected to the treatments described below in entries 2-6 of Table 4. As indicated by the data provided in Table 4, no significant differences in body weights and/or adjusted feed conversion were observed at the lower levels of the *Yucca schidigera* and *Quillaja saponaria* composition (abbreviated as "YQ composition" in Table 4) used in these tested embodiments.

TABLE 4

| E. tenlla Treatment | Feed Consum. | Adj. Fd. Conv. | Avg. Wt. Gain | Lesion Score | OPG |
|---|---|---|---|---|---|
| NM, Noninfect | 2.796 a | 1.791 c | 0.260 a | 0.0 d | 0 |
| NM, Infect | 2.770 a | 2.012 a | 0.236 b | 1.9 a | 1984 |
| YQ composition 100 ppm | 2.692 a | 2.017 a | 0.226 b | 1.3 b | 617 |
| YQ composition 125 ppm | 2.757 a | 1.999 a | 0.231 b | 1.5 b | 11589 |
| YQ composition 150 ppm | 2.723 a | 1.892 b | 0.240 ab | 1.6 ab | 2267 |
| Sal 44 ppm | 2.787 a | 1.929 ab | 0.242 ab | 0.8 c | 800 |
| Sal 66 ppm | 2.671 a | 1.863 bc | 0.245 ab | 0.6 c | 150 |

*NM = non-medicated treatments
**OPG = oocysts per gram of fecal material

Accordingly, the results provided in this example establish that amounts of the *Yucca schidigera* and *Quillaja saponaria* composition ranging from 100 ppm to 150 ppm are not as effective in improving feed conversion rates of animals as are amounts of the *Yucca schidigera* and *Quillaja saponaria* composition that range from about 200 ppm to about 500 ppm. The results also reflect that amounts of the *Yucca schidigera* and *Quillaja saponaria* composition ranging from 100 ppm to 150 ppm do not have the same anticoccidial activity as those embodiments wherein about 200 ppm to about 500 ppm of the *Yucca schidigera* and *Quillaja saponaria* composition is used.

General Procedures for Examples 6-8

In the embodiments described below in Examples 6-8, the following conditions and methods were utilized. The test house was divided into pens of equal size, arranged along a central aisle. Subtracting out for equipment, the initial bird density was ~0.84 square ft/bird. Each pen had 5 feet high side walls with bottom 1½ feet being of solid wood to prevent bird migration. All flooring of each pen had approximately 4 inches of built-up litter.

The temperature of the building was monitored. Environmental conditions during the trial (temperature) were appropriate (optimum) to the age of the animals Illumination was provided by fluorescent bulbs placed above the pens. The lighting scheme was 24 hours of light per day.

The diets were provided ad libitum in one tube-type feeder per pen. From day 1 until day 7, feed will also be supplied on a tray placed directly on the litter of each pen.

Standard floor pen management practices were used throughout the experiment. Animals and housing facilities were inspected twice daily, observing and recording the general health status, constant feed and water supply as well as temperature, removing all dead birds, and recognizing unexpected events.

All feeds were fed as crumbles/pellets. Quantities of all basal feed and test articles used to prepare treatment batches were documented. Each batch of feed was mixed and bagged separately. Each bag was identified with the study number, date of mix, type of feed, and the correct treatment number. Complete records of feed mixing, and test article inventories were maintained. A sample from the beginning, middle, and end of each treatment feed were mixed to form a composite sample. This sample of each treatment was retained until study end. All feed was weighed by pen. Starter feed was fed from Day 0 to 18. On Day 18, non-consumed starter was weighed and discarded. Grower feed was issued and fed until Day 28. On Day 28, non-consumed grower was weighed and discarded. Finisher feed was issued and fed until Day 42. On Day 42, non-consumed finisher was weighed and discarded.

Day of hatch male chicks were obtained from Cobb-Vantress hatchery, Cleveland, Ga. The strain was Cobb 500. Breeder flock was recorded. 1760 chicks were allocated to the study. At the hatchery, the birds received routine vaccinations. The birds were sexed at the hatchery. In Example 7, all chicks were spray vaccinated with conventional doses of Coccivac-B. Only healthy appearing chicks were used in the study. In examples 6 and 7, fifty-five males were allocated to each treatment pen by blocks. In example 8, fifty-two males were allocated to each treatment pen by blocks. No birds were replaced during the course of the study. Number and disposition of all birds not used for allocation were documented. Bird weights (kg) by pen were recorded at study initiation, Day 18, 28, and termination (Day 42).

On Days 18, 28, and 35, three birds per pen were sacrificed and coccidial lesion scored for degree of *E. acervulina, E. maxima* and *E. tenella* infection (Examples 6 and 7). The system of Johnson and Reid (1970) wherein 0 is normal and 1, 2, 3, or 4 indicate increasing severity of infection were used for lesion scoring. In Example 8, three birds per pen were sacrificed on days and 28 and coccidial lesion scored for degree of *E. acervulina, E. maxima* and *E. tenella* infection. The system of Johnson and Reid (1970) wherein 0 is normal and 1, 2, 3, or 4 indicate increasing severity of infection were used for lesion scoring.

On Days 18 and 28 fresh fecal samples were collected from each pen (Examples 6 and 7). On Days 18 and 28, fresh fecal samples were collected from each pen (Example 8). These representative samples were tested to determine the degree of oocysts shedding/cycling. Oocysts per gram were determined for each sample.

Example 6

In this particular example, compositions were administered for different time periods during the life span of birds to determine preferred administration time periods for improved performance. Also studied were the control of field strains less sensitive to ionophore medication and the performance of composition embodiments alone or in combination with Salinomycin fed to broilers.

Birds were administered a diet comprising 250 mg of a composition embodiment comprising 90% *Quillaja saponaria* and 10% *Yucca schidigera* in combination with 66 ppm of Salinomycin for different time periods. In some embodiments, the composition embodiment was fed to the birds for the entire period between birth and death (typically days 0 to 42, referred to as a "full program") or during intermediate time periods during the birds' life spans, such as from days 0 to 28 (referred to as a "starter/grower program"), from days 29-42 (referred to as a "finisher program"), or from days 19-42 (referred to as a "grower/finisher program"). The birds were exposed to a coccidial challenge from day of age (e.g., day 0). Numerical results are provided by Tables 5-7 and also are presented graphically by FIGS. 28-37.

TABLE 5

| Treatments | Feed Intake | Adj. FCR | Avg. Wt Gain |
|---|---|---|---|
| Day 18 | | | |
| 1. Sal 66 ppm + Composition 250 ppm D 0-42 | 33.19b | 1.445a | 0.377a |
| 2. Sal 66 ppm + Composition 250 ppm D 0-28 | 33.23b | 1.445a | 0.377a |
| 3. Sal 66 ppm + Composition 250 ppm D 29-42 | 35.46a | 1.474a | 0.394a |
| 4. Sal 66 ppm + Composition 250 ppm D 19-42 | 35.09ab | 1.483a | 0.391a |
| Day 28 | | | |
| 1. Sal 66 ppm + Composition 250 ppm D 0-42 | 85.06a | 1.652b | 0.944a |
| 2. Sal 66 ppm + Composition 250 ppm D 0-28 | 85.59a | 1.649b | 0.948a |

TABLE 5-continued

| Treatments | Feed Intake | Adj. FCR | Avg. Wt Gain |
|---|---|---|---|
| 3. Sal 66 ppm + Composition 250 ppm D 29-42 | 85.36a | 1.701a | 0.920a |
| 4. Sal 66 ppm + Composition 250 ppm D 19-42 | 86.28a | 1.676ab | 0.941a |
| Day 42 | | | |
| 1. Sal 66 ppm + Composition 250 ppm D 0-42 | 212.19a | 1.807c | 2.412a |
| 2. Sal 66 ppm + Composition 250 ppm D 0-28 | 208.87a | 1.837bc | 2.376a |
| 3. Sal 66 ppm + Composition 250 ppm D 29-42 | 206.71a | 1.887a | 2.295a |
| 4. Sal 66 ppm + Composition 250 ppm D 19-42 | 205.66a | 1.859ab | 2.295a |

"D" = days; letters "a," "b," and "c" are used to indicate break points based on statistical analysis and thereby provide an indication of statistically significant differences between observed values.

TABLE 6

| Treatments | Feed Intake | Adj. FCR | Avg. Wt Gain |
|---|---|---|---|
| Day 18 | | | |
| 1. Sal 66 ppm + Composition 250 ppm D 0-42 | 33.19b | 1.445a | 0.377a |
| 2. Sal 66 ppm + Composition 250 ppm D 0-28 | 33.23b | 1.445a | 0.377a |
| 3. Sal 66 ppm + Composition 250 ppm D 29-42 | 35.46a | 1.474a | 0.394a |
| 4. Sal 66 ppm + Composition 250 ppm D 19-42 | 35.09ab | 1.483a | 0.391a |
| Day 28 | | | |
| 1. Sal 66 ppm + Composition 250 ppm D 0-42 | 85.06a | 1.652b | 0.944a |
| 2. Sal 66 ppm + Composition 250 ppm D 0-28 | 85.59a | 1.649b | 0.948a |
| 3. Sal 66 ppm + Composition 250 ppm D 29-42 | 85.36a | 1.701a | 0.920a |
| 4. Sal 66 ppm + Composition 250 ppm D 19-42 | 86.28a | 1.676ab | 0.941a |
| Day 42 | | | |
| 1. Sal 66 ppm + Composition 250 ppm D 0-42 | 212.19a | 1.807c | 2.412a |
| 2. Sal 66 ppm + Composition 250 ppm D 0-28 | 208.87a | 1.837bc | 2.376a |
| 3. Sal 66 ppm + Composition 250 ppm D 29-42 | 206.71a | 1.887a | 2.295a |
| 4. Sal 66 ppm + Composition 250 ppm D 19-42 | 205.66a | 1.859ab | 2.295a |

"D" = days; letters "a," "b," and "c" are used to indicate break points based on statistical analysis and thereby provide an indication of statistically significant differences between observed values.

TABLE 7

| Treatments | E.A. | E.M. | E.T. | AVG |
|---|---|---|---|---|
| Lesions Day 18 | | | | |
| 1. Sal 66 ppm + Composition 250 ppm D 0-42 | 2.4a | 1.5a | 0.2ab | 1.4a |
| 2. Sal 66 ppm + Composition 250 ppm D 0-28 | 2.3a | 1.0a | 0.4a | 1.2a |
| 3. Sal 66 ppm + Composition 250 ppm D 29-42 | 2.2a | 1.4a | 0.2b | 1.3a |
| 4. Sal 66 ppm + Composition 250 ppm D 19-42 | 2.4a | 1.3a | 0.3ab | 1.3a |

TABLE 7-continued

| Treatments | E.A. | E.M. | E.T. | AVG |
|---|---|---|---|---|
| Lesions Day 28 | | | | |
| 1. Sal 66 ppm + Composition 250 ppm D 0-42 | 1.2a | 0.2a | 0.0a | 0.4a |
| 2. Sal 66 ppm + Composition 250 ppm D 0-28 | 1.1a | 0.1a | 0.0a | 0.4a |
| 3. Sal 66 ppm + Composition 250 ppm D 29-42 | 1.4a | 0.2a | 0.0a | 0.5a |
| 4. Sal 66 ppm + Composition 250 ppm D 19-42 | 1.4a | 0.0a | 0.0a | 0.5a |
| Lesions Day 35 | | | | |
| 1. Sal 66 ppm + Composition 250 ppm D 0-42 | 0.3a | 0.3a | 0.2a | 0.3a |
| 2. Sal 66 ppm + Composition 250 ppm D 0-28 | 0.3a | 0.2a | 0.0a | 0.2a |
| 3. Sal 66 ppm + Composition 250 ppm D 29-42 | 0.1a | 0.2a | 0.3a | 0.2a |
| 4. Sal 66 ppm + Composition 250 ppm D 19-42 | 0.1a | 0.2a | 0.1a | 0.1a |

"D" = days; "E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

TABLE 8

| Treatments | E.A. | E.M. | E.T. | Total |
|---|---|---|---|---|
| Oocysts per gram Day 18 | | | | |
| 1. Sal 66 ppm + Composition 250 ppm D 0-42 | 4992b | 1374bc | 528b | 6893bc |
| 2. Sal 66 ppm + Composition 250 ppm D 0-28 | 3400b | 1616c | 352ab | 5368c |
| 3. Sal 66 ppm + Composition 250 ppm D 29-42 | 7471a | 2705a | 1072a | 11248a |
| 4. Sal 66 ppm + Composition 250 ppm D 19-42 | 5394ab | 2931ab | 938a | 9263ab |
| Oocysts per gram Day 28 | | | | |
| 1. Sal 66 ppm + Composition 250 ppm D 0-42 | 2789ab | 209ab | 402b | 3400b |
| 2. Sal 66 ppm + Composition 250 ppm D 0-28 | 2295b | 235b | 302b | 2831b |
| 3. Sal 66 ppm + Composition 250 ppm D 29-42 | 4255a | 930a | 796a | 5980a |
| 4. Sal 66 ppm + Composition 250 ppm D 19-42 | 4020a | 829ab | 586a | 5435a |

"D" = days; "E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

Figure 31:
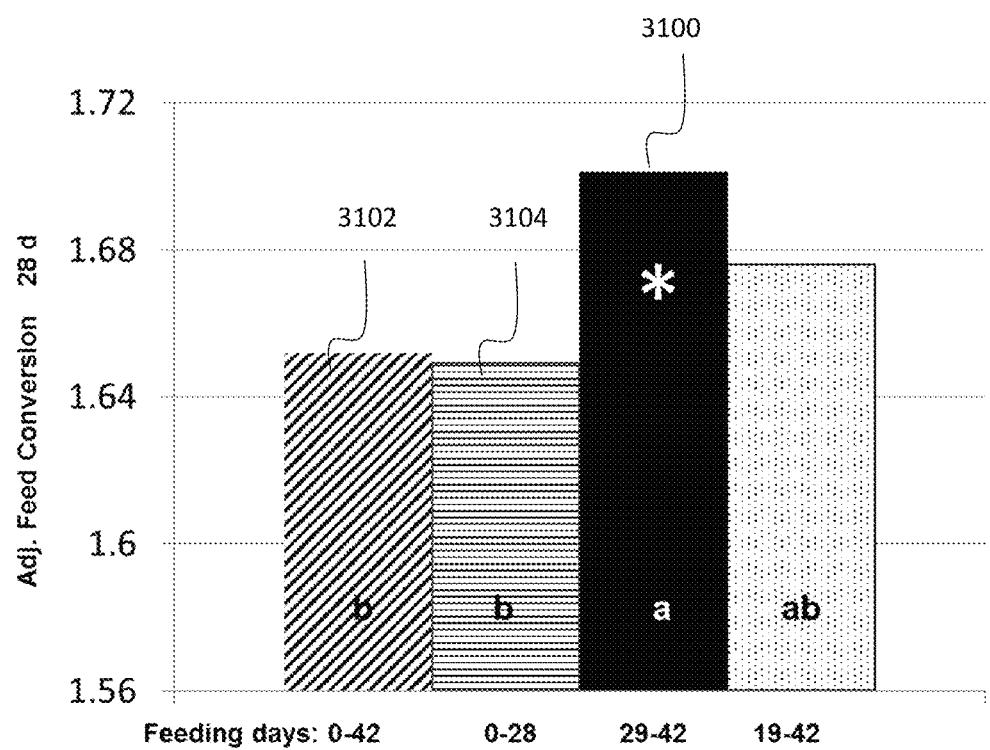
FIG. 31 is a graph of adjusted feed conversion illustrating results on day 28 for birds fed salinomycin and 250 mg of a composition embodiment for days 0-42, days 0-28, days 29-42, and days 19-42.
Figure 32:
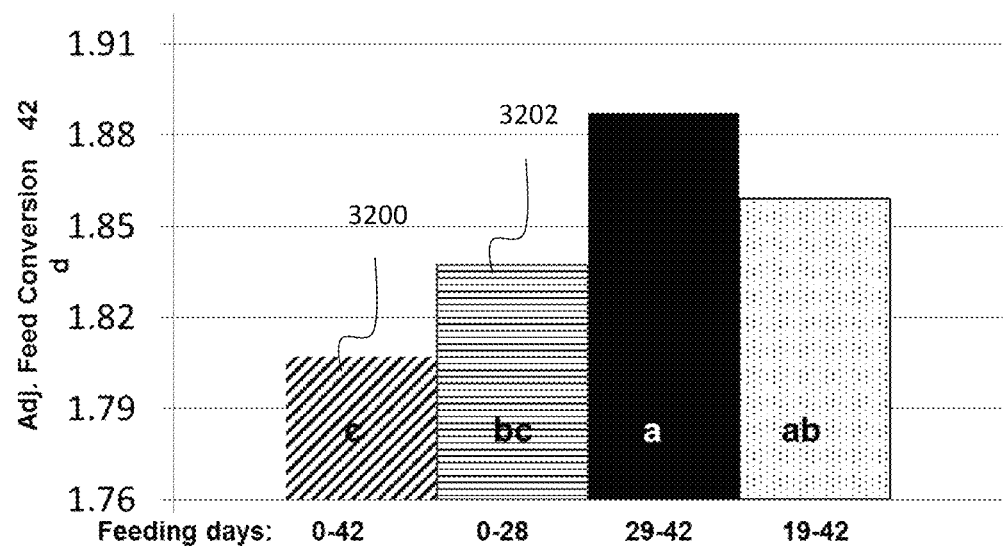
FIG. 32 is a graph of adjusted feed conversion illustrating results on day 42 for birds fed salinomycin and 250 mg of a composition embodiment for days 0-42, days 0-28, days 29-42, and days 19-42.
Figure 33:
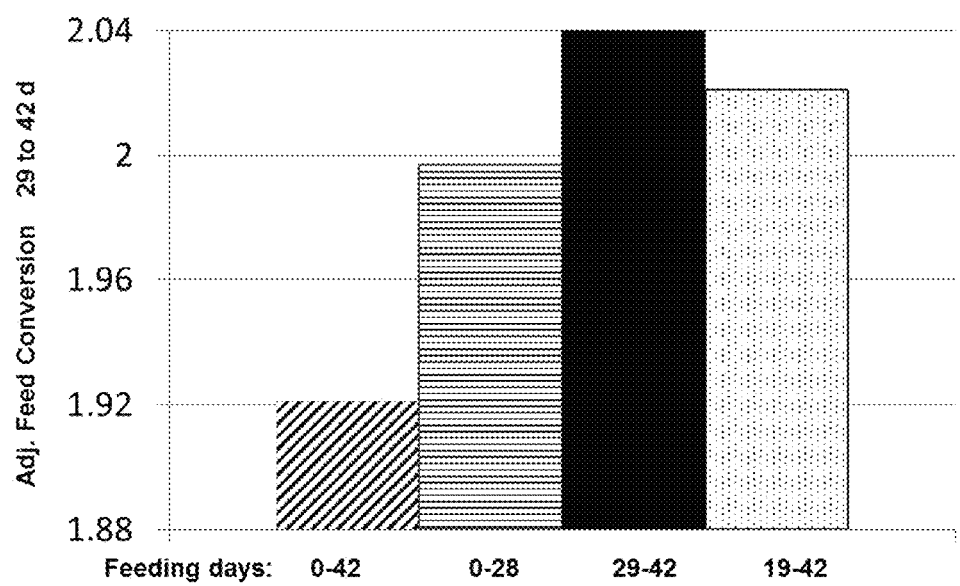
FIG. 33 is a graph of adjusted feed conversion illustrating results on days 29-42 for birds fed salinomycin and 250 mg of a composition embodiment for days 0-42, days 0-28, days 29-42, and days 19-42.
Figure 34:
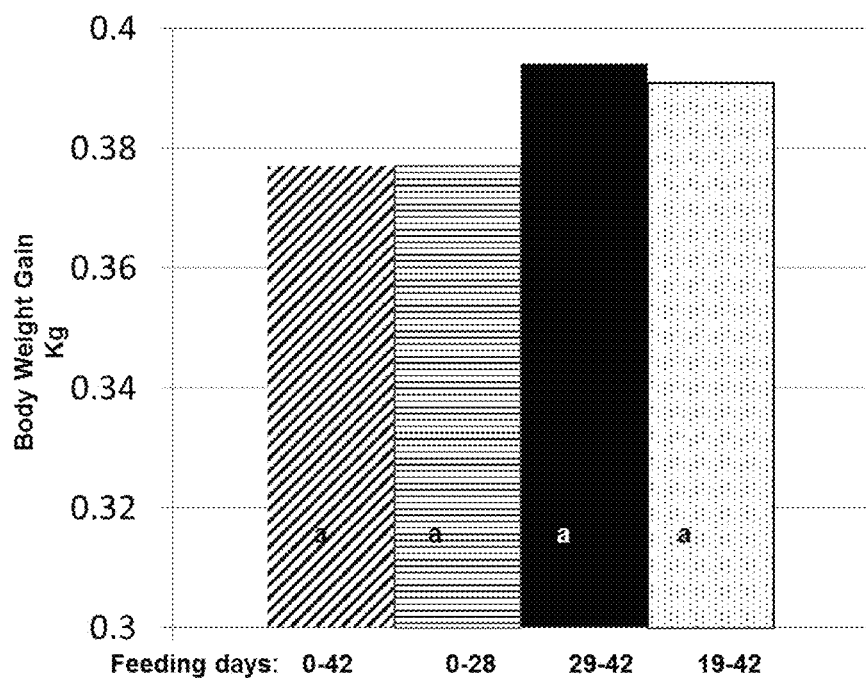
FIG. 34 is a graph of body weight gain (kg) illustrating results on day 18 for birds fed salinomycin and 250 mg of a composition embodiment for days 0-42, days 0-28, days 29-42, and days 19-42.
Figure 35:
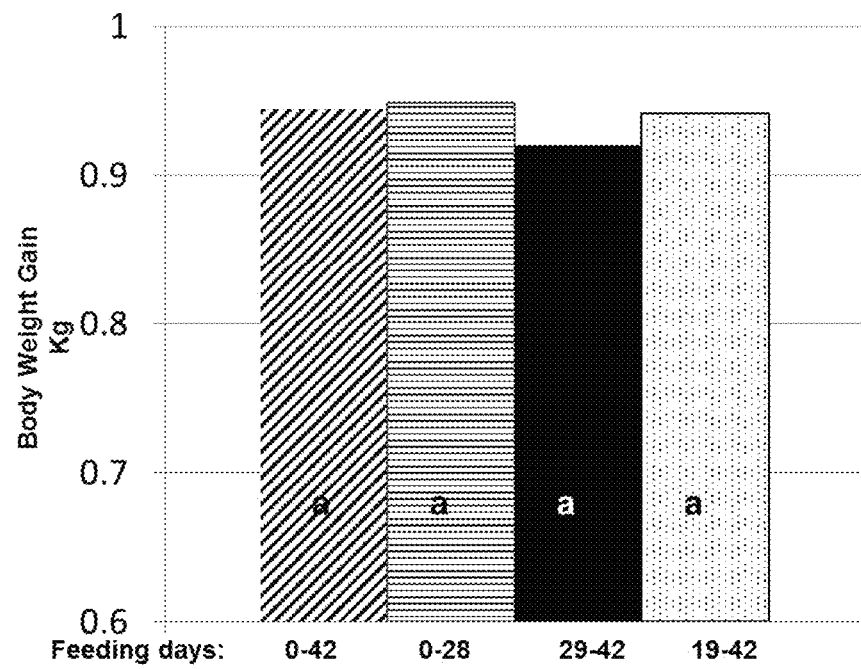
FIG. 35 is a graph of body weight gain (kg) illustrating results on day 28 for birds fed salinomycin and 250 mg of a composition embodiment for days 0-42, days 0-28, days 29-42, and days 19-42.
Figure 36:
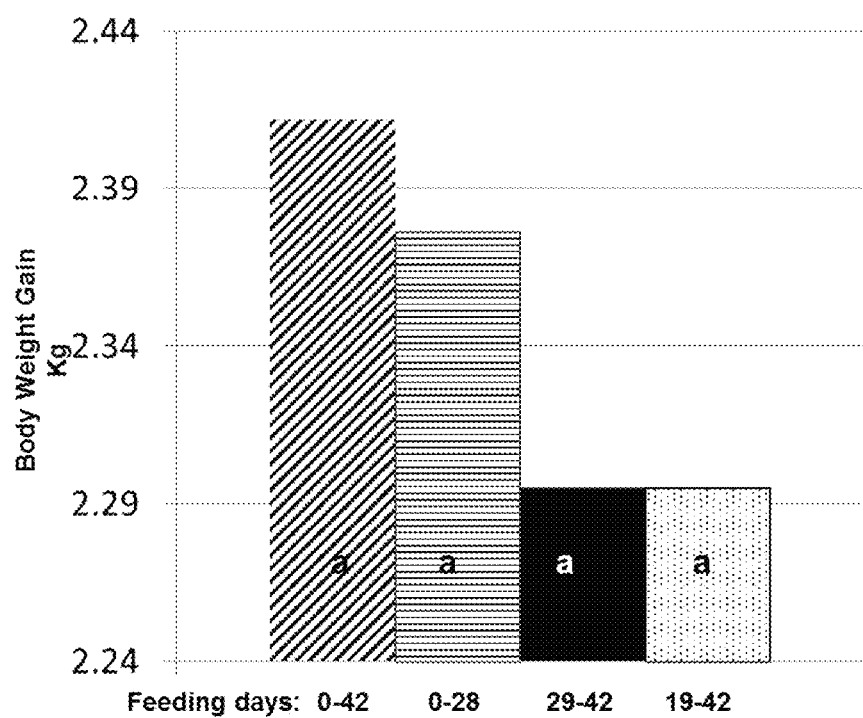
FIG. 36 is a graph of body weight gain (kg) illustrating results on day 42 for birds fed salinomycin and 250 mg of a composition embodiment for days 0-42, days 0-28, days 29-42, and days 19-42.
Figure 37:
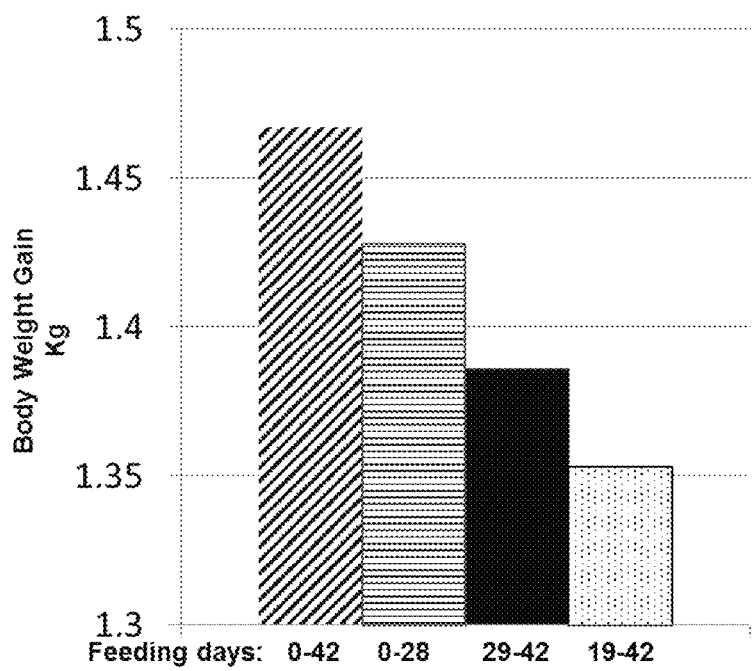
FIG. 37 is a graph of body weight gain (kg) illustrating results on days 29-42 for birds fed salinomycin and 250 mg of a composition embodiment for days 0-42, days 0-28, days 29-42, and days 19-42.
Figure 38:
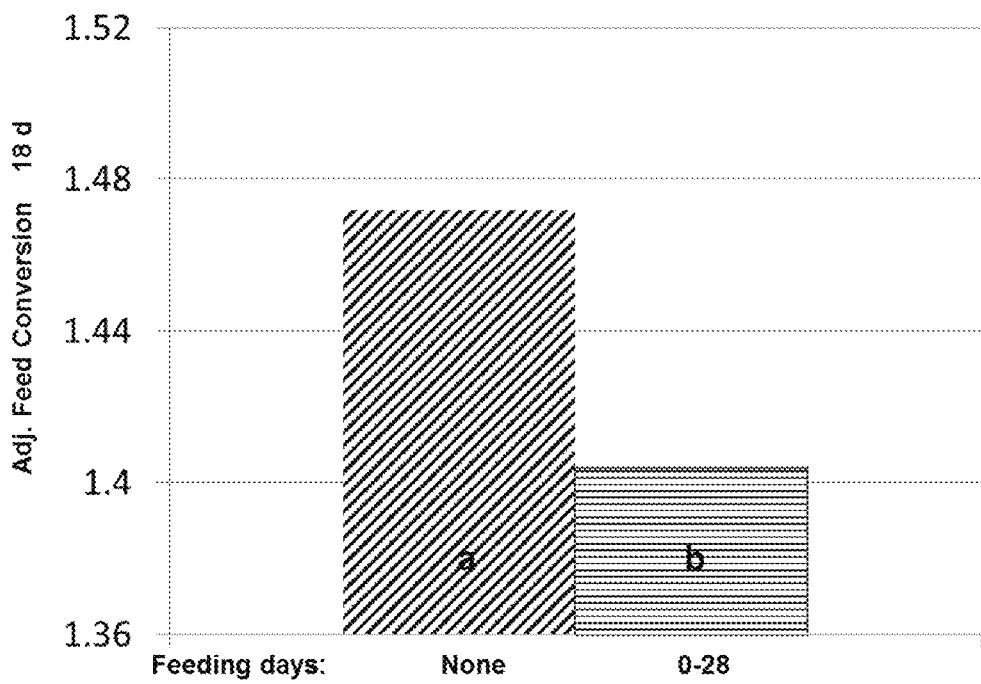
FIG. 38 is a graph of adjusted feed conversion illustrating the effects of a composition embodiment on birds vaccinated with a coccidiosis vaccine at birth wherein the results illustrated are for birds that were not fed the composition embodiment (left bar) and for birds that were fed the composition for different time periods (right bar); the results were measured at day 18.
Figure 39:
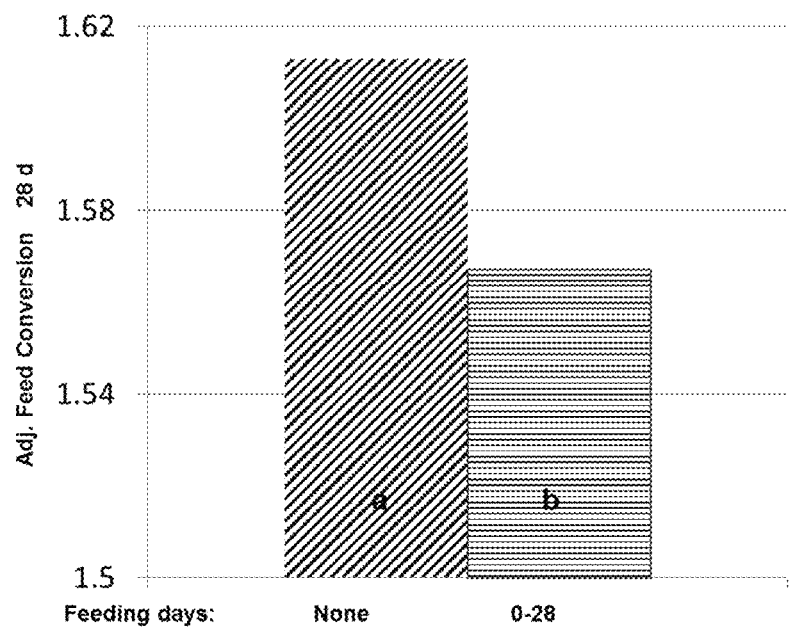
FIG. 39 is a graph of adjusted feed conversion illustrating the effects of a composition embodiment on birds vaccinated with a coccidiosis vaccine at birth wherein the results illustrated are for birds that were not fed the composition embodiment (left bar) and for birds that were fed the composition for different time periods (right bar); the results were measured at day 28.
Figure 40:
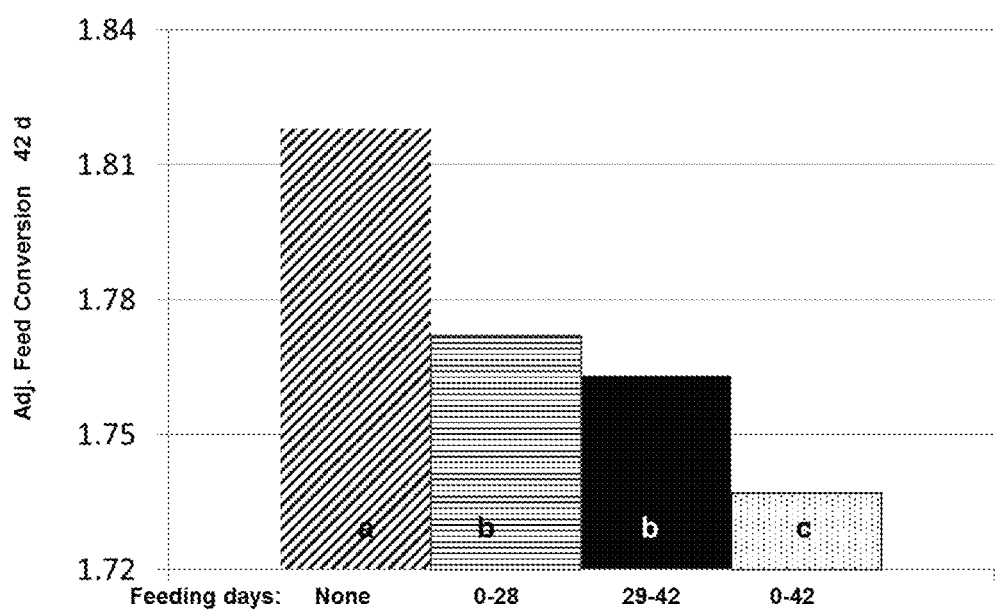
FIG. 40 is a graph of adjusted feed conversion illustrating results on day 42 for birds administered a coccidiosis vaccine and fed 0 mg or 250 mg of a composition embodiment for days 0-42, days 0-28, days 29-42, and days 19-42.
Figure 41:
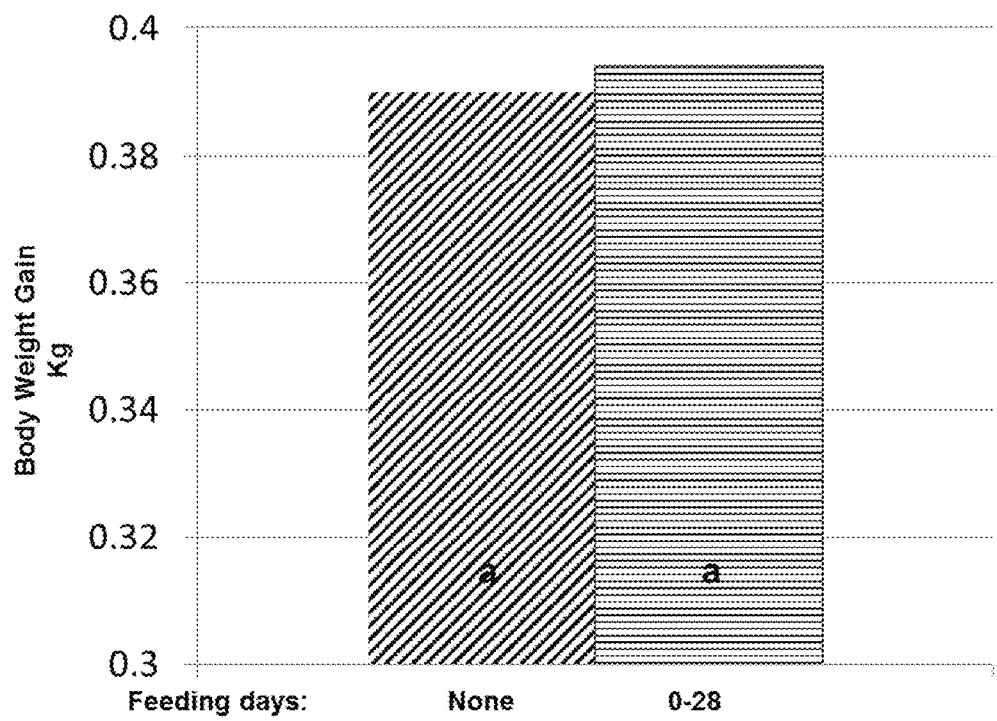
FIG. 41 is a graph of body weight gain illustrating the effects of a composition embodiment on birds vaccinated with a coccidiosis vaccine at birth wherein the results illustrated are for birds that were not fed the composition embodiment (left bar) and for birds that were fed the composition for different time periods (right bar); the results were measured at day 18.
Figure 42:
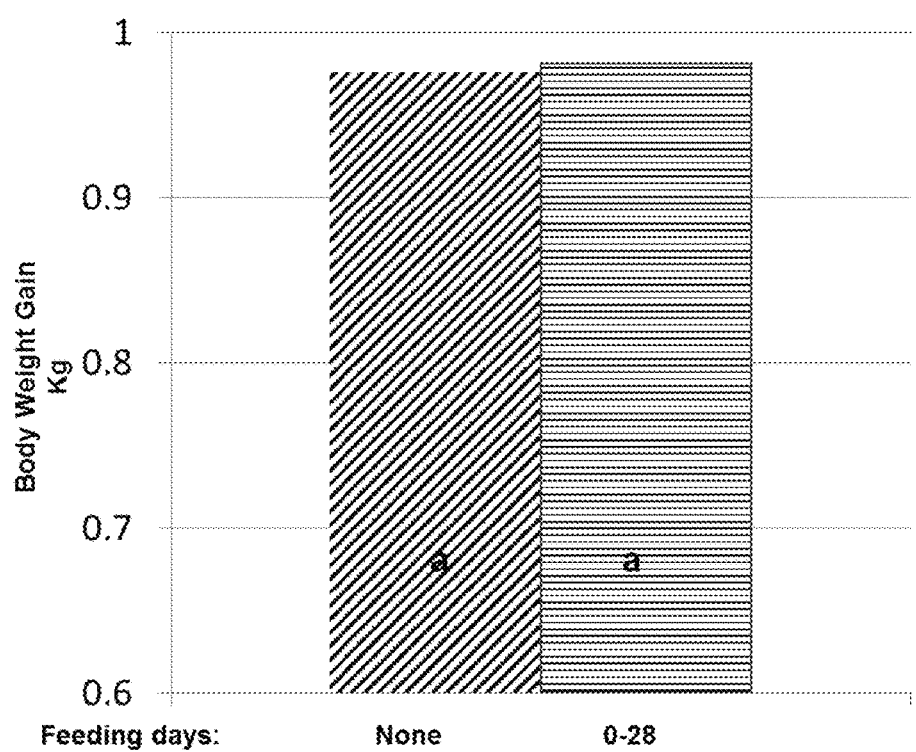
FIG. 42 is a graph of body weight gain illustrating the effects of a composition embodiment on birds vaccinated with a coccidiosis vaccine at birth wherein the results illustrated are for birds that were not fed the composition embodiment (left bar) and for birds that were fed the composition for different time periods (right bar); the results were measured at day 28.
Figure 43:
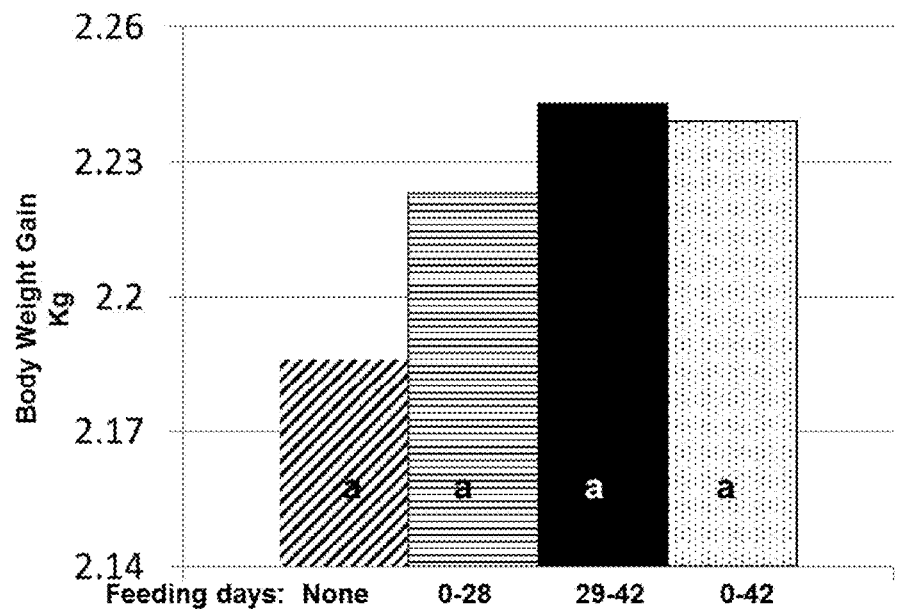
FIG. 43 is a graph of body weight gain illustrating results on day 42 for birds administered a coccidiosis vaccine and fed 0 mg or 250 mg of a composition embodiment for days 0-42, days 0-28, days 29-42, and days 19-42.
Figure 44:
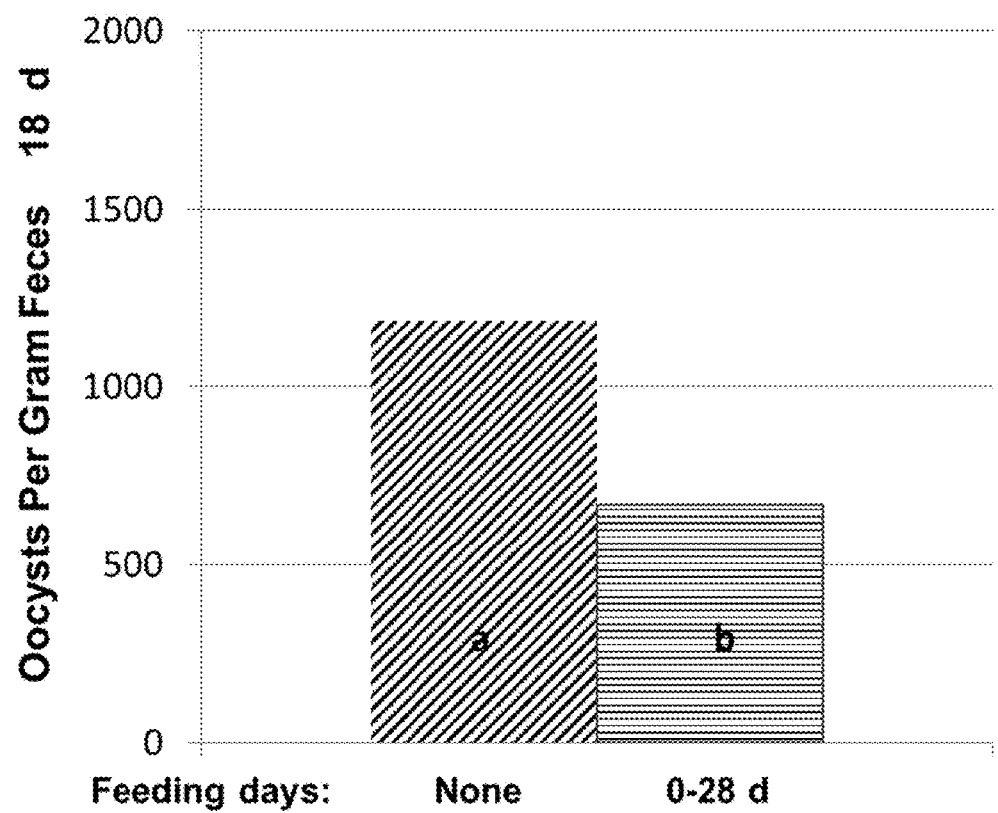
FIG. 44 is a graph of oocysts per gram of feces illustrating results on day 18 for birds administered a coccidiosis vaccine and fed 0 mg or 250 mg of a composition embodiment for days 0-42, days 0-28, days 29-42, and days 19-42.
Figure 45:
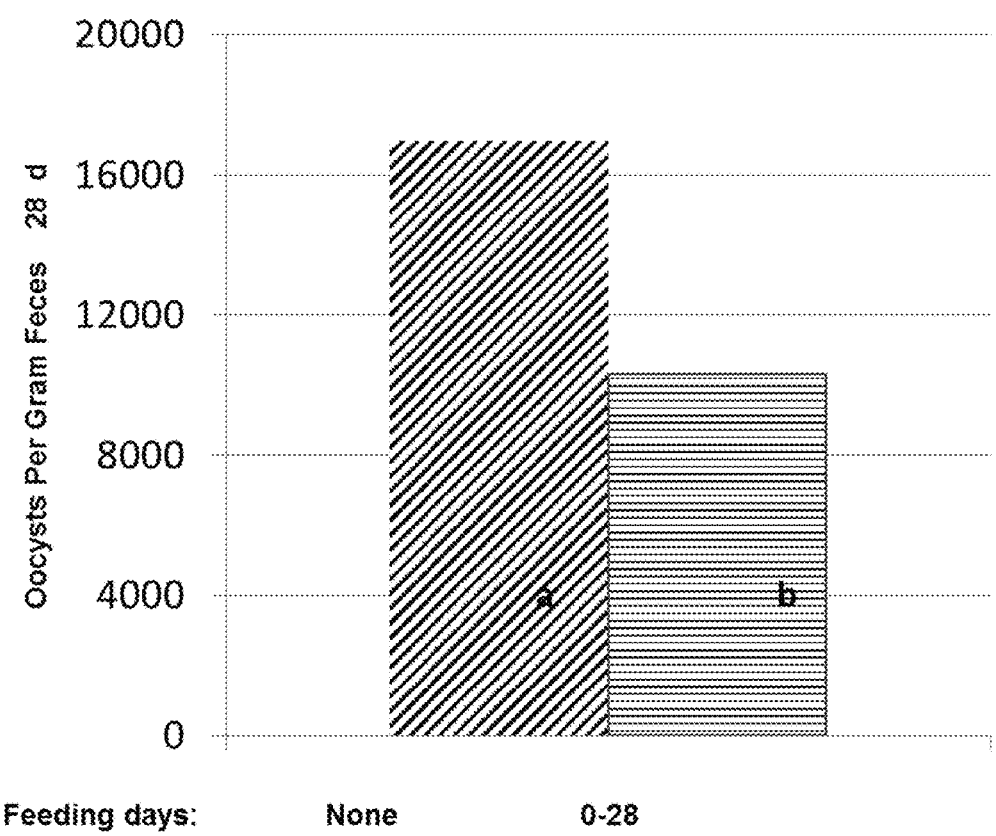
FIG. 45 is a graph of oocysts per gram of feces illustrating results on day 28 for birds administered a coccidiosis vaccine and fed 0 mg or 250 mg of a composition embodiment for days 0-42, days 0-28, days 29-42, and days 19-42.

The data provided by Tables 5-8 indicate that the compositions and combinations disclosed herein are capable of providing significant and beneficial reductions in adjusted feed conversion rates, thus illustrating the benefits of that the compositions and combinations (e.g., compositions and antibiotics, antimicrobials, and/or anticoccidials) can have on animal health and productivity. In some embodiments, a significant difference (e.g., a reduction of 2% or higher) in the feed conversion rates of birds administered the composition for a full program was observed (see FIGS. 30-33). In some embodiments, using a full program of a composition/combination (e.g., a composition and Salinomycin) resulted in a 5 point difference in feed conversion. See, for example, FIGS. 31 and 32. With reference to FIG. 31, a comparison of the results represented by bar 3100 (representing embodiments where no composition had been administered at the time of measurement) with bar 3102 (representing a full program) and/or bar 3104 (representing a starter/grower program) corroborates that feed conversion rates can be significantly improved using the composition in combination with a component capable of reducing the adverse effects of coccidial infection (e.g., a component having activity against coccidia, such as Salinomycin). With reference to FIG. 32, improved feed conversion rates are even more pronounced at day 42 as can be seen by comparing bar 3200 (days 0-42) and bar 3202 (days 0-28). The data provided by this example illustrate that embodiments of the composition can enhance the activity of Salinomycin, and therefore can be effective with other antimicrobials, antibiotics, and/or anticoccidial agents.

Figure 28:
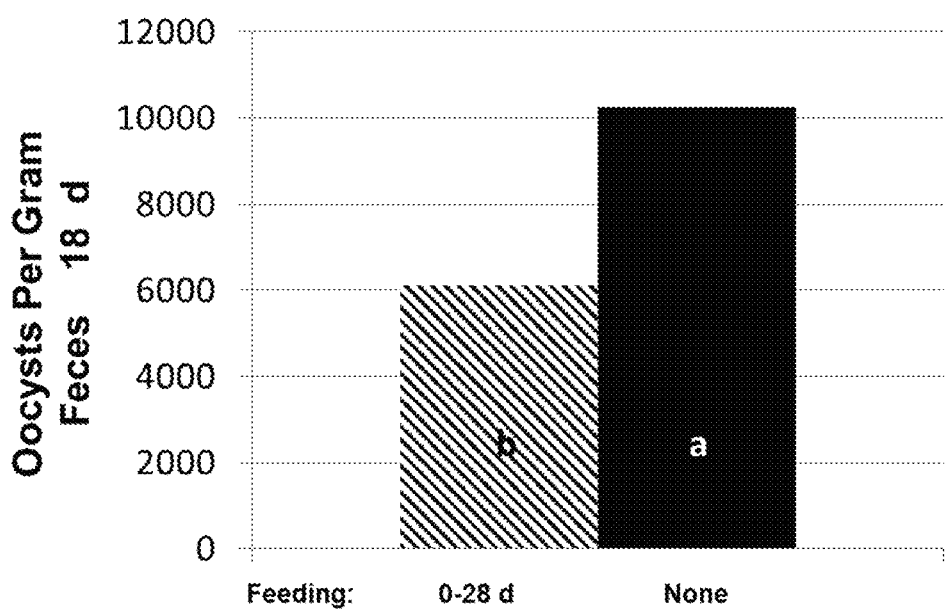
FIG. 28 is a graph of oocysts per gram of feces illustrating results on day 18 for birds fed (a) salinomycin and 250 mg of a composition embodiment or (b) salinomycin alone.
Figure 29:
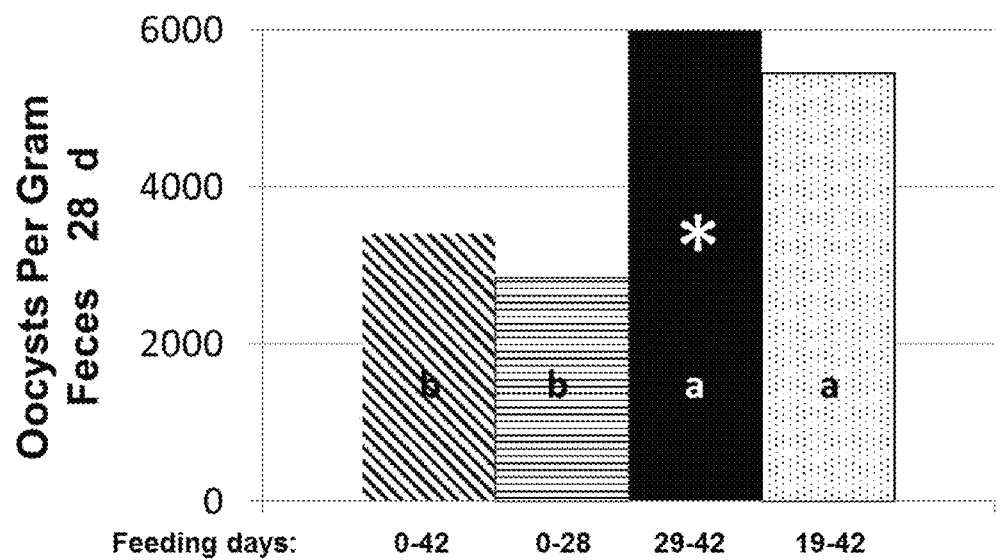
FIG. 29 is a graph of oocysts per gram of feces illustrating results on day 28 for birds fed salinomycin and 250 mg of a composition embodiment for days 0-42, days 0-28, days 29-42, and days 19-42.
Figure 30:
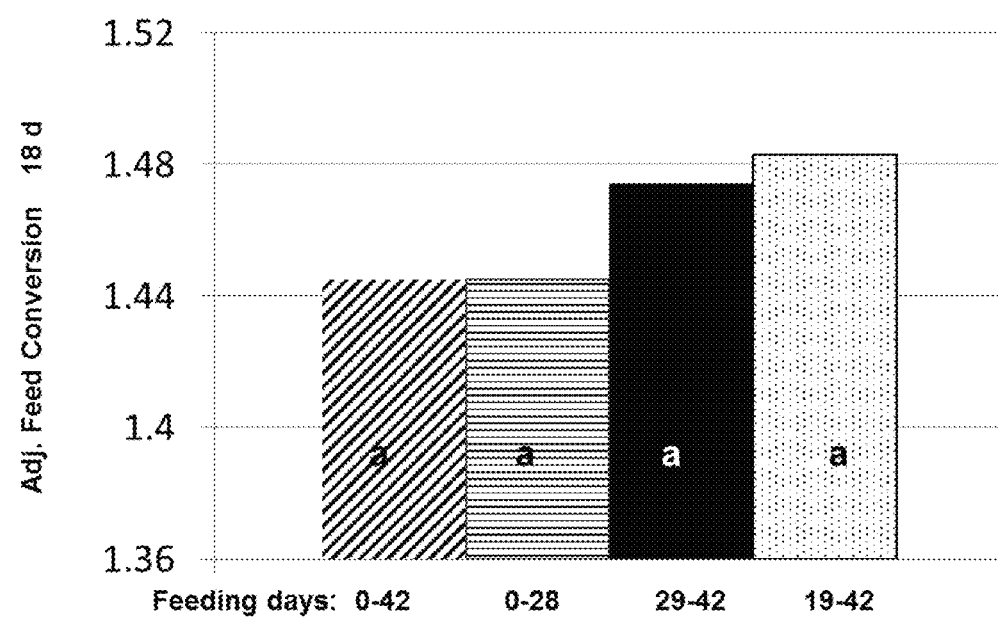
FIG. 30 is a graph of adjusted feed conversion illustrating results on day 18 for birds fed salinomycin and 250 mg of a composition embodiment for days 0-42, days 0-28, days 29-42, and days 19-42.

The data also indicate that significant reductions in oocyst production were observed when the birds were fed the composition as compared to birds that did not receive any of the composition (see FIG. 28). Furthermore, birds receiving a full program of the composition exhibited significant decreases in oocyst production as indicated by FIG. 29 and Table 7. Additionally, the composition also did not exhibit any deleterious effects on body weight gain of the birds as evidenced by FIGS. 34-37.

Example 7

In this embodiment, the effects of a composition embodiment in different feeds and as a complete program were evaluated in combination with the use of a coccidiosis vaccine. The coccidiosis vaccine was administered to the birds at hatching in this example; however, the vaccine can be administered at other times during a bird's life cycle and even in combination with the composition. The birds in this embodiment were raised for a 42 day growth period. A control group of birds was used, wherein the birds were vaccinated but were not fed the composition. Other groups included groups of birds fed 250 mg of a composition embodiment from day 0 to day 28 (starter/grower program), from day 29 to day 42 (finisher program), and from day 0 to day 42 (full program). Data from the embodiments described in this example are provided below in Tables 9-11 and also are illustrated graphically in FIGS. 38-45.

TABLE 9

| | Feed Intake | Adj. FCR | Wt. Gain | Mortality |
|---|---|---|---|---|
| Day 18 | | | | |
| 1. No Additive | 34.69ab | 1.473a | 0.383a | |
| 2. Composition D 0-28 | 33.82ab | 1.408ab | 0.393a | |
| 3. Composition D 28-42 | 35.66a | 1.470a | 0.397a | |
| 4. Composition D 0-42 | 33.28b | 1.400b | 0.391a | |
| Day 28 | | | | |
| 1. No Additive | 85.59ab | 1.611a | 0.977a | |
| 2. Composition D 0-28 | 81.09b | 1.564a | 0.976a | |
| 3. Composition D 28-42 | 86.30a | 1.615a | 0.975a | |
| 4. Composition D 0-42 | 81.77ab | 1.571a | 0.986a | |
| Day 42 | | | | |
| 1. No Additive | 191.42a | 1.818a | 2.186a | 8.2a |
| 2. Composition D 0-28 | 182.99a | 1.772b | 2.223a | 10.9a |
| 3. Composition D 28-42 | 190.18a | 1.763b | 2.243a | 7.6a |
| 4. Composition D 0-42 | 180.86a | 1.737c | 2.239a | 10.6a |

"D" = days; letters "a," "b," and "c" are used to indicate break points based on statistical analysis and thereby provide an indication of statistically significant differences between observed values.

TABLE 10

| Treatment | E.A. | E.T. | E.M. | Total |
|---|---|---|---|---|
| Day 21 OPG | | | | |
| 1. No Additive | 687a | 335a | 402a | 1424a |
| 2. Composition D 0-28 | 109b | 75a | 151ab | 335b |
| 3. Composition D 28-42 | 419ab | 268a | 260ab | 946ab |
| 4. Composition D 0-42 | 142b | 126a | 67b | 335b |
| Day 28 OPG | | | | |
| 1. No Additive | 7596a | 7270a | 3928a | 18794a |
| 2. Composition D 0-28 | 4023a | 4447a | 1625a | 10095a |
| 3. Composition D 28-42 | 5712a | 6214a | 3216a | 15142ab |
| 4. Composition D 0-42 | 3576a | 5151a | 1759a | 10486b |

"D" = days; "E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

TABLE 11

| Treatment | E.A. | E.M. | E.T. | Total |
|---|---|---|---|---|
| Day 21 Lesion Scores | | | | |
| 1. No Additive | 0.7a | 0.2a | 0.4a | 0.4a |
| 2. Composition D 0-28 | 0.8a | 0.3a | 0.1a | 0.4a |
| 3. Composition D 28-42 | 0.6a | 0.3a | 0.3a | 0.4a |
| 4. Composition D 0-42 | 0.8a | 0.4a | 0.3a | 0.5a |
| Day 28 Lesion Scores | | | | |
| 1. No Additive | 0.3a | 0.1a | 0.0a | 0.1a |
| 2. Composition D 0-28 | 0.3a | 0.3a | 0.0a | 0.2a |
| 3. Composition D 28-42 | 0.4a | 0.2a | 0.0a | 0.2a |
| 4. Composition D 0-42 | 0.4a | 0.2a | 0.0a | 0.2a |
| Day 35 Lesion Scores | | | | |
| 1. No Additive | 0.6a | 0.4a | 0.2a | 0.4a |
| 2. Composition D 0-28 | 0.4a | 0.3a | 0.0a | 0.3a |
| 3. Composition D 28-42 | 0.6a | 0.4a | 0.1a | 0.3a |
| 4. Composition D 0-42 | 0.5a | 0.3a | 0.2a | 0.3a |

"D" = days; "E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

Example 8

In this example, the ability of exemplary compositions to improve bird performance under challenge conditions was determined. In some embodiments, an exemplary composition was administered alone and in other embodiments, it was administered in combination with Salinomycin. In some embodiments, the birds were not fed any additives (that is, neither the composition nor Salinomycin) and in other embodiments the birds were solely fed Salinomycin. The birds used in this example were exposed to ionophore tolerant coccidia in the litter of all pens, beginning from day of age. At day 18, Salinomycin alone did not improve performance. Both treatments with the composition (composition alone and composition and Salinomycin), however, exhibited statistically significant improvements in adjusted feed conversion rates, thus indicating that the composition, alone or in combination with Salinomycin, can control coccidia and improve performance. In yet some embodiments, the combination of the composition and Salinomycin exhibited performance improvements at later stages (e.g., after 28 days, even up to 42 days), indicating a synergistic relationship between the composition and the antibiotic. The oocyst data obtained from this example further corroborates the effectiveness of the composition and the combination of the composition and Salinomycin, as statistically significant reductions in oocyst production were observed. The results from this example further illustrate that the disclosed compositions and combinations are effective to better control coccidia that are partially resistant to ionophores.

TABLE 12

| | Feed Intake | Adj. FCR | Wt. Gain | Mortality |
|---|---|---|---|---|
| Day 18 | | | | |
| 1. No Feed Additive | 25.29a | 1.456a | 0.294a | |
| 2. Composition 250 ppm | 25.02a | 1.358bc | 0.313a | |
| 3. Salinomycin (SAL) 66 ppm | 24.76a | 1.420ab | 0.294a | |
| 4. Composition 250 ppm + SAL 66 ppm | 25.42a | 1.321c | 0.328a | |
| Day 28 | | | | |
| 1. No Feed Additive | 72.26a | 1.712a | 0.792b | |
| 2. Composition 250 ppm | 74.06a | 1.641b | 0.855a | |
| 3. Salinomycin (SAL) 66 ppm | 74.09a | 1.619b | 0.875a | |
| 4. Composition 250 ppm + SAL 66 ppm | 74.81a | 1.566c | 0.909a | |
| Day 42 | | | | |
| 1. No Feed Additive | 177.32a | 1.843a | 2.009b | 3.8ab |
| 2. Composition 250 ppm | 180.19a | 1.796b | 2.108a | 4.9ab |
| 3. Salinomycin (SAL) 66 ppm | 175.68a | 1.773bc | 2.114a | 6.5a |
| 4. Composition 250 ppm + SAL 66 ppm | 178.18a | 1.747c | 2.141a | 3.5b |

TABLE 13

| Treatment | E.A. | E.M. | E.T. | Total |
|---|---|---|---|---|
| Day 18 Lesion Scores | | | | |
| 1. No Feed Additive | 1.5a | 1.1a | 1.0a | 1.2a |
| 2. Composition 250 ppm | 1.5a | 0.8a | 0.4b | 0.9b |
| 3. Salinomycin (SAL) 66 ppm | 1.3a | 0.7a | 0.5b | 0.8b |
| 4. Composition 250 ppm + SAL 66 ppm | 1.7a | 0.9a | 0.2b | 0.9b |
| Day 28 Lesion Scores | | | | |
| 1. No Feed Additive | 1.5a | 1.0a | 0.8a | 1.1a |
| 2. Composition 250 ppm | 0.8b | 0.5b | 0.2b | 0.5b |
| 3. Salinomycin (SAL) 66 ppm | 1.2ab | 0.5b | 0.1b | 0.6b |
| 4. Composition 250 ppm + SAL 66 ppm | 1.0b | 0.3b | 0.3b | 0.6b |

"E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

TABLE 14

| Treatment | E.A. | E.M. | E.T. | Total |
|---|---|---|---|---|
| Day 21 OPG | | | | |
| 1. No Feed Additive | 8191a | 3719a | 6332a | 18241a |
| 2. Composition 250 ppm | 5025b | 2864ab | 3819b | 11708b |
| 3. Salinomycin (SAL) 66 ppm | 2915bc | 1910bc | 5528a | 10352b |
| 4. Composition 250 ppm + SAL 66 ppm | 1508c | 553c | 3719b | 5779c |
| Day 28 OPG | | | | |
| 1. No Feed Additive | 6181a | 2261a | 5477a | 13919a |
| 2. Composition 250 ppm | 5025b | 1457ab | 3467a | 9950b |
| 3. Salinomycin (SAL) 66 ppm | 3819b | 955b | 3065ab | 7839b |
| 4. Composition 250 ppm + SAL 66 ppm | 1558c | 704b | 2161b | 4422c |

"E.A." = *E. acervulina*; "E.M." = *E. maxima*; "E.T." = *E. tenella*; letters "a," "b," and "c" are used to indicate break points based on statistical analysis and thereby provide an indication of statistically significant differences between observed values.

The information provided by Tables 12-14 indicate, in some embodiments, that the disclosed compositions can be used in combination with an antibiotic, antimicrobial, and/or anticoccidial agent to improve performance even in animals that have developed ionophore resistance.

Example 9

In this example, the effect of an exemplary composition comprising *Quillaja saponaria* and *Yucca schidigera* when fed to turkey hens was determined. In some embodiments, the composition was a commercial product sold under the trade name MAGNI-PHI by Phibro Animal Health Corporation. The study comprised 1575 turkeys split into seven blocks of five pens where each pen comprising 45 turkeys. The study was conducted from day 0 to day 42. The five treatments protocols were 0 ppm, 250 ppm, 500 ppm, 750 ppm, and 1000 ppm.

On Days 14, 21, and 28 fresh fecal samples were collected from each pen. These representative samples were tested to determine the degree of coccidia oocysts per gram of litter, by determining oocysts shedding/cycling. Oocysts per gram were determined for each sample. Tables 15 and 16 provide the results. With respect to Table 16, E.G. is *E. gallopavonis*, E.M. is *E. meleagrimitis*, and E.A. is *E. adenoeides*. As can be seen in Table 16, the number of oocysts detected decreased across the groups fed increasing dosages of the composition.

TABLE 15

| Treatments | Feed Intake | Adj. FCR | Avg. Wt Gain |
|---|---|---|---|
| Day 14 | | | |
| 1. 0 ppm Composition D 0-42 | 18.05ab | 1.525ab | 0.220ab |
| 2. 250 ppm Composition D 0-42 | 17.60b | 1.523ab | 0.214b |
| 3. 500 ppm Composition D 0-42 | 19.01a | 1.514ab | 0.236a |
| 4. 750 ppm Composition D 0-42 | 18.26ab | 1.485b | 0.230ab |
| 5. 1000 ppm Composition D 0-42 | 18.65ab | 1.541a | 0.228ab |
| Day 42 | | | |
| 1. 0 ppm Composition D 0-42 | 141.69ab | 1.782a | 1.745bc |
| 2. 250 Composition ppm D0-42 | 136.15b | 1.751ab | 1.705c |
| 3. 500 Composition ppm D 0-42 | 145.08a | 1.754ab | 1.825a |
| 4. 750 Composition ppm D 0-42 | 140.80ab | 1.714b | 1.793ab |
| 5. 1000 Composition ppm D 0-42 | 143.14a | 1.747ab | 1.810ab |

"D" = days; letters "a," "b," and "c" are used to indicate break points based on statistical analysis and thereby provide an indication of statistically significant differences between observed values.

TABLE 16

| Treatments | E.G. | E.M. | E.A. | Total |
|---|---|---|---|---|
| Oocysts per gram fecal material Day 14 | | | | |
| 1. 0 ppm Composition D 0-42 | 172ab | 819a | 1010a | 2001a |
| 2. 250 ppm Composition D 0-42 | 114ab | 1086a | 810a | 2011a |
| 3. 500 ppm Composition D 0-42 | 105b | 858a | 943a | 1906a |
| 4. 750 ppm Composition D 0-42 | 152ab | 918a | 753a | 1820a |
| 5. 1000 ppm Composition D 0-42 | 286a | 772a | 734a | 1791a |
| Oocysts per gram fecal material Day 21 | | | | |
| 1. 0 ppm Composition D 0-42 | 9119a | 19753a | 45127a | 73999a |
| 2. 250 ppm Composition D 0-42 | 8652a | 18666ab | 45070a | 72388a |
| 3. 500 ppm Composition D 0-42 | 12320a | 15827ab | 33236ab | 61383ab |
| 4. 750 ppm Composition D 0-42 | 8623a | 17714ab | 38219ab | 64556ab |
| 5. 1000 ppm Composition D 0-42 | 5269a | 9481b | 54498b | 39248b |
| Oocysts per gram fecal material Day 28 | | | | |
| 1. 0 ppm Composition D 0-42 | 505a | 2020a | 362a | 2887a |
| 2. 250 ppm Composition D 0-42 | 429a | 1953a | 486a | 2868a |
| 3. 500 ppm Composition D 0-42 | 257a | 1639a | 257a | 2153a |
| 4. 750 ppm Composition D 0-42 | 267a | 1391a | 534a | 2192a |
| 5. 1000 ppm Composition D 0-42 | 334a | 1039a | 534a | 1906a |

"D" = days; "E.G." = *E. gallopavonis*; "E.M." = *E. meleagrimitis*; "E.A." = *E. adenoeides*; letters "a," "b," and "c" are used to indicate break points based on statistical analysis and thereby provide an indication of statistically significant differences between observed values.

Example 10

In this examples the effect of a composition comprising *Quillaja saponaria* and *Yucca schidigera* in combination with Monensin was determined. In some embodiments, the composition was a commercial product sold under the trade name MAGNI-PHI by Phibro Animal Health Corporation. Four treatment regimens were used: a control with no medication; 250 ppm of the composition; 68 ppm Monensin; and 250 ppm composition in combination with 68 ppm Monensin.

On Days 14, 21, and 28 fresh fecal samples were collected from each pen. These representative samples were tested to determine the degree of coccidia oocysts per gram of litter, by determining oocysts shedding/cycling. Oocysts per gram were determined for each sample. Table 17 and 18 provide the results. As can be seen in Table 17 and 18, the combination of 250 ppm composition and 68 ppm Monensin resulted in a substantial reduction in the number of oocysts detected, compared to the control and to the composition or Monensin individually.

TABLE 17

| Treatment | Feed Intake | Adj. FCR | Wt. Gain (kg) |
|---|---|---|---|
| Day 14 | | | |
| 1. No Additive | 20.71a | 1.536a | 0.258a |
| 2. 250 ppm Composition D 0-42 | 20.09b | 1.495ab | 0.257a |
| 3. Monensin 68 ppm D 0-42 | 20.04b | 1.473b | 0.261a |
| 4. Composition + Monensin D 0-42 | 19.87b | 1.474b | 0.257a |
| Day 28 | | | |
| 1. No Additive | 52.23a | 1.694a | 0.652b |
| 2. 250 ppm Composition D 0-42 | 52.31a | 1.570b | 0.704a |
| 3. Monensin 68 ppm D 0-42 | 51.81a | 1.562b | 0.703a |
| 4. Composition + Monensin D 0-42 | 53.08a | 1.537b | 0.729a |
| Day 42 | | | |
| 1. No Additive | 125.41b | 1.793a | 1.547c |
| 2. 250 ppm Composition D 0-42 | 127.33ab | 1.731b | 1.616b |
| 3. Monensin 68 ppm D 0-42 | 124.77b | 1.707b | 1.614bc |
| 4. Composition + Monensin D 0-42 | 130.13a | 1.689b | 1.691a |

"D" = days; letters "a," "b," and "c" are used to indicate break points based on statistical analysis and thereby provide an indication of statistically significant differences between observed values.

TABLE 18

| Treatment | *E. gallo.* | *E. mel.* | *E. aden.* | Total |
|---|---|---|---|---|
| Oocysts per gram fecal material D 14 | | | | |
| 1. No Additive | 571a | 1579a | 593ab | 2742a |
| 2. 250 ppm Composition D 0-42 | 363ab | 1164ab | 867a | 2394ab |
| 3. Monensin 68 ppm D 0-42 | 430ab | 786b | 356ab | 1571bc |
| 4. Composition + Monensin D 0-42 | 237b | 519b | 304b | 1060a |

TABLE 18-continued

| Treatment | E. gallo. | E. mel. | E. aden. | Total |
|---|---|---|---|---|
| Oocysts per gram fecal material D 21 | | | | |
| 1. No Additive | 674a | 10405a | 1364a | 12443a |
| 2. 250 ppm Composition D 0-42 | 889a | 5662b | 793b | 7344b |
| 3. Monensin 68 ppm D 0-42 | 623a | 2549c | 237bc | 3409c |
| 4. Composition + Monensin D 0-42 | 515a | 1653c | 185c | 2053c |
| Oocysts per gram fecal material D 28 | | | | |
| 1. No Additive | 259a | 252a | 311a | 823a |
| 2. 250 ppm Composition D 0-42 | 200a | 148ab | 59b | 408b |
| 3. Monensin 68 ppm D 0-42 | 119a | 74b | 29b | 252b |
| 4. Composition + Monensin D 0-42 | 30a | 22b | 15b | 67b |

"D" = days; "E. gallo." = E. gallopavonis; "E. mel." = E. meleagrimitis; "E. aden" = E. adenoeides; letters "a," "b," and "c" are used to indicate break points based on statistical analysis and thereby provide an indication of statistically significant differences between observed values.

Example 11

In this example, the effect of a composition comprising *Quillaja saponaria* and *Yucca schidigera* on Necrotic Enteritis caused by *Clostridium perfringens* in Broiler Chickens was determined. In some embodiments, the composition was a commercial product sold under the trade name MAGNI-PHI by Phibro Animal Health Corporation. The study comprised four treatments shown in Table 19.

TABLE 19

| Treatment | | Coccidial Challenge | *Clostridium perfringens* | Cages/Treatment |
|---|---|---|---|---|
| T1 | Nonmedicated | DOT 14 | No | 8 |
| T2 | Nonmedicated | DOT 14 | DOT 19, 20, and 21 | 8 |
| T3 | 250 ppm Composition (D 0-D 28) | DOT 14 | DOT 19, 20, and 21 | 8 |
| T4 | 500 ppm Composition (D 0-D 28) | DOT 14 | DOT 19, 20, and 21 | 8 |

"D" = day; DOT = day of treatment

All birds were weighed on day of treatment (DOT) 0, 14, 21, and 28. Feed was weighed in on DOT 0 and remaining feed was weighed on DOT 14, 21, and 28. 3. Feed and water were given ad libitum. On DOT 14, all birds were orally inoculated with about 5,000 oocysts of *E. maxima*. Starting on DOT 19, all birds except Treatment 1 were given a broth culture of *C. perfringens* about $10^8$ cfu/ml. The birds were administered a fresh broth culture once daily for 3 days (on DOTs 19, 20, and 21).

On DOT 21, three birds from each cage were selected, sacrificed, weighed, and examined for the degree of presence of Necrotic Enteritis lesions. The scoring was based on a 0 to 3 score, with 0 being normal and 3 being the most severe. Table 20 provides the results.

TABLE 20

| Day 14 Treatment | Feed Intake | Adj. FCR | Wt. Gain |
|---|---|---|---|
| 1. No Additive, No CP | 3.316a | 1.663a | 0.242a |
| 2. No Additive, CP | 3.065ab | 1.658a | 0.226a |
| 3. 250 ppm Composition, CP | 2.885b | 1.521b | 0.232a |
| 4. 500 ppm Composition, CP | 3.213ab | 1.597ab | 0.244a |

| | Feed Intake | | Feed Conversion | | Weight Gain (kg) | |
|---|---|---|---|---|---|---|
| Treatment | D 0-21 | D 14-21 | D 0-21 | D 14-21 | D 0-21 | D 14-21 |
| 1. No Additive, No CP | 6.211a | 2.895a | 2.062b | 1.964b | 0.378a | 0.185a |
| 2. No Additive, CP | 5.906ab | 2.841a | 2.312a | 2.516a | 0.332a | 0.151b |
| 3. 250 ppm Composition, CP | 5.519b | 2.634a | 2.054b | 2.215ab | 0.351a | 0.165ab |
| 4. 500 ppm Composition, CP | 6.137a | 2.924a | 2.094b | 2.147b | 0.369a | 0.174ab |

| | Feed Intake | | Feed Conversion | | Weight Gain (kg) | |
|---|---|---|---|---|---|---|
| Treatment | D 0-28 | D 14-28 | D 0-28 | D 14-28 | D 0-28 | D 14-28 |
| 1. No Additive, No CP | 8.372a | 5.057a | 1.950b | 1.834b | 0.652a | 0.460a |
| 2. No Additive, CP | 7.720ab | 4.655a | 2.212a | 2.265a | 0.530a | 0.349b |
| 3. 250 ppm Composition, CP | 7.355b | 4.470a | 1.939b | 1.945b | 0.638a | 0.452ab |
| 4. 500 ppm Composition, CP | 8.093ab | 4.881a | 1.934b | 1.858b | 0.627a | 0.432ab |

| Treatment | Necrotic Enteritis Lesion | % NE Mortality |
|---|---|---|
| 1. No Additive, No CP | 0.0b | 0.0b |
| 2. No Additive, CP | 0.6a | 9.4a |
| 3. 250 ppm Composition, CP | 0.6a | 1.6ab |
| 4. 500 ppm Composition, CP | 0.5a | 4.7ab |

"D" = days; "CP" = *C. perfringens*; "NE" = Necrotic Enteritis; letters "a," "b," and "c" are used to indicate break points based on statistical analysis and thereby provide an indication of statistically significant differences between observed values.

Example 12

In this example, the effect of a composition comprising *Quillaja saponaria* and *Yucca schidigera* on *Cochlosoma anatis* infections in turkeys was determined. In some embodiments, the composition was a commercial product sold under the trade name MAGNI-PHI by Phibro Animal Health Corporation. To assess the efficacy of the composition, birds were treated with 0 (negative and positive controls), 250, 500, 750 and 1000 ppm of the composition beginning on the day-of-hatch. The turkeys were then challenged with about $1 \times 10^6$ *Cochlosoma anatis* trophozoites by oral gavage at age 10 days. Twenty nine birds were left untreated and unchallenged to serve as a negative control. At age 13 and 16 days (3 and 6 days post-challenge), birds were euthanized and samples collected.

Results

Mortality:

Mortality was collected pre- and post-challenge (Table 21). High mortality was observed in the 250 ppm (10.3%) and 750 ppm (24.1%) MP groups pre-challenge; however, there was no mortality for these groups post-challenge. Post-mortem exams indicated that the mortality was primarily attributed to a failure to consume food (i.e. starve-outs).

TABLE 21

| Treatment | Mortality Pre-Challenge (1-10 days) | Mortality Post-Challenge (11-16 days) | Total |
|---|---|---|---|
| Negative | 0 | 0 | 29 |
| Positive | 1 | 0 | 29 |
| 250 ppm | 3 | 0 | 29 |
| 500 ppm | 0 | 0 | 29 |
| 750 ppm | 7 | 0 | 29 |
| 1000 ppm | 0 | 1 | 29 |

Figure 46:
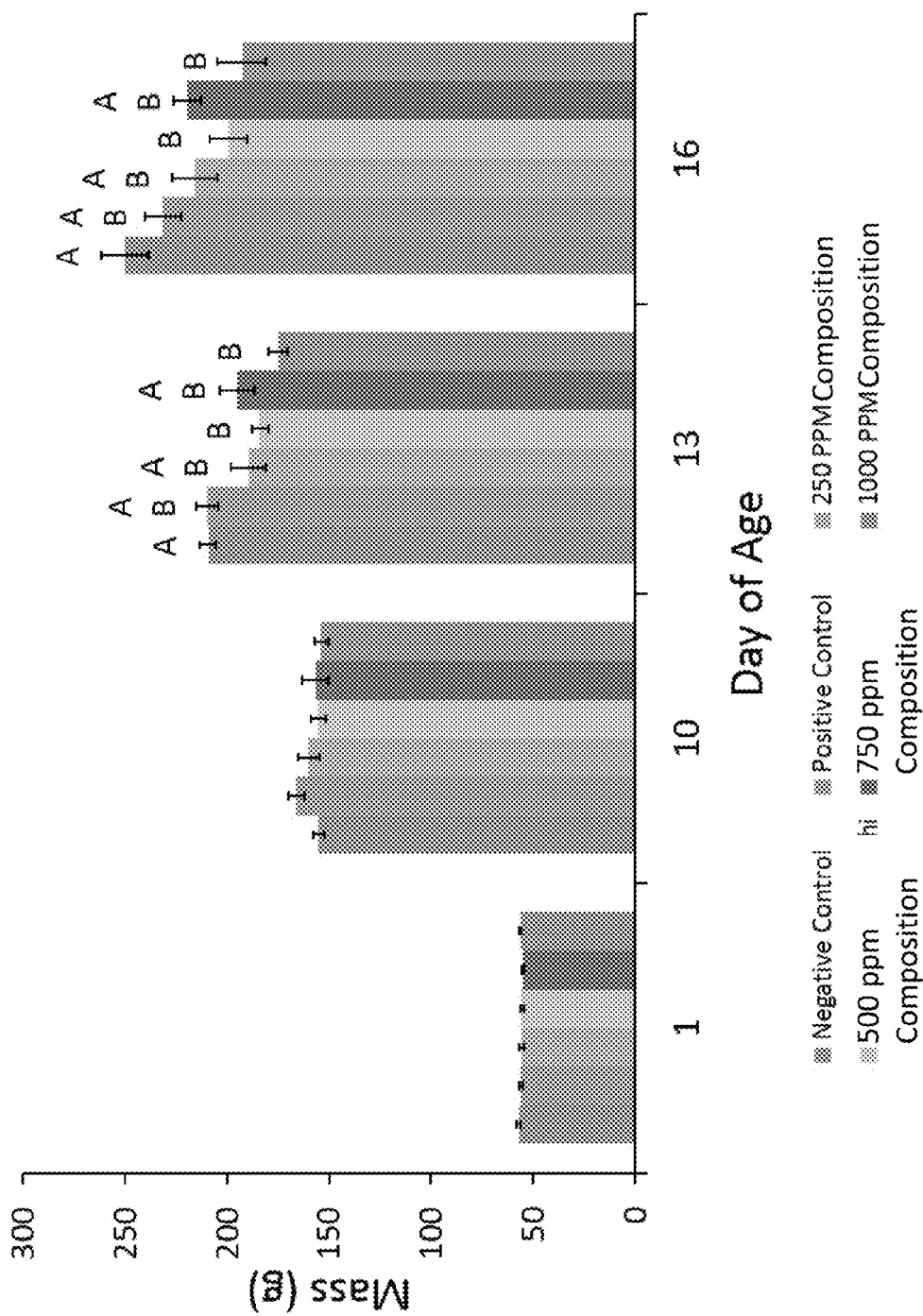
FIG. 46 is a graph of body weight versus age in days, illustrating the different changes in body weight for the different treatment groups over time.

Body Weight:

Body weights were collected before challenge (age 1 and 10 days) and after challenge (age 13 and 16 days). A significant decrease in body weight was observed at age 13 and 16 days for the 500 ppm and 1000 ppm treated groups when compared to the negative control group (FIG. 46). However, no significant differences were observed for these ages or treatment groups when compared to the positive control group. With reference to FIG. 46, treatments not connected by the same letter are significantly different.

Figure 47:
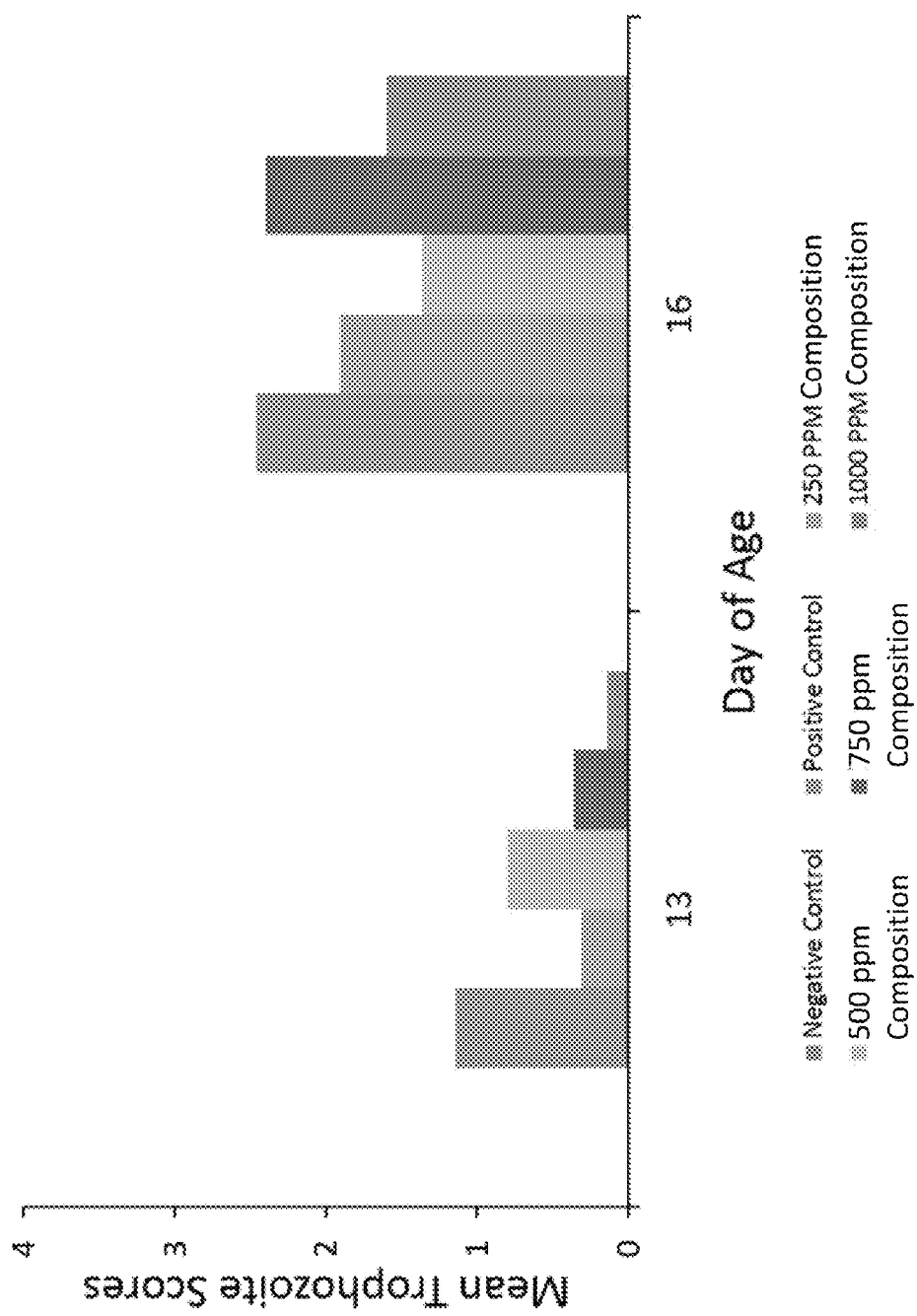
FIG. 47 is a graph of mean trophozoite score versus age in days, illustrating a general dose dependent reduction of trophozoite score for groups administered a composition comprising *Quillaja saponaria* and *Yucca schidigera*.

Trophozoite Scores:

Gastrointestinal samples were collected at meckel's diverticulum and scored for the prescence of trophozoites (0=0 trophozoites, 1=1-10 trophozoites, 2=11-50 trophozoites, 3=50-100 trophozoites, 4=>100 trophozoites). There appeared to be a dose dependent reduction in the trophozoite score for composition-treated birds at both 13 (3 days PI) and 16 (6 days PI) days of age (FIG. 47). There was a significant decrease in the the number of trophozoites for the 1000 ppm treated group when compared to the positive control at age 13 days (Table 22). There were no significant differences at age 16 days, however, the data indicates that the median trophozoite scores are trending lower for the composition-treated birds when compared to the positive control birds (Table 23).

TABLE 22

Trophozoite Scores - age 13 days
Wilcoxon/Kruskal-Wallis Test (Rank Sums) P = 0.0334

| Treatment | Min-Max | Median | P-value (Dunn's) |
|---|---|---|---|
| Positive | 0-4 | 1 | — |
| 250 ppm | 0-3 | 0 | 0.0868 |
| 500 ppm | 0-3 | 0 | 1.0000 |
| 750 ppm | 0-3 | 0 | 0.16141 |
| 1000 ppm | 0-1 | 0 | 0.0438 |

TABLE 23

Trophozoite Scores - age 16 days
Wilcoxon/Kruskal-Wallis Test (Rank Sums) P = 0.2895

| Treatment | Min-Max | Median | P-value (Dunn's) |
|---|---|---|---|
| Positive | 0-4 | 4 | — |
| 250 ppm | 0-4 | 2 | — |
| 500 ppm | 0-4 | 1 | — |
| 750 ppm | 0-4 | 2.5 | — |
| 1000 ppm | 0-4 | 1 | — |

Figure 48:
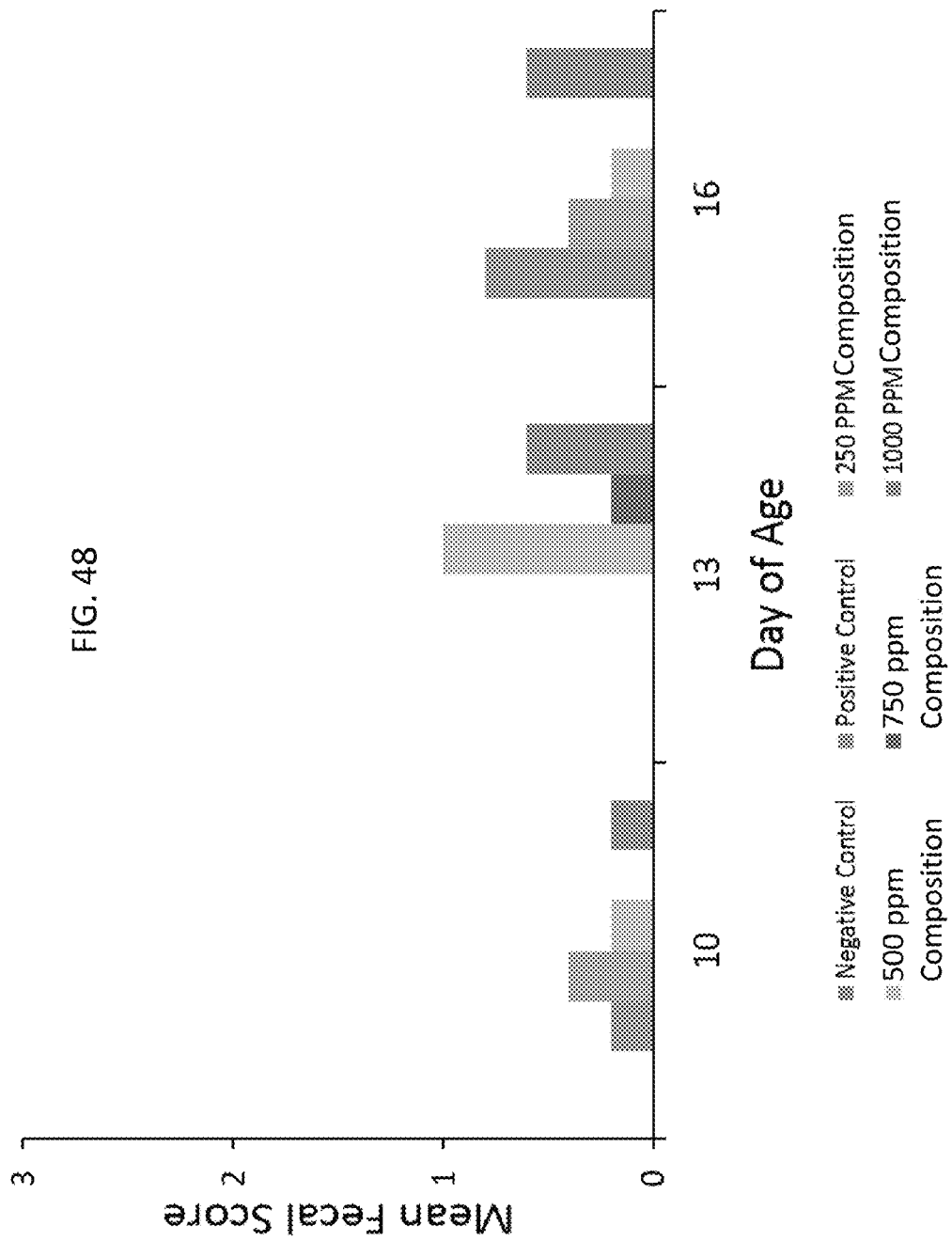
FIG. 48 is a graph of mean fecal score versus age in days, illustrating the different amounts of enteritis detected in fecal samples for the different treatment groups over time.

Fecal Scores:

Fecal samples were collected from five birds selected at random by placing the birds on a clean surface and waiting until they defecated. Theses samples were then scored for enteritits (0=firm fecal sample, 1=lose fecal sample, 2=moderate diarrhea, 3=severe diarrhea). At age 10 and 13 days, minimal enteritis was observed, but by age 16 days, moderate to severe enteritis had developed in some birds (FIG. 48). The fecal scores were highly variable and no significant differences were found for the treated groups when compared to the positive control group (Tables 24 and 25).

TABLE 24

Fecal Scores - age 13 days
Wilcoxon/Kruskal-Wallis Test (Rank Sums) P = 0.1381

| Treatment | Min-Max | Median | P-value (Dunn's) |
|---|---|---|---|
| Positive | 0-0 | 0 | — |
| 250 ppm | 0-0 | 0 | — |
| 500 ppm | 0-2 | 1 | — |
| 750 ppm | 0-1 | 0 | — |
| 1000 ppm | 0-3 | 0 | — |

TABLE 25

Fecal Scores - age 16 days
Wilcoxon/Kruskal-Wallis Test (Rank Sums) P = 0.5920

| Treatment | Min-Max | Median | P-value (Dunn's) |
|---|---|---|---|
| Positive | 0-3 | 0 | — |
| 250 ppm | 0-1 | 0 | — |
| 500 ppm | 0-1 | 0 | — |
| 750 ppm | 0-0 | 0 | — |
| 1000 ppm | 0-3 | 0 | — |

Figure 49:
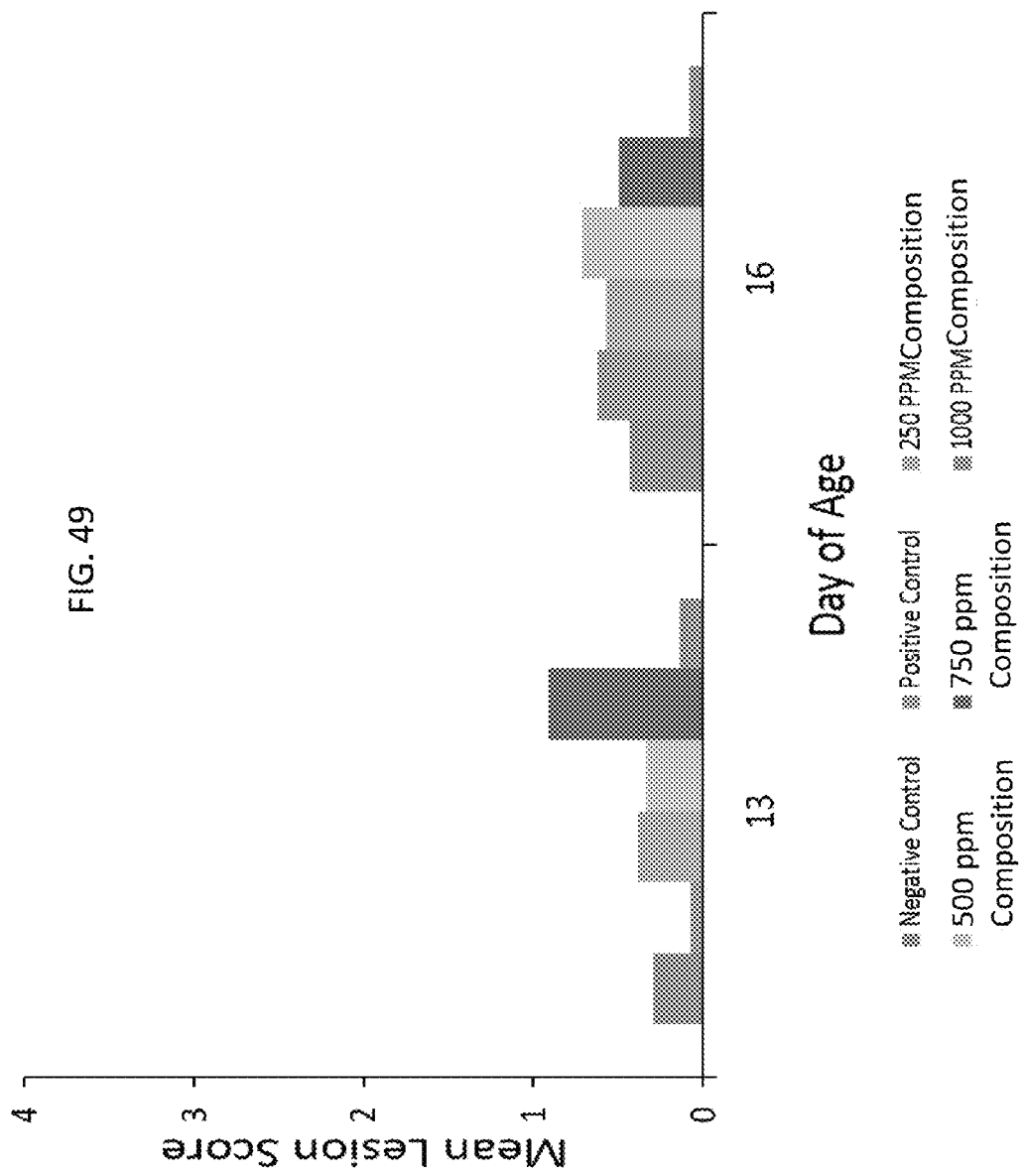
FIG. 49 is a graph of mean lesion score versus age in days, illustrating the duodenal lesion score for the different treatment groups at days 13 and 16.
Figure 50:
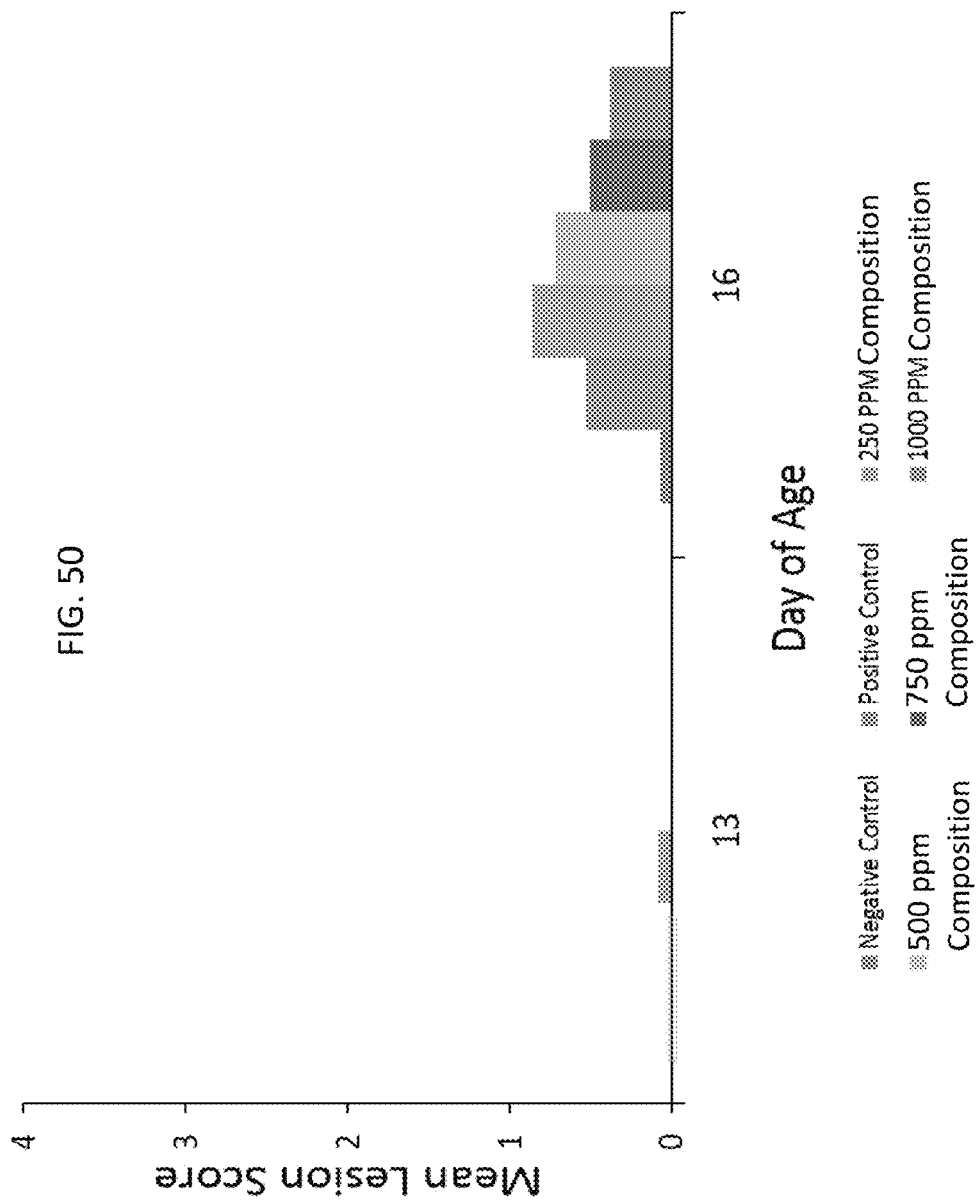
FIG. 50 is a graph of mean lesion score versus age in days, illustrating the jejunal lesion score for the different treatment groups at days 13 and 16.
Figure 51:
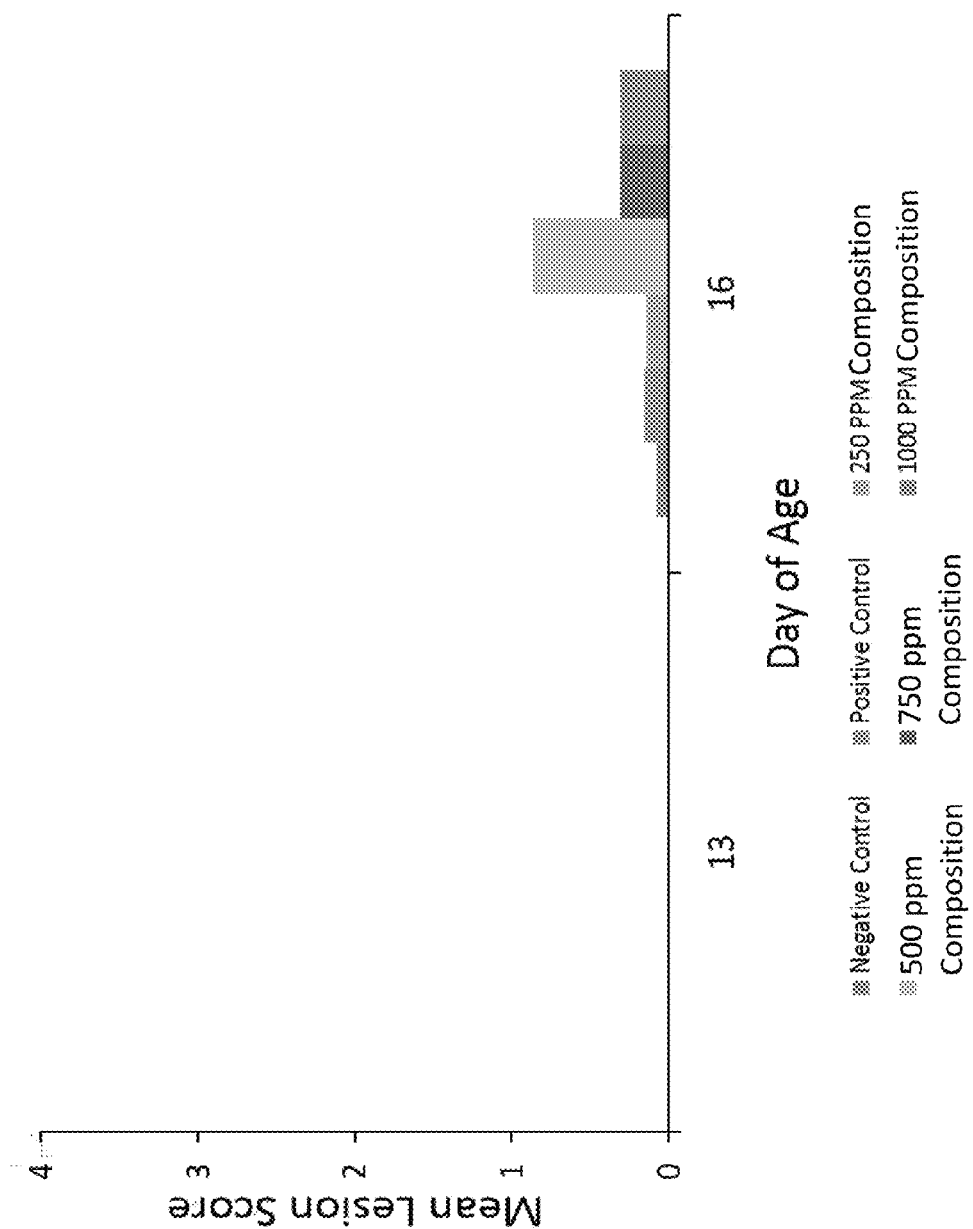
FIG. 51 is a graph of mean lesion score versus age in days, illustrating the ileal lesion score for the different treatment groups at days 13 and 16.

Intestinal Lesion Scores:

Sections of the small intestine were scored for necrotic lesions and inflammation associated with enteritis (0=no lesions, 1=1-2 focal lesions, 2=2-5 focal lesions, 3=moderately coalescing lesions, 4=severely coalescing lesions). No significant differences were observed for lesions in the duodenum (FIG. 49, Tables 26 and 27) or jejunum (FIG. 50, Tables 28 and 29) at either age 13 or 16 days. In the ileum there was a significant increase in the lesion score at age 16 days for the 500 ppm group compared to the positive control (Dunn's test: P=0.0148), no other significant differences were detected (FIG. 51, Tables 30 and 31).

TABLE 26

Duodenum Scores - age 13 days
Wilcoxon/Kruskal-Wallis Test (Rank Sums) P = 0.2175

| Treatment | Min-Max | Median | P-value (Dunn's) |
|---|---|---|---|
| Positive | 0-1 | 0 | — |
| 250 ppm | 0-1 | 0 | — |
| 500 ppm | 0-2 | 0 | — |
| 750 ppm | 0-1 | 0 | — |
| 1000 ppm | 0-1 | 0 | — |

TABLE 27

Duodenum Scores - age 16 days
Wilcoxon/Kruskal-Wallis Test (Rank Sums) P = 0.0535

| Treatment | Min-Max | Median | P-value (Dunn's) |
|---|---|---|---|
| Positive | 0-2 | 1 | — |
| 250 ppm | 0-2 | 0 | — |
| 500 ppm | 0-2 | 1 | — |
| 750 ppm | 0-1 | 0.5 | — |
| 1000 ppm | 0-1 | 0 | — |

TABLE 28

Jejunum Scores - age 13 days
Wilcoxon/Kruskal-Wallis Test (Rank Sums) P = 0.3856

| Treatment | Min-Max | Median | P-value (Dunn's) |
|---|---|---|---|
| Positive | 0-0 | 0 | — |
| 250 ppm | 0-1 | 0 | — |
| 500 ppm | 0-0 | 0 | — |
| 750 ppm | 0-0 | 0 | — |
| 1000 ppm | 0-0 | 0 | — |

TABLE 29

Jejunum Scores - age 16 days
Wilcoxon/Kruskal-Wallis Test (Rank Sums) P = 0.7610

| Treatment | Min-Max | Median | P-value (Dunn's) |
|---|---|---|---|
| Positive | 0-3 | 0 | — |
| 250 ppm | 0-2 | 0 | — |
| 500 ppm | 0-2 | 0.5 | — |
| 750 ppm | 0-1 | 0.5 | — |
| 1000 ppm | 0-1 | 0 | — |

TABLE 30

Ileum Scores - age 13 days
Wilcoxon/Kruskal-Wallis Test (Rank Sums) P = 1.000

| Treatment | Min-Max | Median | P-value (Dunn's) |
|---|---|---|---|
| Positive | 0-0 | 0 | — |
| 250 ppm | 0-0 | 0 | — |
| 500 ppm | 0-0 | 0 | — |
| 750 ppm | 0-0 | 0 | — |
| 1000 ppm | 0-0 | 0 | — |

TABLE 31

Ileum Scores - age 16 days
Wilcoxon/Kruskal-Wallis Test (Rank Sums) P = 0.0107

| Treatment | Min-Max | Median | P-value (Dunn's) |
|---|---|---|---|
| Positive | 0-1 | 0 | — |
| 250 ppm | 0-1 | 0 | 1.0000 |
| 500 ppm | 0-2 | 1 | 0.0148 |
| 750 ppm | 0-1 | 0 | 0.9948 |
| 1000 ppm | 0-1 | 0 | 1.0000 |

SUMMARY

Body weights were significantly decreased for the 500 ppm and 1000 ppm composition groups at both age 13 days and 16 days when compared to the negative control; however, a significant decrease was not observed when compared to the positive control. This data indicates that the *C. anatis* challenge resulted in a reduction in body weights. Reduced body weights are observed in naturally infected commercial turkeys and thus highlights the usefulness of this model for assessing potential treatment strategies. At age 13 days, trophozoite scores indicated that the positive control and composition treatment groups were successfully infected. There was also a significant decrease in the trophozoite score for the 1000 ppm group compared to the positive control. This data shows that composition treatment can have an impact on *C. anatis* infections. At 16 days, there were no significant differences in the composition treatment groups compared to the positive control; however, a clear trend was observed which indicated a reduction in trophozoites for composition treated birds. *C. anatis* infected birds developed enteritis following challenge; however, no significant differences were detected for fecal scores from treatment groups when compared to the positive control. For intestinal scores there were no significant differences in the lesions of the doudenum or jejumun of composition treated groups when compared to the positive control group. There was an increase in the lesion scores in the ileum of the 500 ppm treated group compared to the positive control, but since no other differences were observed, the reasons for this increase are difficult to determine. In summary, composition treatment decreased trophozoites in the gastrointestinal tract of turkeys. The composition therefore could be used to reduce the impact of field infections and the trophozoite burden in commercial turkeys.

Example 13

In this example, the effect of a composition comprising *Quillaja saponaria* and *Yucca schidigera* on the microbiome of turkeys was determined. In some embodiments, the composition was a commercial product sold under the trade name MAGNI-PHI by Phibro Animal Health Corporation. To assess the efficacy of the composition microbiome profiling was performed on whole gut samples from turkeys administered the composition. In total, 121 samples were sequenced by amplifying the V4 region of the 16S rRNA target from extracted DNA for each sample. This generated 3,023,527 bp of data with the average number of sequences per sample at 24,987 (range 13,201 to 38,247). Sample were then analyzed using an open reference OTU-picking approach in QIIME followed by analyses in R statistical package.

Results

Figure 52:
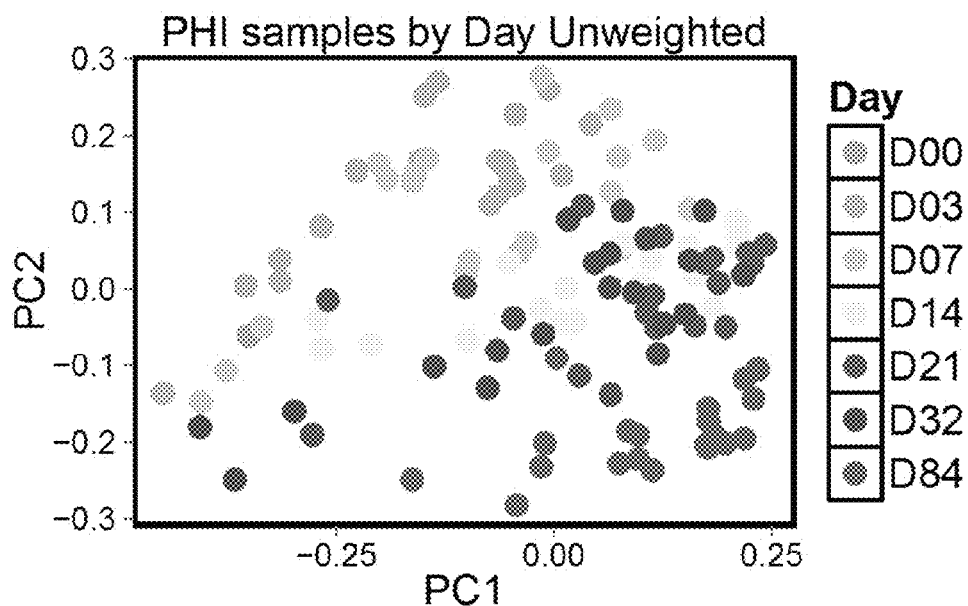
FIG. 52 is a PCoA plot colored by age, illustrating the age-dependent progression of the bacterial community in the gut of the turkeys.

Initially, bird age was examined as a factor in bacterial community composition. As expected, there was a clear age-dependent progression of the bacterial community as illustrated in the PCoA plot in FIG. 52.

Figure 53:
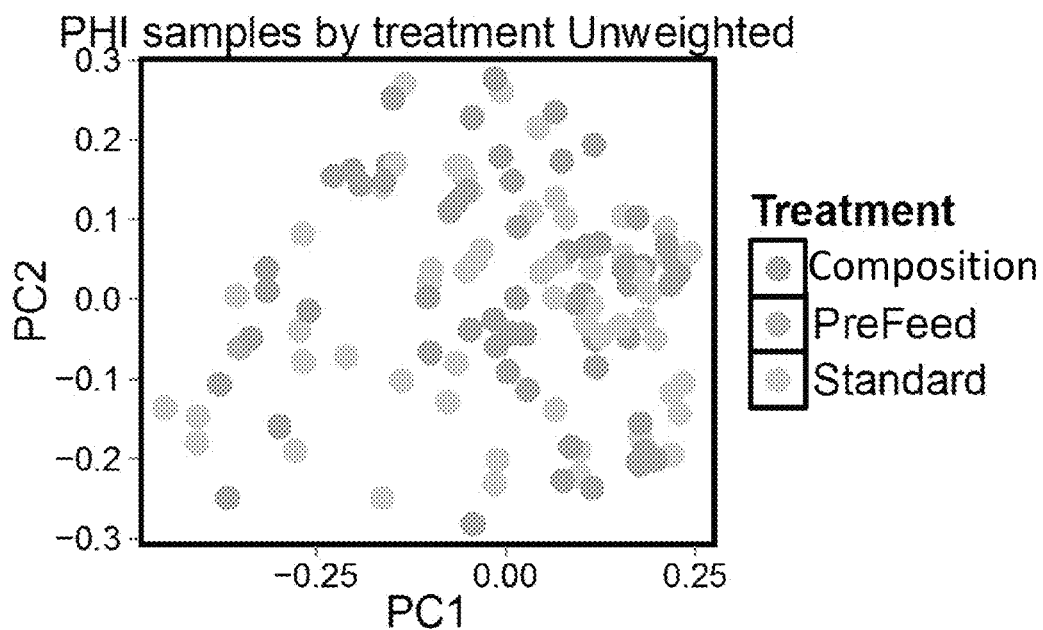
FIG. 53 is a PCoA plot colored by treatment, illustrating the differences between the bacterial communities between control and treatment groups.
Figure 54:
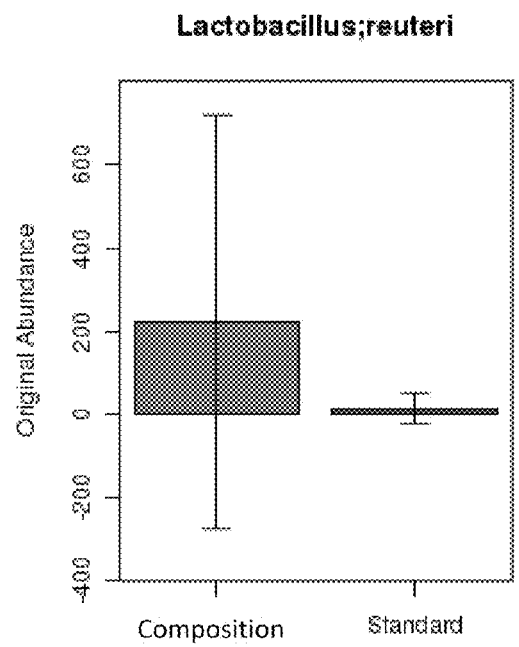
FIG. 54 is a plot of original abundance illustrating the amount of *Lactobacillus reuteri* in the control and treatment groups at day 3.
Figure 55:
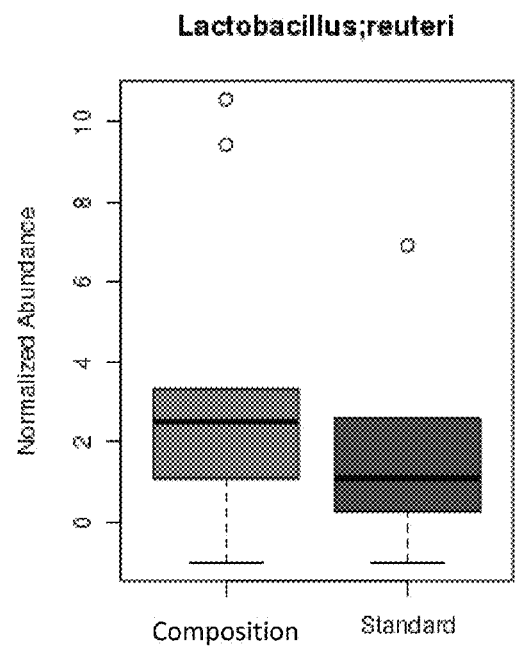
FIG. 55 is a plot of normalized abundance illustrating the amount of *Lactobacillus reuteri* in the control and treatment groups at day 3.
Figure 56:
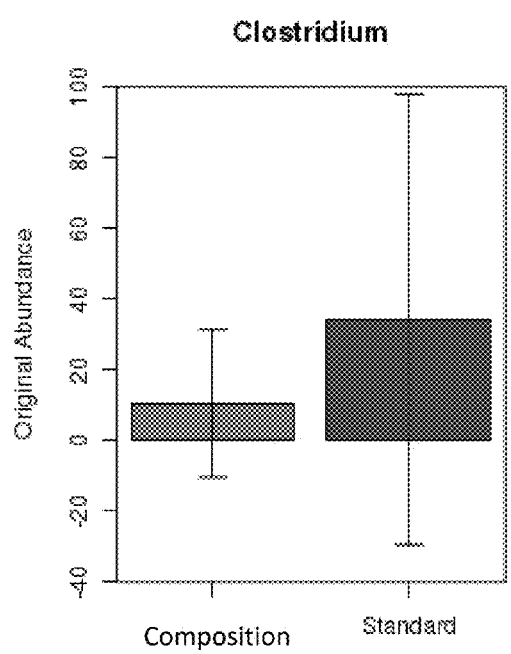
FIG. 56 is a plot of original abundance illustrating the amount of *Clostridium* species in the control and treatment groups at day 3.
Figure 57:
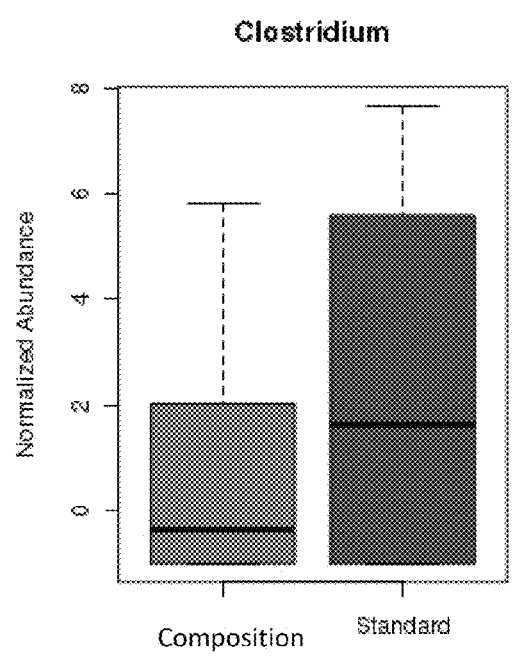
FIG. 57 is a plot of normalized abundance illustrating the amount of *Clostridium* species in the control and treatment groups at day 3.

The same PCoA plot was then colored by treatment instead of by age (FIG. 53). There was not a clear distinction between the bacterial communities between control and treatment groups, indicating that the differences needed to be examined at the individual bacterial species or group level. Differences in taxa were identified between the control group and treatments groups in samples taken on days 3, 7, 14, 21, 32, and 84. On day 3, significant enrichment of *Lactobacillus reuteri* and significant decrease in *Clostridium* species were identified (FIGS. 54-57).

Figure 58:
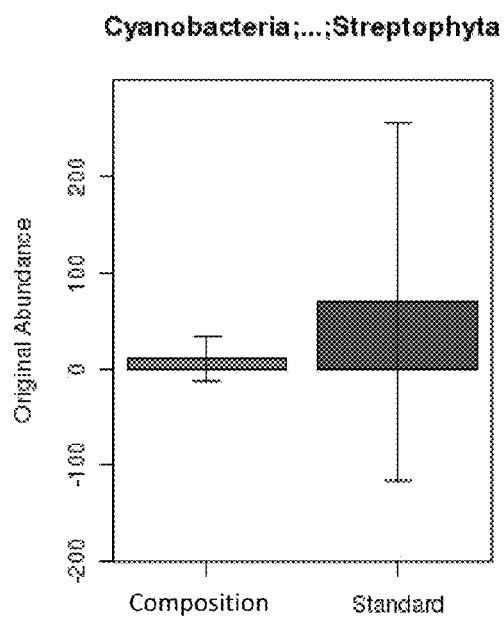
FIG. 58 is a plot of original abundance illustrating the amount of cyanobacterial sequences in the control and treatment groups at day 7.
Figure 59:
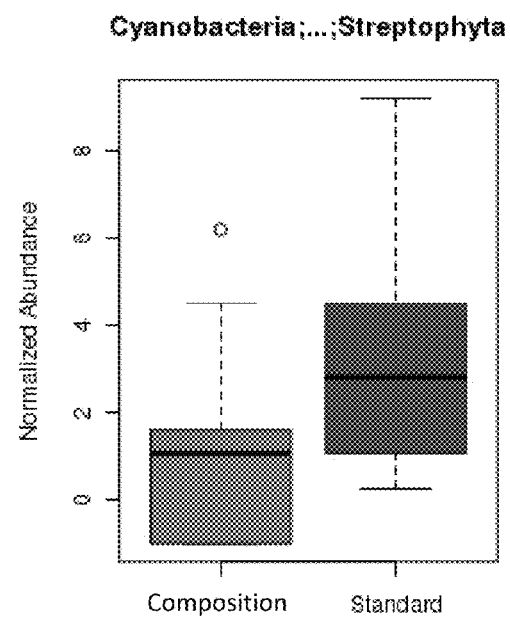
FIG. 59 is a plot of normalized abundance illustrating the amount of cyanobacterial sequences in the control and treatment groups at day 7.
Figure 60:
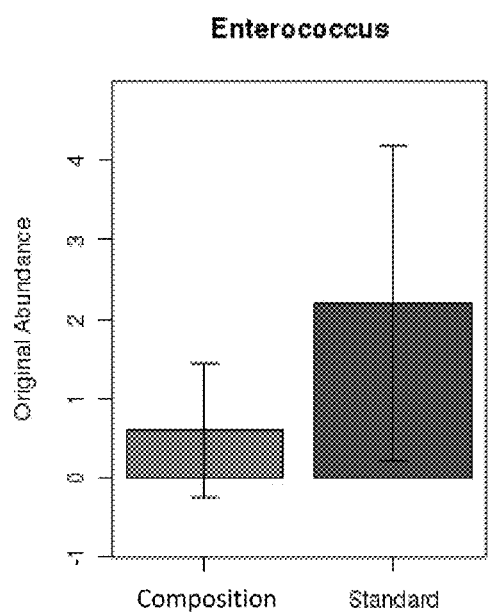
FIG. 60 is a plot of original abundance illustrating the amount of *Enterococcus* species in the control and treatment groups at day 7.
Figure 61:
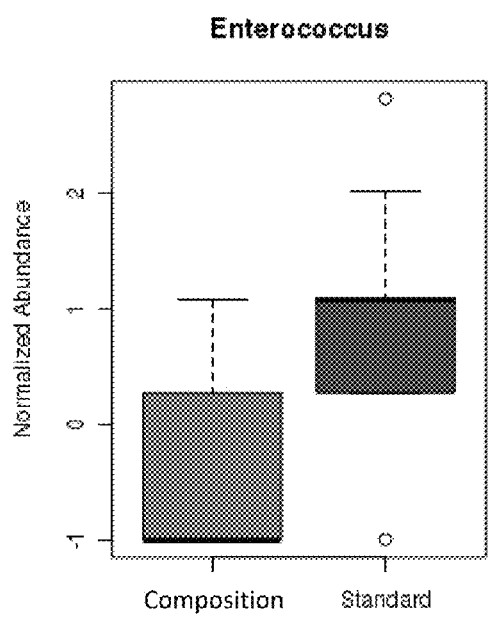
FIG. 61 is a plot of normalized abundance illustrating the amount of *Enterococcus* species in the control and treatment groups at day 7.
Figure 62:
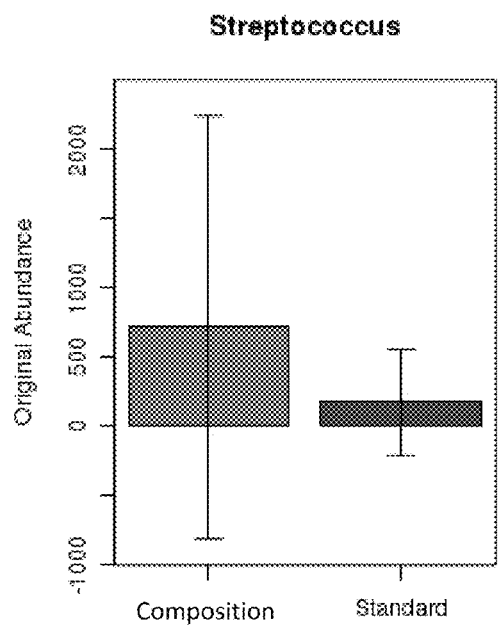
FIG. 62 is a plot of original abundance illustrating the amount of *Streptococcus* species in the control and treatment groups at day 7.
Figure 63:
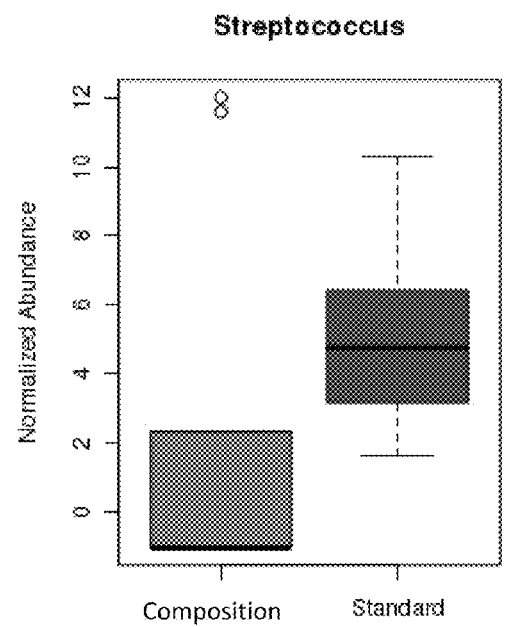
FIG. 63 is a plot of normalized abundance illustrating the amount of *Streptococcus* species in the control and treatment groups at day 7.

At day 7, there were significant decreases in cyanobacterial sequences (FIGS. 58-59), *Enterococcus* species (FIGS. 60 and 61) and *Streptococcus* species (FIGS. 62 and 63). The decrease in cyanobacterial sequences were actually not indicative of cyanobacteria, but rather they indicated that there was undigested feed containing plant materials. Thus, a decrease in the cyanobacterial sequences suggested that there was less undigested feed in the gut at time of sampling in the treatment groups.

Figure 64:
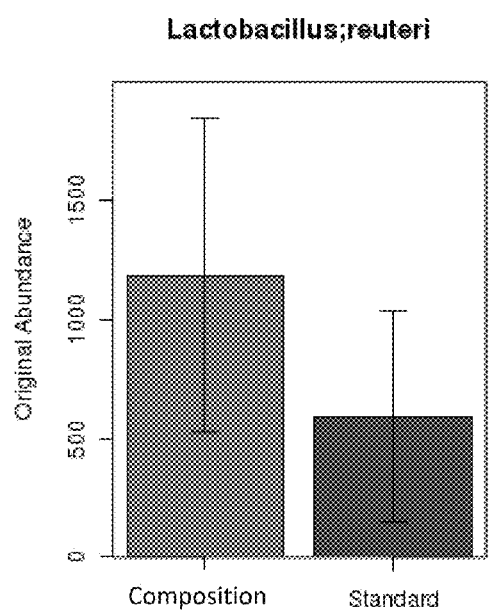
FIG. 64 is a plot of original abundance illustrating the amount of *Lactobacillus reuteri* in the control and treatment groups at day 14.
Figure 65:
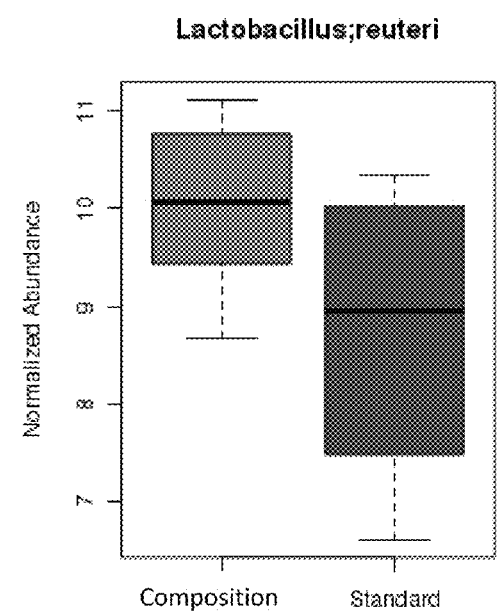
FIG. 65 is a plot of normalized abundance illustrating the amount of *Lactobacillus reuteri* in the control and treatment groups at day 14.
Figure 66:
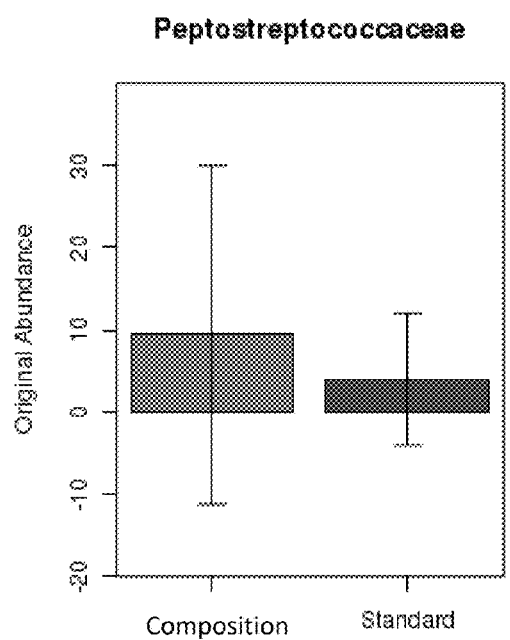
FIG. 66 is a plot of original abundance illustrating the amount of Peptostreptococcaceae in the control and treatment groups at day 14.
Figure 67:
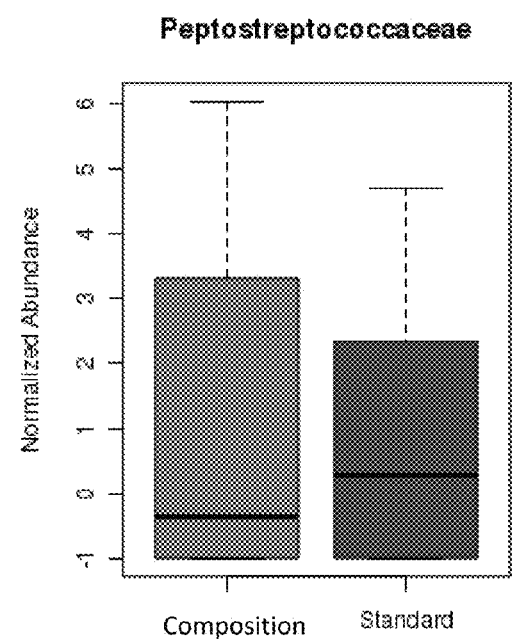
FIG. 67 is a plot of normalized abundance illustrating the amount of Peptostreptococcaceae in the control and treatment groups at day 14.
Figure 68:
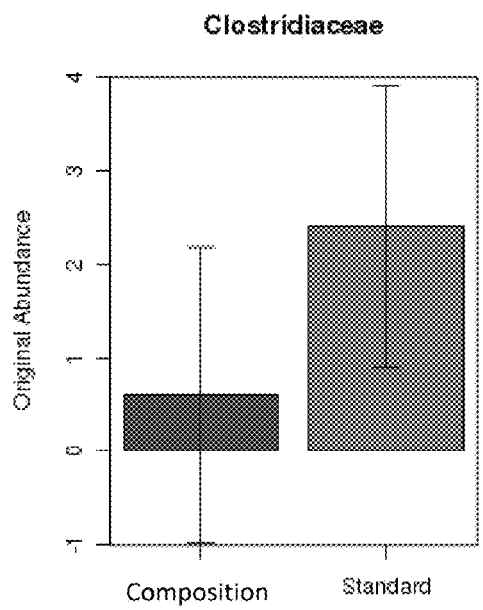
FIG. 68 is a plot of original abundance illustrating the amount of Clostridiaceae in the control and treatment groups at day 21.
Figure 69:
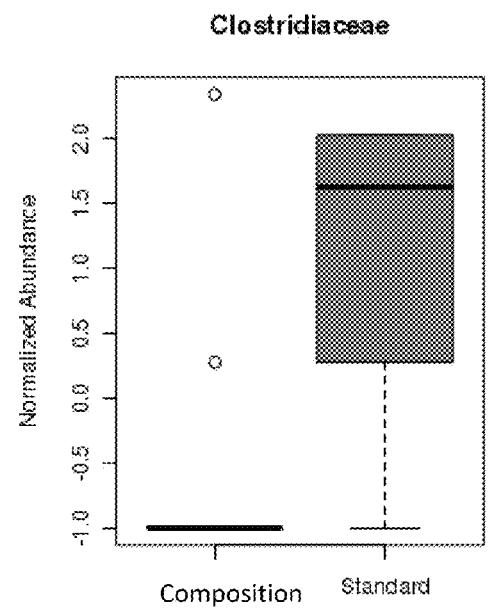
FIG. 69 is a plot of normalized abundance illustrating the amount of Clostridiaceae in the control and treatment groups at day 21.
Figure 70:
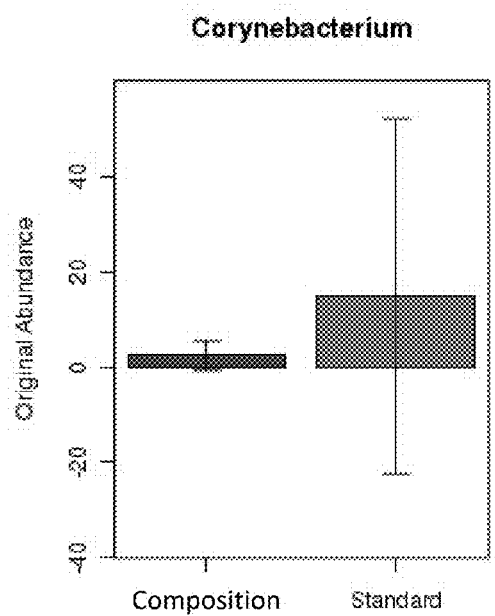
FIG. 70 is a plot of original abundance illustrating the amount of *Corynebacterium* species in the control and treatment groups at day 21.
Figure 71:
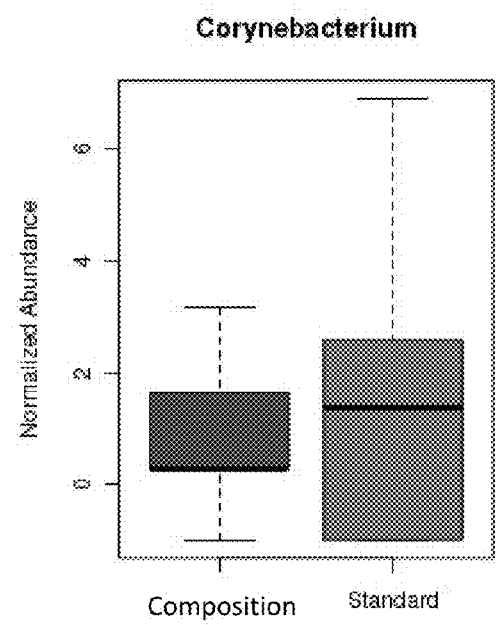
FIG. 71 is a plot of normalized abundance illustrating the amount of *Corynebacterium* species in the control and treatment groups at day 21.
Figure 72:
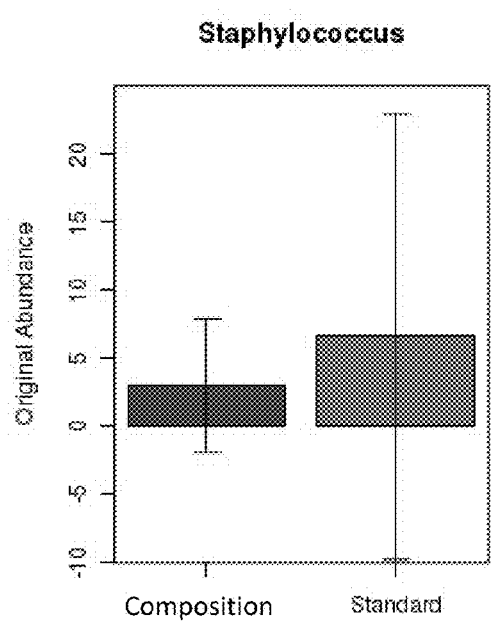
FIG. 72 is a plot of original abundance illustrating the amount of *Staphylococcus* species in the control and treatment groups at day 21.
Figure 73:
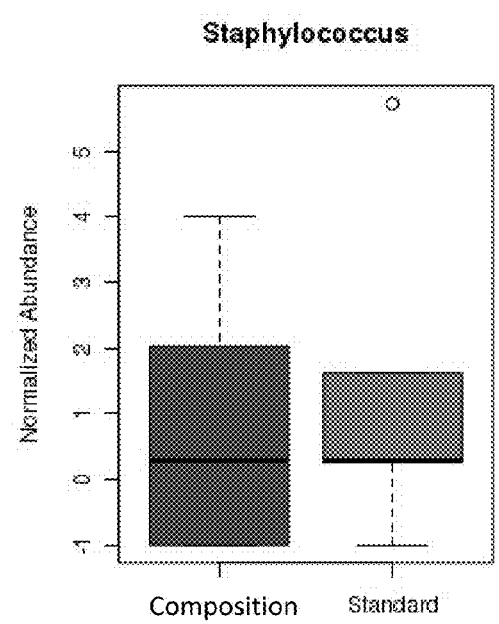
FIG. 73 is a plot of normalized abundance illustrating the amount of *Staphylococcus* species in the control and treatment groups at day 21.
Figure 74:
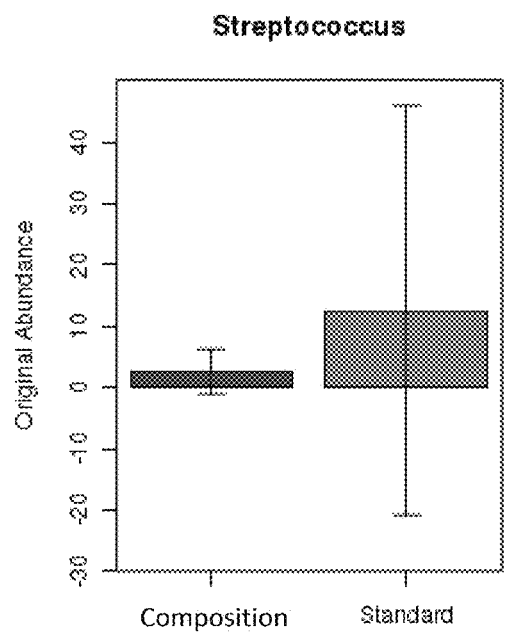
FIG. 74 is a plot of original abundance illustrating the amount of *Streptococcus* species in the control and treatment groups at day 21.
Figure 75:
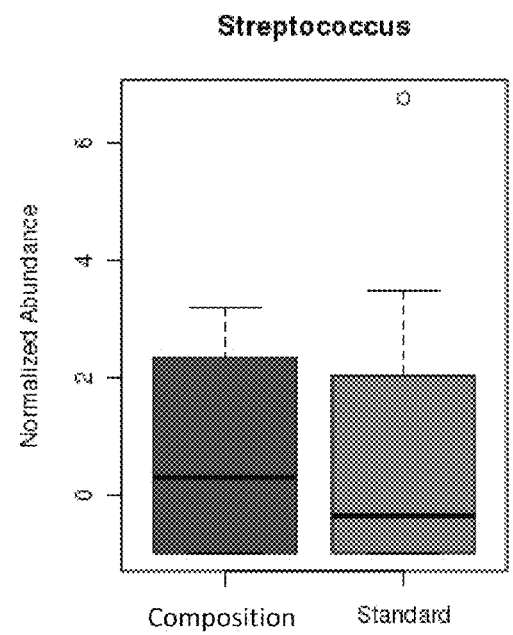
FIG. 75 is a plot of normalized abundance illustrating the amount of *Streptococcus* species in the control and treatment groups at day 21.

At day 14, a significant increase in *Lactobacillus reuteri* was again observed in the treatment group (FIGS. 64 and 65). Additionally, there was a significant enrichment in Peptostreptococcaceae, which includes butyrate producing bacteria that have been shown to be positively correlated with improved gut health (FIGS. 66 and 67).

Figure 76:
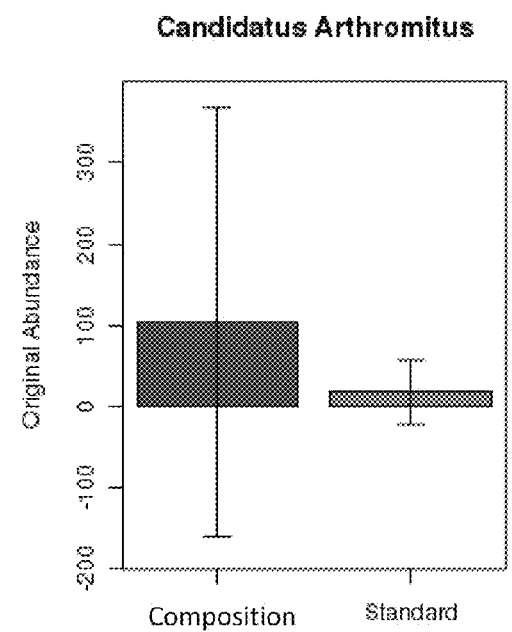
FIG. 76 is a plot of original abundance illustrating the amount of *Candidatus Arthromitus* in the control and treatment groups at day 21.
Figure 77:
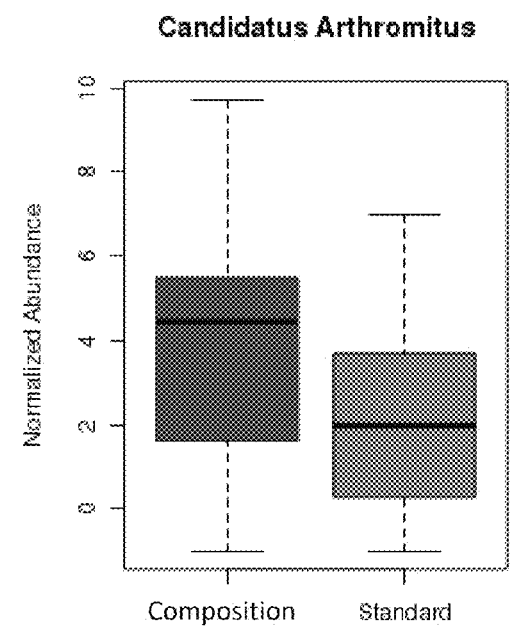
FIG. 77 is a plot of normalized abundance illustrating the amount of *Candidatus Arthromitus* in the control and treatment groups at day 21.

At day 21, significant decreases in Clostridiaceae, *Corynebacterium* species, *Staphylococcus* species, and *Streptococcus* species (FIGS. 68-75) were observed, all of which contain pathogenic species of bacteria. In contrast, a significant increase in segmented filamentous bacteria (*Candidatus Arthromitus*) was detected (FIGS. 76 and 77). The earlier appearance of *Candidatus Arthromitus* in turkey flocks has been a strong biomarker of enhanced performance, so the earlier appearance and higher abundance of this bacteria in the treatment groups suggested enhance performance and accelerate maturation of the microbiota in the treatment birds.

Figure 78:
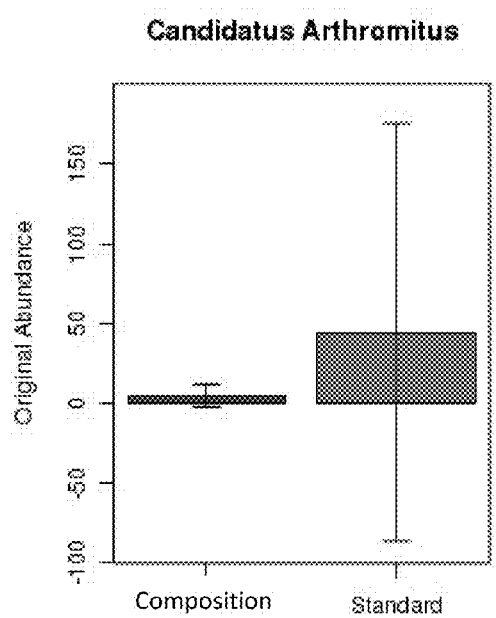
FIG. 78 is a plot of original abundance illustrating the amount of *Candidatus Arthromitus* in the control and treatment groups at day 32.
Figure 79:
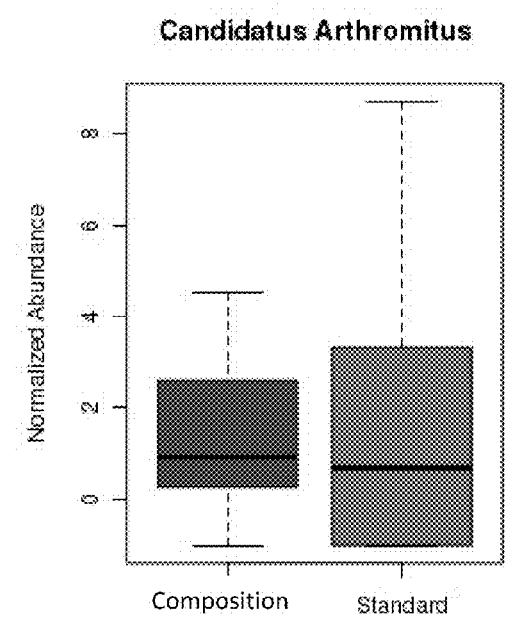
FIG. 79 is a plot of normalized abundance illustrating the amount of *Candidatus Arthromitus* in the control and treatment groups at day 32.
Figure 80:
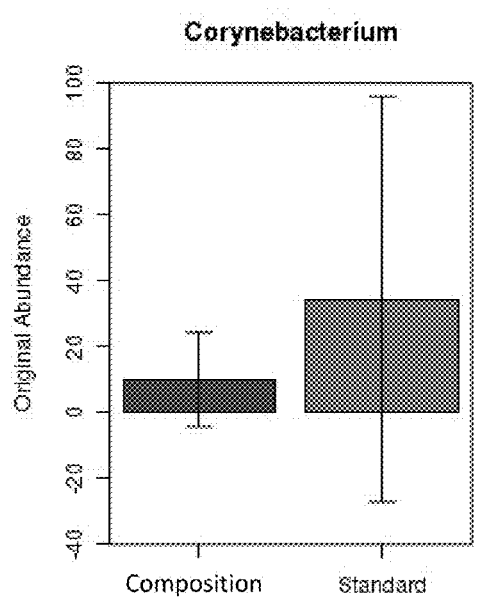
FIG. 80 is a plot of original abundance illustrating the amount of *Corynebacterium* species in the control and treatment groups at day 32.
Figure 81:
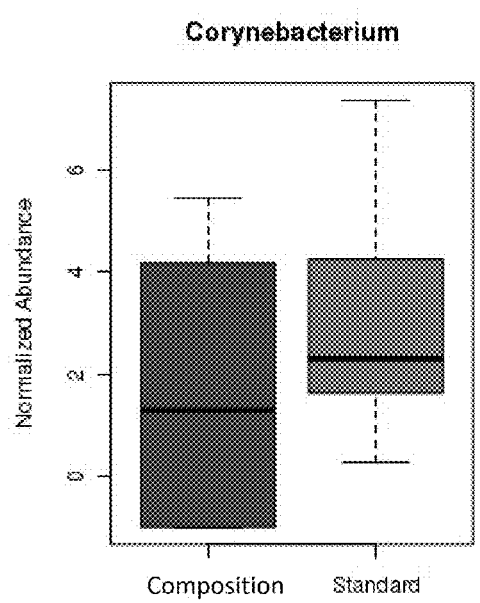
FIG. 81 is a plot of normalized abundance illustrating the amount of *Corynebacterium* species in the control and treatment groups at day 32.
Figure 82:
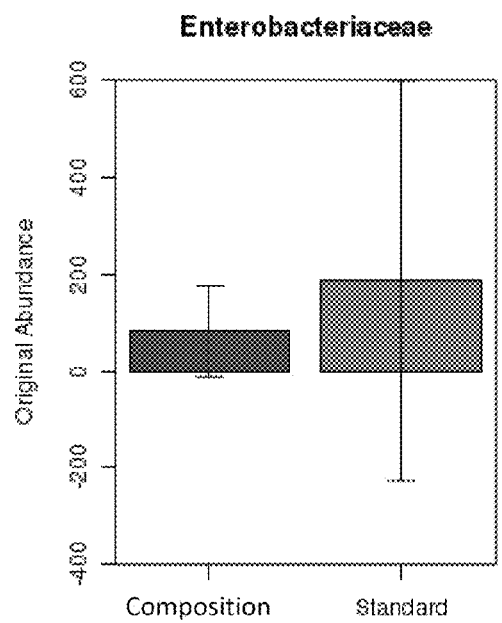
FIG. 82 is a plot of original abundance illustrating the amount of *E. coli* in the control and treatment groups at day 32.
Figure 83:
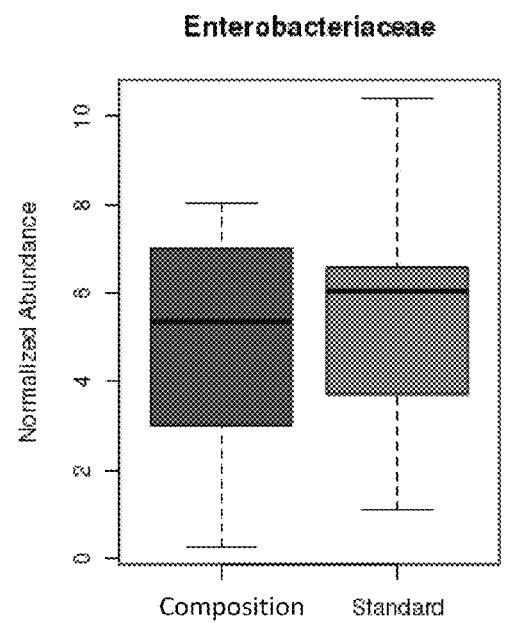
FIG. 83 is a plot of normalized abundance illustrating the amount of *E. coli* in the control and treatment groups at day 32.
Figure 84:
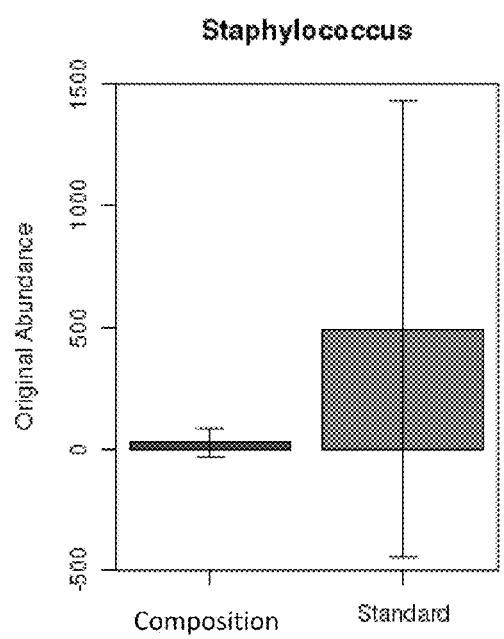
FIG. 84 is a plot of original abundance illustrating the amount of *Staphylococcus* species in the control and treatment groups at day 32.
Figure 85:
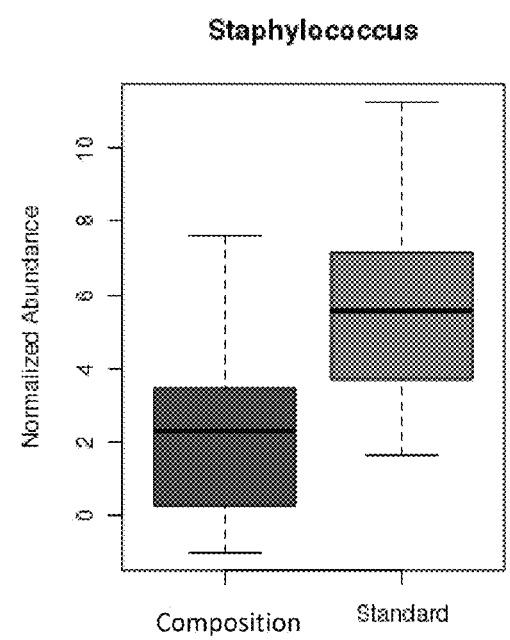
FIG. 85 is a plot of normalized abundance illustrating the amount of *Staphylococcus* species in the control and treatment groups at day 32.
Figure 86:
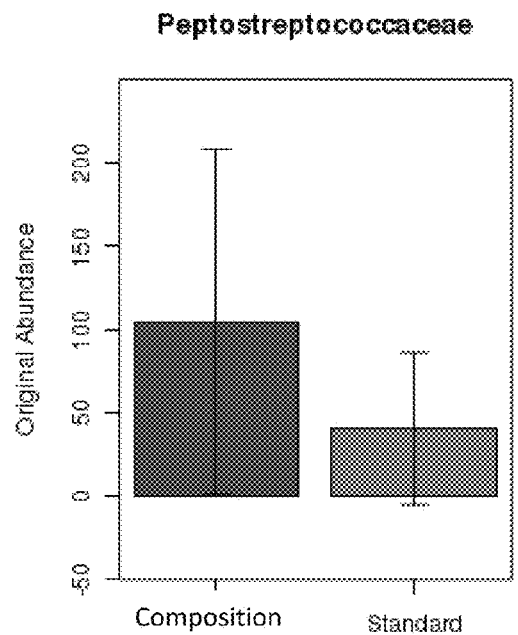
FIG. 86 is a plot of original abundance illustrating the amount of Peptostreptococcaceae in the control and treatment groups at day 32.
Figure 87:
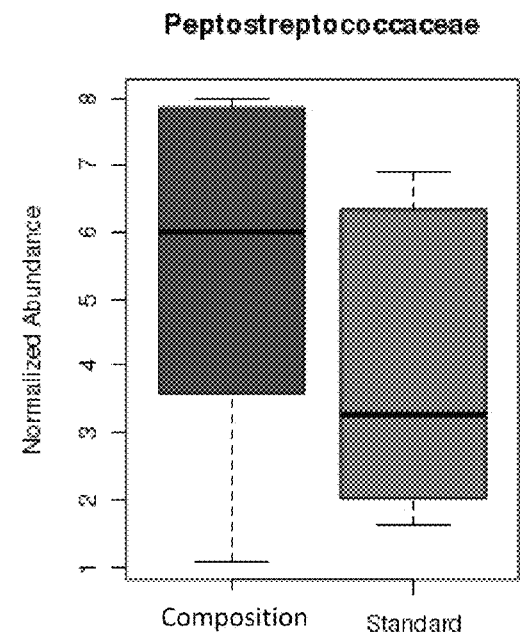
FIG. 87 is a plot of normalized abundance illustrating the amount of Peptostreptococcaceae in the control and treatment groups at day 32.
Figure 88:
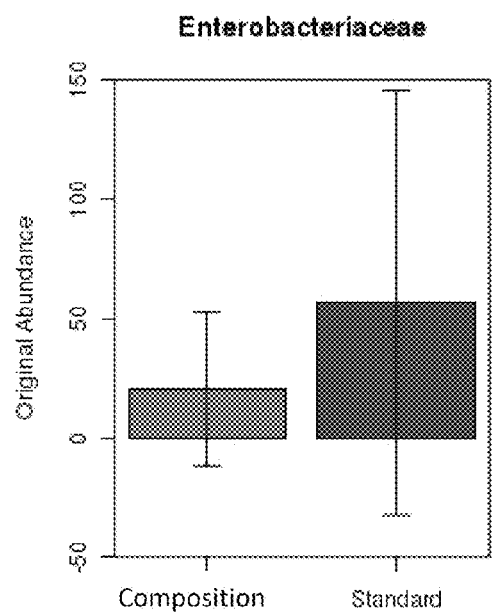
FIG. 88 is a plot of original abundance illustrating the amount of *E. coli* in the control and treatment groups at day 84.
Figure 89:
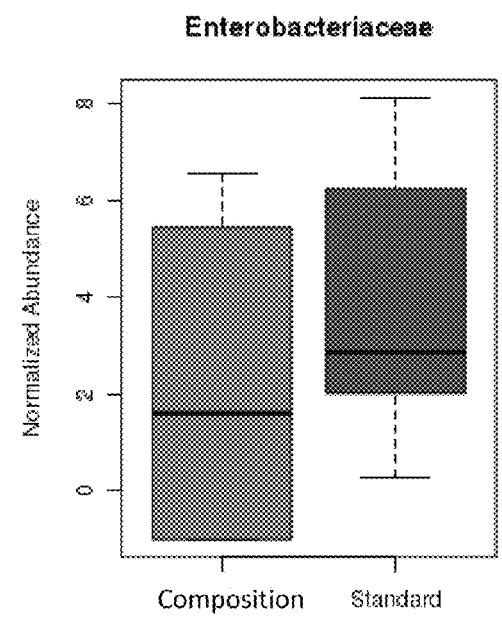
FIG. 89 is a plot of normalized abundance illustrating the amount of *E. coli* in the control and treatment groups at day 84.
Figure 90:
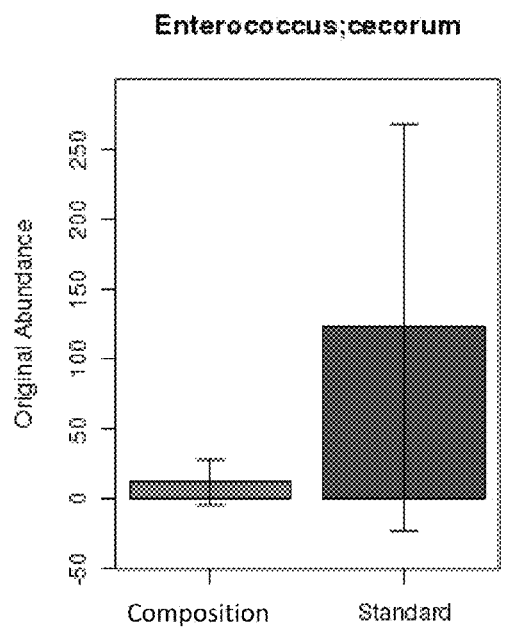
FIG. 90 is a plot of original abundance illustrating the amount of *Enterococcus cecorum* in the control and treatment groups at day 84.
Figure 91:
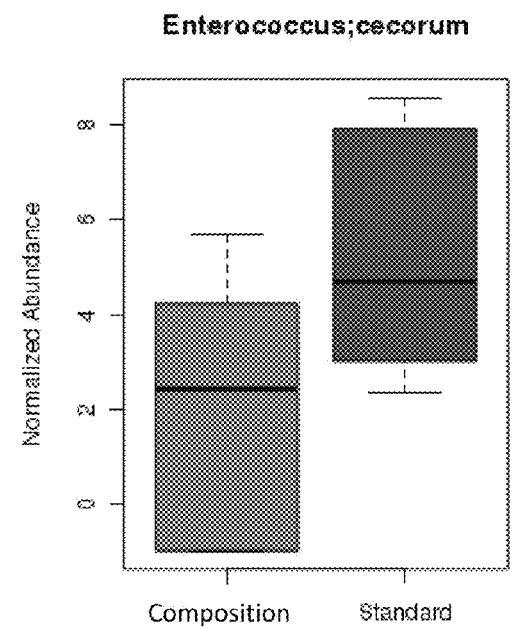
FIG. 91 is a plot of normalized abundance illustrating the amount of *Enterococcus cecorum* in the control and treatment groups at day 84.

By day 32, segmented filamentous bacteria (*Candidatus Arthromitus*) had appeared in the control group (FIGS. 78 and 79). However, the abundance was lower than was observed in the treatment group 11 days earlier. This again suggested an earlier appearance and increased abundance of these bacteria in the treatment group. Also, a significant decrease in *Corynebacterium* species, *E. coli*, and *Staphylococcus* species (FIGS. 80-85) was observed. And an increase in Peptostreptococcaceae was detected (FIGS. 86 and 87), including butyrate producing bacteria that are shown to be positively correlated with improved gut health.

Figure 92:
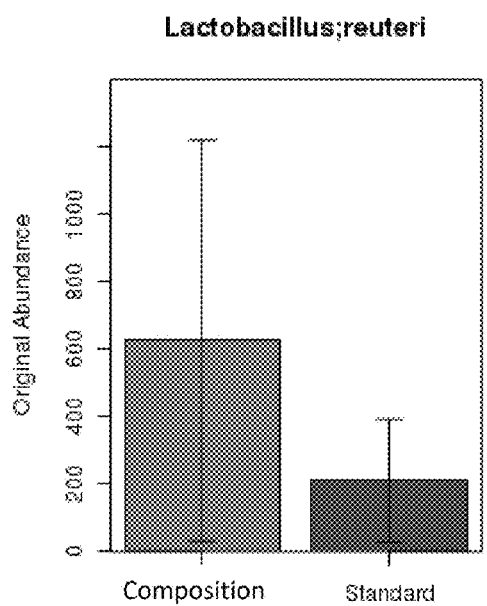
FIG. 92 is a plot of original abundance illustrating the amount of *Lactobacillus reuteri* in the control and treatment groups at day 84.
Figure 93:
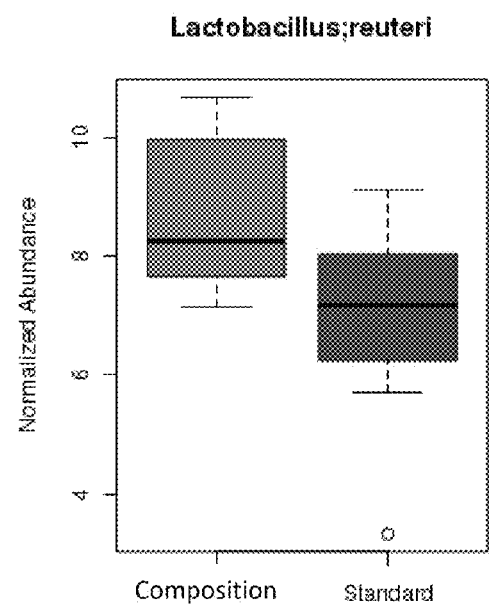
FIG. 93 is a plot of normalized abundance illustrating the amount of *Lactobacillus reuteri* in the control and treatment groups at day 84.
Figure 94:
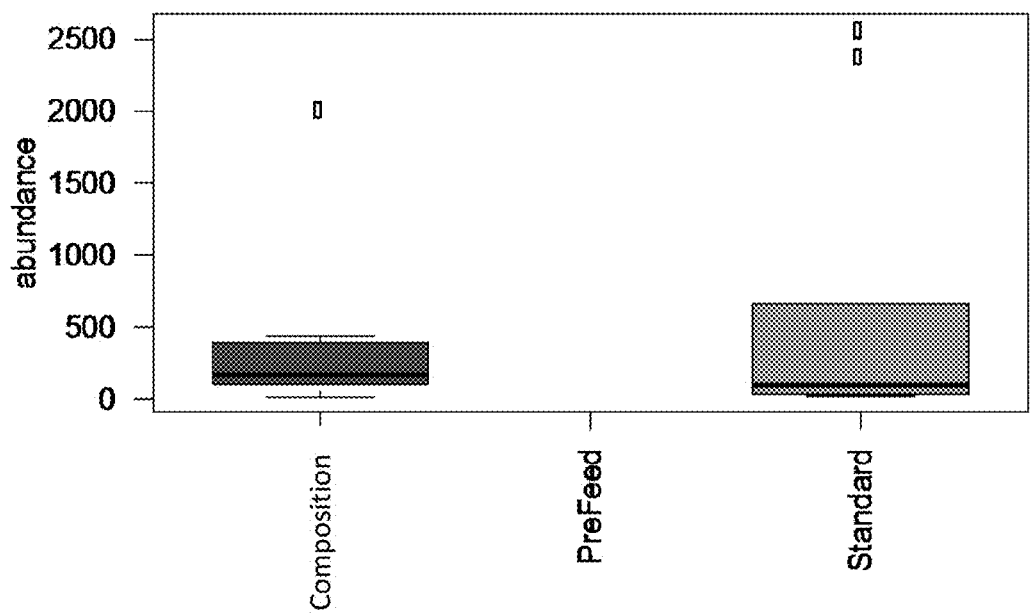
FIG. 94 is a plot of abundance versus treatment illustrating the amount of *E. coli* detected at day 3.
Figure 95:
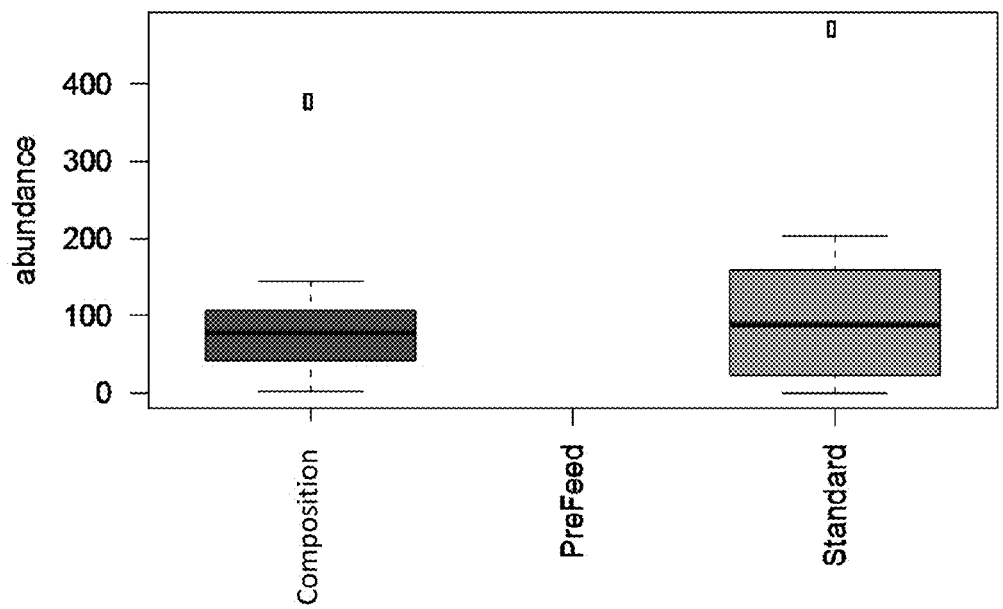
FIG. 95 is a plot of abundance versus treatment illustrating the amount of *E. coli* detected at day 7.
Figure 96:
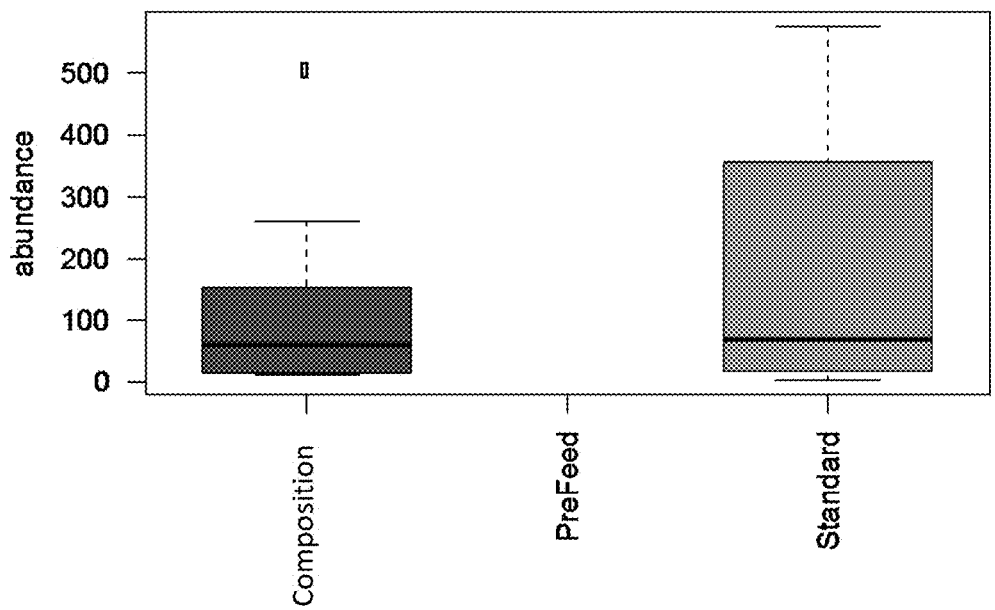
FIG. 96 is a plot of abundance versus treatment illustrating the amount of *E. coli* detected at day 14.
Figure 97:
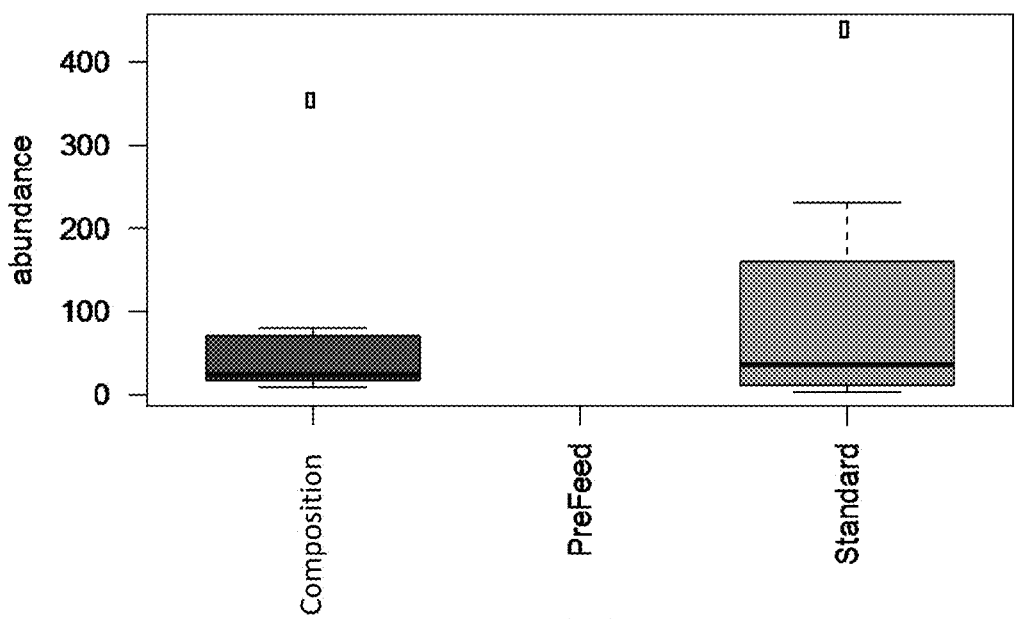
FIG. 97 is a plot of abundance versus treatment illustrating the amount of *E. coli* detected at day 21.
Figure 98:
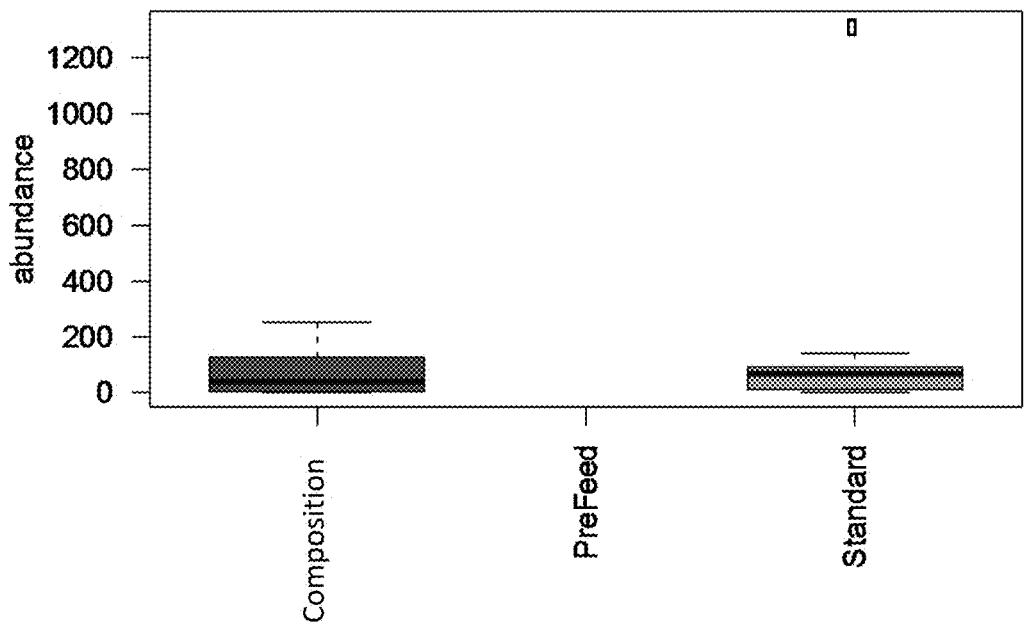
FIG. 98 is a plot of abundance versus treatment illustrating the amount of *E. coli* detected at day 32.
Figure 99:
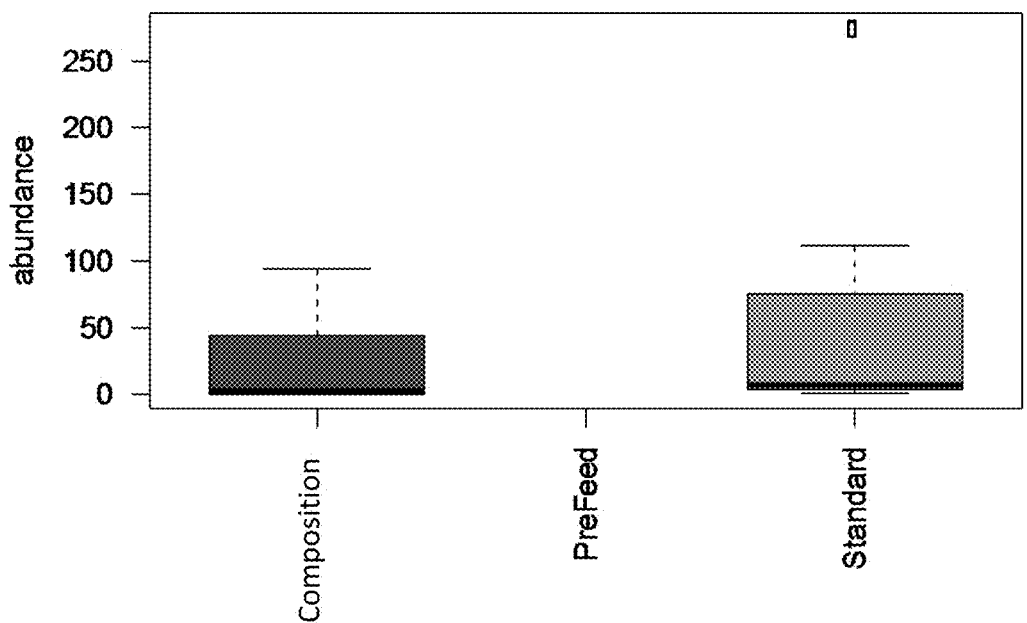
FIG. 99 is a plot of abundance versus treatment illustrating the amount of *E. coli* detected at day 84.
Figure 100:
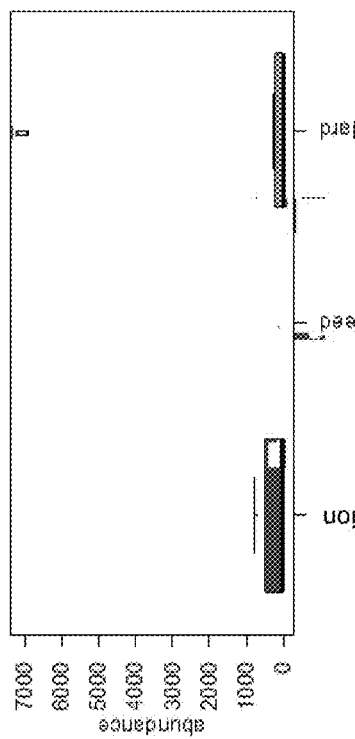
FIG. 100 is a plot of abundance versus treatment illustrating the difference in the amount of *Candidatus Arthromitus* detected between the control and treatment groups.
Figure 101:
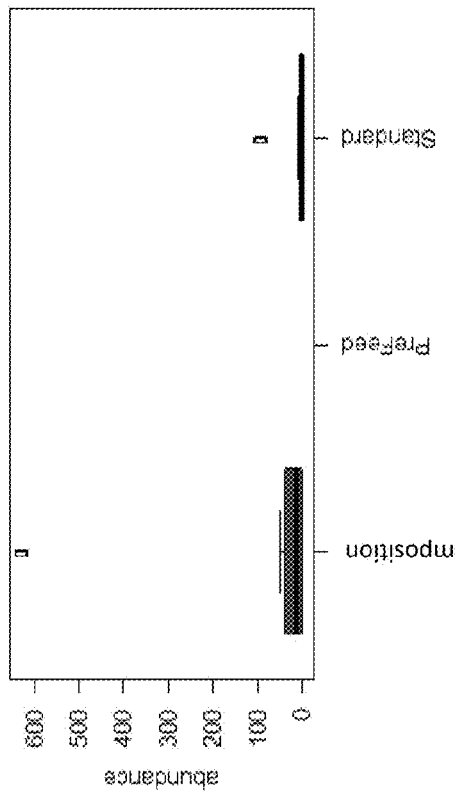
FIG. 101 is a plot of abundance versus treatment illustrating the difference in the amount of *Candidatus Arthromitus* detected between the control and treatment groups.
Figure 102:
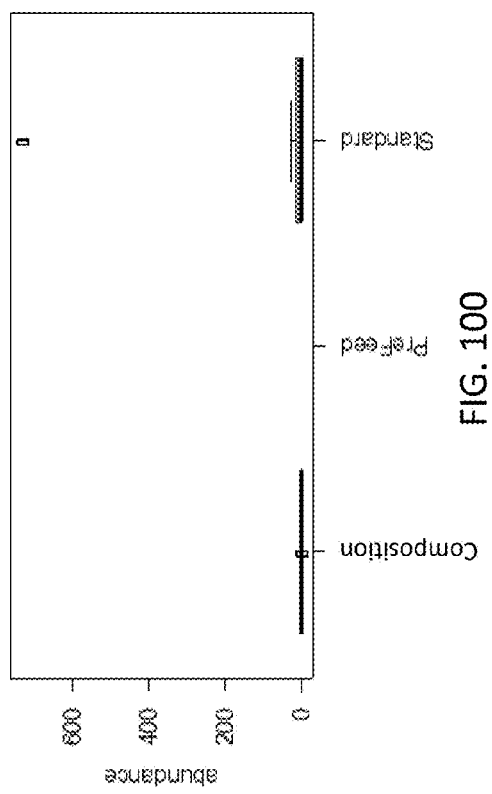
FIG. 102 is a plot of abundance versus treatment illustrating the difference in the amount of *Candidatus Arthromitus* detected between the control and treatment groups.
Figure 103:
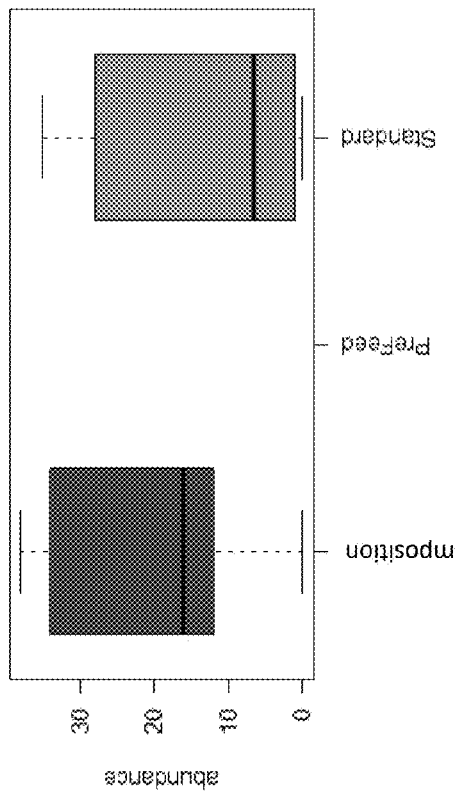
FIG. 103 is a plot of abundance versus treatment illustrating the difference in the amount of *Candidatus Arthromitus* detected between the control and treatment groups.
Figure 104:
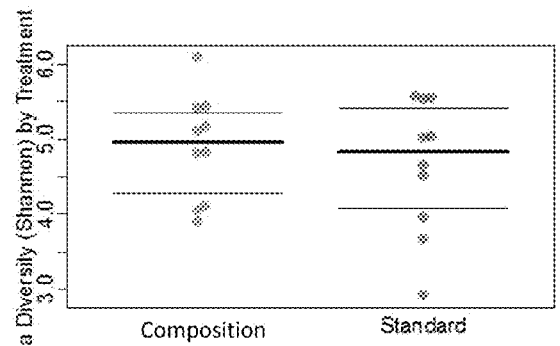
FIG. 104 is a plot of diversity versus treatment, illustrating the bacterial community diversity of the control and treatment groups at day 3.
Figure 105:
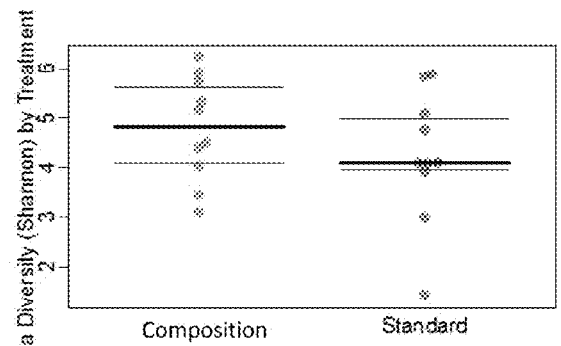
FIG. 105 is a plot of diversity versus treatment, illustrating the bacterial community diversity of the control and treatment groups at day 7.
Figure 106:
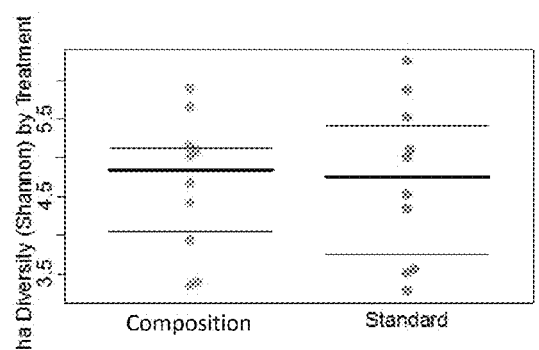
FIG. 106 is a plot of diversity versus treatment, illustrating the bacterial community diversity of the control and treatment groups at day 14.
Figure 107:
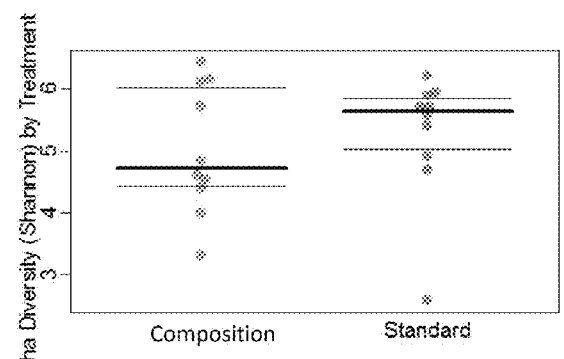
FIG. 107 is a plot of diversity versus treatment, illustrating the bacterial community diversity of the control and treatment groups at day 21.
Figure 108:
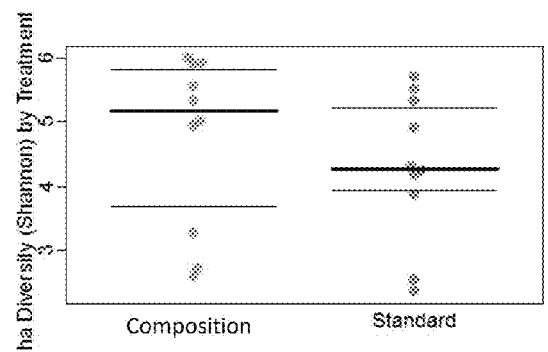
FIG. 108 is a plot of diversity versus treatment, illustrating the bacterial community diversity of the control and treatment groups at day 32.
Figure 109:
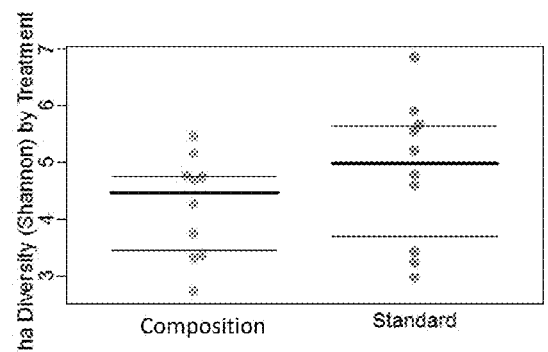
FIG. 109 is a plot of diversity versus treatment, illustrating the bacterial community diversity of the control and treatment groups at day 84.

And at day 84 significant decreases in *E. coli* and also *Enterococcus cecorum* were observed (FIGS. 88-91). And an increase in *Lactobacillus reuteri* was detected (FIGS. 92 and 93).

Additionally, the amounts of specific bacteria were examined across time points to validate some of the observations seen in significantly changed taxa. *E. coli* was decreased at all time points except day 32 (FIGS. 94-99, increasing in age). And, segmented filamentous bacteria (*Candidatus Arthromitus*) increased in treatment on day 7, 14, and 21 (FIGS. 100-103).

Additionally, the bacterial community diversity of control versus treatment at each time point was examined, and is illustrated in FIGS. 104-109. Overall, the results were non-significant and varied between time points, suggesting there was not a significant change in bacterial diversity between control and treatment groups.

Table 32 provides twenty bacterial species identified in the samples, grouped by age and treatment.

TABLE 32

|  | Standard D 03 | Composition D 03 | Standard D 07 | Composition D 07 |
|---|---|---|---|---|
| Lactobacillus aviarius | 0.6 | 0.8 | 567.8 | 264 |
| Lactobacillus reuteri | 13.1 | 216.2 | 1441.6 | 736.4 |
| Romboutsia | 0.4 | 0.3 | 0.7 | 0.7 |
| Lactobacillus salivarius | 16.1 | 515.8 | 195.5 | 306.5 |
| Lactobacillus johnsonii | 688.3 | 538.7 | 274.2 | 275.7 |
| Lactobacillus acidophilus | 85.4 | 51.5 | 251.8 | 107.9 |
| Lactobacillus gasseri | 462.7 | 367 | 181.7 | 182.7 |
| Ruminococcus | 439.2 | 726.2 | 287.1 | 659.3 |
| Ruminococcus2 | 433.8 | 404.9 | 163.2 | 165 |
| Oscillospira | 261.6 | 403.1 | 127.8 | 238.5 |
| Bifidobacterium | 0.01 | 0.01 | 2.1 | 0.01 |
| Faecalibacterium prausnitzii | 278.1 | 202 | 58.5 | 113.6 |
| Ruminococcus3 | 439 | 22.5 | 131.4 | 137.4 |
| Escherichia coli | 614.5 | 370.4 | 121.4 | 99.7 |
| Rikenellaceae | 1.2 | 0.4 | 759 | 4.5 |
| Faecalibacterium prausnitzii2 | 10.8 | 1.3 | 554 | 0.4 |
| Ruminococcus4 | 394.4 | 392.3 | 66.8 | 222.7 |
| Streptococcus | 139.3 | 86.7 | 168.2 | 698.8 |
| Faecalibacterium prausnitzii3 | 184.3 | 58.2 | 81.7 | 129.8 |
| Clostridiales | 370.7 | 238 | 111.1 | 147.8 |

|  | Standard D 14 | Composition D 14 | Standard D 21 | Composition D 21 |
|---|---|---|---|---|
| Lactobacillus aviarius | 1963.9 | 1612.8 | 1354 | 889.8 |
| Lactobacillus reuteri | 573.7 | 1152 | 569.1 | 547.8 |
| Romboutsia | 0.5 | 0.3 | 1.8 | 1.3 |
| Lactobacillus salivarius | 628.8 | 312.8 | 237 | 539.9 |
| Lactobacillus johnsonii | 755.4 | 525.4 | 519 | 341.6 |
| Lactobacillus acidophilus | 958.2 | 1241.6 | 97.4 | 419.6 |
| Lactobacillus gasseri | 503.8 | 345.8 | 297 | 192 |
| Ruminococcus | 69.7 | 73.7 | 61.3 | 133 |
| Ruminococcus2 | 109.8 | 188.8 | 214 | 349.4 |
| Oscillospira | 125.8 | 223.4 | 310.1 | 379.4 |
| Bifidobacterium | 139.1 | 170.7 | 212.3 | 147.8 |
| Faecalibacterium prausnitzii | 140.7 | 68.6 | 369.5 | 446.2 |

TABLE 32-continued

| | | | | |
|---|---|---|---|---|
| Ruminococcus3 | 132.3 | 223.7 | 121.4 | 223.2 |
| Escherichia coli | 166 | 122.7 | 109.1 | 66 |
| Rikenellaceae | 54 | 69.3 | 415 | 211.9 |
| Faecalibacterium prausnitzii2 | 318.6 | 256.4 | 148.2 | 65.6 |
| Ruminococcus4 | 53.2 | 29.2 | 107.6 | 93.3 |
| Streptococcus | 3.3 | 3.6 | 12.4 | 2.3 |
| Faecalibacterium prausnitzii3 | 85.7 | 20 | 282.4 | 229.4 |
| Clostridiales | 25.8 | 152.8 | 78.3 | 259.5 |

| | Standard D 32 | Composition D 32 | Standard D 84 |
|---|---|---|---|
| Lactobacillus aviarius | 2123.2 | 1173.7 | 1494.4 |
| Lactobacillus reuteri | 263 | 44.3 | 205.8 |
| Romboutsia | 12 | 63.4 | 2581.8 |
| Lactobacillus salivarius | 744.3 | 997.3 | 110.3 |
| Lactobacillus johnsonii | 54.6 | 11.2 | 263.5 |
| Lactobacillus acidophilus | 112.4 | 685.1 | 118.2 |
| Lactobacillus gasseri | 40.1 | 5.5 | 148.6 |
| Ruminococcus | 36.6 | 75.8 | 31.5 |
| Ruminococcus2 | 377.6 | 151.7 | 13.1 |
| Oscillospira | 173.2 | 117.9 | 56.1 |
| Bifidobacterium | 875.7 | 557.6 | 133.7 |
| Faecalibacterium prausnitzii | 137 | 194.6 | 101.3 |
| Ruminococcus3 | 270 | 92.4 | 146 |
| Escherichia coli | 180.3 | 78.7 | 55.4 |
| Rikenellaceae | 110.9 | 329.4 | 19.3 |
| Faecalibacterium prausnitzii2 | 249.2 | 220.7 | 9.4 |
| Ruminococcus4 | 34.1 | 92.2 | 82.6 |
| Streptococcus | 6.4 | 2.7 | 363.9 |
| Faecalibacterium prausnitzii3 | 226.6 | 192.9 | 28.9 |
| Clostridiales | 59.5 | 25 | 1 |

Conclusion

The relative abundance of several bacterial taxa were changed in birds that were fed a composition comprising Yucca schidigera and Quillaja saponaria, compared to birds that were not fed the composition. Some changes occurred at specific times, and other changes occurred across several time points. This suggests that biologically meaningful changes to the microbiome occurred as a result of administration of the composition. Specifically, changes included reductions in common pathogens such as E. coli, Clostridium spp., Enterococcus spp., Staphylococcus spp., and Streptococcus spp., and enrichment of Lactobacillus reuteri and in the abundance of segmented filamentous bacteria. Overall, these specific modifications to the gut microbiome indicate that administration of the composition may reduce pathogen load in the gut and enrich beneficial bacteria that accelerate gut microbiome maturation.

Overview of Several Embodiments

In some embodiments disclosed herein, the combination can comprise 200 ppm to 5,000 ppm of a first composition comprising Quillaja saponaria, Yucca schidigera, or a combination thereof; and a second composition comprising an antimicrobial agent, an antibiotic, an anticoccidial agent, or combinations thereof; wherein the combination is formulated for administration to a chicken or turkey; or greater than 0 ppm to 5,000 ppm of the first composition comprising Quillaja saponaria, Yucca schidigera, or a combination thereof; and the second composition; wherein the combination is formulated for administration to an animal other than a chicken or turkey.

In some embodiments, the combination is formulated for avian other than chicken or turkey, livestock, aquaculture species, domesticated animals, ruminants, or ungulates. In some embodiments the chicken is a broiler chicken.

In some embodiments, the first composition is formulated for administration to an animal other than a chicken or turkey and the amount of the first composition ranges from 50 ppm to 5,000 ppm. In some embodiments, the first composition is formulated for administration to an animal other than a chicken or turkey and the amount of the first composition ranges from 50 ppm to 2,500 ppm.

In any or all of the above embodiments, the first composition comprises a mixture of Quillaja saponaria and Yucca schidigera in a ratio ranging from 70:30 Quillaja saponaria:Yucca schidigera to 90:10 Quillaja saponaria:Yucca schidigera.

In any or all of the above embodiments, the second composition comprises 10 ppm to 30 ppm Virginiamycin.

In any or all of the above embodiments, the second composition comprises 25 ppm to 90 ppm Salinomycin.

In any or all of the above embodiments, the combination can comprise a third composition comprising a vaccine. In some embodiments, the vaccine is a coccidiosis vaccine comprising oocysts derived from Eimeria acervulina, Eimeria mivati, Eimeria maxima, Eimeria tenella, Eimeria necatrix, Eimeria mitis, Eimeria praecox, Eimeria brunetti, Eimeria hagani, or combinations thereof.

In any or all of the above embodiments, the Quillaja saponaria is a Quillaja saponaria plant extract, the Yucca schidigera is a Yucca schidigera plant extract, or both. In some embodiments, the Quillaja saponaria plant extract comprises at least one saponin, polyphenol, antioxidant, resveratrol or any combination thereof. In some embodiments, the Yucca schidigera plant extract comprises at least one saponin, polyphenol, antioxidant, resveratrol or any combination thereof.

In any or all of the above embodiments, the first and second compositions are admixed to form an admixed composition.

In any or all of the above embodiments, the first composition, the second composition, and third composition are admixed to form an admixed composition. In some embodiments, the admixed composition is further admixed with a feedstuff to form a feedstuff admixture. In some embodiments, the components of the admixed composition, the feedstuff admixture, or both, are sized, concentrated, or diluted to facilitate admixing, facilitate administration to an animal, or combinations thereof.

In any or all of the above embodiments, the combination can further comprise a vitamin, a trace mineral, a bulking agent, a carrier, a colorant, a taste enhancer, or any combination thereof.

In any or all of the above embodiments, the combination can further comprise corn, soybean meal, wheat, barley, rye, canola, corn oil, limestone, salt, distillers dried grains with solubles (DDGS), dicalcium phosphate, sodium sesquicarbonate, methionine source, lysine source, L-threonine, choline, or any combination thereof.

In any or all of the above embodiments, the combination is administered to an animal that has been or is at risk of being exposed to coccidia. In some embodiments, the coccidia are ionophore-resistant coccidia.

In some embodiments, the combination comprises 200 ppm to 300 ppm of a first composition comprising *Quillaja saponaria, Yucca schidigera*, or a combination thereof; and 10 ppm to 70 ppm of an antibiotic, antimicrobial, anticoccidial, or combination thereof; and wherein the combination is formulated for administration to a domestic fowl.

Also disclosed herein are embodiments of methods comprising administering a combination as disclosed herein to an animal at least once daily from day of age and for a time period sufficient to promote a beneficial health effect. In some embodiments, the combination comprises 200 ppm to 5,000 ppm of a first composition comprising *Quillaja saponaria, Yucca schidigera*, or a combination thereof; and a second composition comprising an antimicrobial agent, an antibiotic, an anticoccidial agent, or a combination thereof, and wherein the combination is administered to a chicken or turkey. In some embodiments, the combination comprises greater than 0 ppm to 5,000 ppm of a first composition comprising *Quillaja saponaria, Yucca schidigera*, or a combination thereof; and a second composition comprising an antimicrobial agent, an antibiotic, an anticoccidial agent, or combinations thereof, and wherein the combination is administered to an animal other than a chicken or turkey.

In any or all of the above embodiments, the first composition comprises a mixture of *Quillaja saponaria* and *Yucca schidigera* in a ratio ranging from 70:30 *Quillaja saponaria:Yucca schidigera* to 90:10 *Quillaja saponaria:Yucca schidigera*.

In any or all of the above embodiments, the first and second compositions are administered substantially simultaneously.

In any or all of the above embodiments, the first and second compositions are administered sequentially, in any order.

In any or all of the above embodiments, the method can further comprise administering the first composition and the second composition in combination with a feedstuff.

In some embodiments, the combination is administered to a chicken or turkey and the feedstuff is provided in an amount ranging from at least 7 lbs to 10 lbs of a feedstuff per chicken or turkey. In some embodiments, the first composition, the second composition, and the feedstuff are administered substantially simultaneously. In some embodiment, the first composition, the second composition, and the feedstuff are administered sequentially, in any order.

In any or all of the above embodiments, the method comprises administering a third composition comprising a coccidiosis vaccine comprising oocysts derived from *Eimeria acervulina, Eimeria mivati, Eimeria maxima, Eimeria tenella, Eimeria necatrix, Eimeria mitis, Eimeria praecox, Eimeria brunetti, Eimeria hagani*, or combinations thereof. In some embodiments, the first composition, second composition, third composition, and the feedstuff are administered substantially simultaneously. In some embodiments, the first composition, second composition, third composition, and the feedstuff are administered sequentially, in any order.

In any or all of the above embodiments, the animal other than a chicken or turkey is an avian other than a chicken or turkey, a mammal, a ruminant, an ungulate, or an aquaculture species. In some embodiments, the chicken is a broiler meat-type chicken.

In any or all of the above embodiments, the animal has a lower feed conversion rate relative to an animal not administered the combination. In some embodiments, the feed conversion rate is improved by at least 0.5% to at least 5%.

In any or all of the above embodiments, the administration of the combination to the animal has a beneficial effect on the health of the animal relative to an animal not administered the combination. In some embodiments, the beneficial effect on the health of the animal is a beneficial effect on the digestive system of the animal. In some embodiments, the method comprises improving feed conversion rate in animal in a commercial feed operation by administering at least once daily a mixture comprising a feedstuff, an antimicrobial, an antibiotic, an anticoccidial agent, or a combination thereof, and 200 ppm to 5,000 ppm *Quillaja saponaria, Yucca schidigera*, or both, wherein the mixture improves the animal's feed conversion rate by greater than 0.5% up to at least 5% relative to an animal that is not administered the mixture. In some embodiments, the first composition comprises a mixture of *Quillaja saponaria* and *Yucca schidigera* in a ratio ranging from 70:30 *Quillaja saponaria:Yucca schidigera* to 90:10 *Quillaja saponaria:Yucca schidigera*.

Also disclosed herein are embodiments of a method for making a combination, comprising providing a first composition comprising *Quillaja saponaria, Yucca schidigera*, or both; providing a second composition comprising an antimicrobial agent, an antibiotic, an anticoccidial agent, or a combination thereof; and combining the first and second compositions. In some embodiments, the amount of the first composition ranges from greater than 0 ppm to 5,000 ppm. In some embodiments, the amount of the first composition ranges from 50 ppm to 5,000 ppm.

In any or all of the above embodiments, the *Quillaja saponaria* is a *Quillaja saponaria* plant extract, the *Yucca schidigera* is a *Yucca schidigera* plant extract, or both. In some embodiments, the *Quillaja saponaria* plant extract comprises at least one saponin, the *Yucca schidigera* plant extract comprises at least one saponin, or both.

In any or all of the above embodiments, the first composition comprises a mixture of *Quillaja saponaria* and *Yucca schidigera* in a ratio ranging from 70:30 *Quillaja saponaria:Yucca schidigera* to 90:10 *Quillaja saponaria:Yucca schidigera*.

In any or all of the above embodiments, the method further comprises admixing the combination with a feedstuff to form an admixed feedstuff. In some embodiments, the method further comprises formulating the first and/or second compositions for mixture with the feedstuff to provide a substantially homogeneous admixed feedstuff.

In any or all of the above embodiments, the method further comprises combining the first composition, the second composition, or both with a third composition comprising a vaccine. In some embodiments, the first composition, second composition, and third composition are admixed simultaneously or sequentially.

In view of the many possible embodiments to which the principles of the present disclosure may be applied, it should be recognized that the illustrated embodiments are only preferred examples of the disclosure and should not be taken as limiting the scope of the claimed invention. We claim as our invention all that comes within the scope and spirit of the following claims.

We claim:

1. A combination of compositions, comprising a first composition comprising *Quillaja saponaria* processed plant material and/or an extract thereof and *Yucca schidigera* processed plant material and/or an extract thereof in a ratio ranging from 70-90:10-30 of *Quillaja saponaria:Yucca schidigera*, respectively, and a second composition comprising 10 ppm to 30 ppm Virginiamycin, 25 ppm to 90 ppm Salinomycin, or combinations thereof, wherein the combination is formulated for administration to a chicken or turkey.

2. The combination of claim 1, further comprising a third composition comprising a vaccine.

3. The combination of claim 2, wherein the vaccine is a coccidiosis vaccine comprising oocysts obtained from *Eimeria acervulina, Eimeria mivati, Eimeria maxima, Eimeria tenella, Eimeria necatrix, Eimeria mitis, Eimeria praecox, Eimeria brunetti, Eimeria* hagani, or combinations thereof.

4. A combination, comprising 10 ppm to 5,000 ppm of a first composition comprising *Quillaja saponaria* processed plant material and/or an extract thereof and *Yucca schidigera* processed plant material and/or an extract thereof, and a second composition comprising an antimicrobial agent, an antibiotic, an anticoccidial agent, 10 ppm to 30 ppm Virginiamycin, 25 ppm to 90 ppm Salinomycin, or a combination thereof, wherein the combination is formulated for administration to an animal other than a chicken or turkey.

5. The combination of claim 4, wherein the combination comprises from 50 ppm to 2,500 ppm of the first composition.

6. The combination of claim 4, further comprising a third composition comprising a vaccine.

7. A method, comprising administering the composition combination of claim 1 to a chicken or turkey.

8. The method of claim 7, wherein the combination is administered to the chicken or the turkey from day of age.

9. The method of claim 7, wherein the chicken is a broiler meat-type chicken.

10. The method of claim 7, wherein the chicken or turkey has a lower feed conversion rate.

11. The method of claim 10, wherein the feed conversion rate is improved by at least 0.5% to at least 5%.

12. The method of claim 7, wherein the combination is administered at least once daily for a time period sufficient to promote a beneficial health effect.

13. The method of claim 12, wherein the beneficial health effect on the chicken or turkey is a beneficial effect on the digestive system of the chicken or turkey.

14. The method of claim 12, wherein the beneficial health effect on the chicken or turkey comprises an earlier appearance of segmented filamentous bacteria, an increase in the abundance of segmented filamentous bacteria, an increase in the abundance of *Lactobacillus*, or a combination thereof.

15. The method of claim 7, wherein the first and second compositions are administered substantially simultaneously.

16. The method of claim 7, wherein the first and second compositions are administered sequentially, in any order.

17. The method of claim 7 further comprising combining the first and second compositions with a feedstuff to form a mixture and administering the mixture to the chicken or the turkey.

18. The method of claim 15, further comprising administering a third composition comprising a coccidiosis vaccine comprising oocysts obtained from *Eimeria acervulina, Eimeria mivati, Eimeria maxima, Eimeria tenella, Eimeria necatrix, Eimeria mitis, Eimeria praecox, Eimeria brunetti, Eimeria hagani*, or combinations thereof.

19. The method of claim 18, wherein the first composition, the second composition and the third composition are administered substantially simultaneously, or sequentially in any order.

20. A method, comprising administering the combination of claim 4 to an animal other than a chicken or a turkey at least once daily for a time period sufficient to promote a beneficial health effect.

21. The method of claim 20, wherein the animal is a mammal, an aquaculture species, or an avian other than a chicken or turkey.

22. The combination of claim 1, wherein the *Quillaja saponaria* is processed *Quillaja* plant material and the *Yucca schidigera* is processed *Yucca* plant material.

23. The combination of claim 1, further comprising a feedstuff, Bacitracin MD, Zinc Bacitracin, Tylosin, Lincomycin, Flavomycin, Terramycin, Neo-Terramycin, penicillin, tetracycline, ceftiofur, florfenicol, tilmicosin, enrofloxacin, tulathromycin, procaine penicillin, benzathine penicillin, ampicillin, amoxicillin, spectinomycin, dihydrostreptomycin, chlortetracycline, gentamicin, sulphadimidine, trimethoprim, oxytetracycline, erythromycin, or norfloxacin, Monensin, Lasalocid, Narasin, Maduramicin, Semduramicin, Laidlomycin, Nicarbazin, Maxiban, Diclazuril, Toltrazuril, Robenidine, Stenorol, Clopidol, Decoquinate, DOT (zoalene), Amprolium, or a combination thereof.

24. The combination of claim 1, wherein the *Quillaja saponaria* is an extract and the *Yucca schidigera* is an extract.

* * * * *